(12) United States Patent
Sakata et al.

(10) Patent No.: US 7,320,973 B2
(45) Date of Patent: Jan. 22, 2008

(54) DIHYDRODIARYLOXAZEPINE DERIVATIVE AND PHARMACEUTICAL COMPOSITION CONTAINING THE SAME

(75) Inventors: Katsutoshi Sakata, Kawasaki (JP); Takashi Tsuji, Kawasaki (JP); Munetaka Tokumasu, Kawasaki (JP); Kazuyoshi Takahashi, Kawasaki (JP); Shigeo Hirasawa, Kawasaki (JP); Junko Ezaki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 391 days.

(21) Appl. No.: 10/724,179

(22) Filed: Dec. 1, 2003

(65) Prior Publication Data

US 2004/0110742 A1 Jun. 10, 2004

Related U.S. Application Data

(63) Continuation of application No. PCT/JP02/05193, filed on May 29, 2002.

(30) Foreign Application Priority Data

May 30, 2001 (JP) ............................. 2001-161988

(51) Int. Cl.
*A61P 1/00* (2006.01)
*A61K 31/553* (2006.01)
*C07D 267/18* (2006.01)
*C07D 413/00* (2006.01)

(52) U.S. Cl. ............................. 514/211.02; 514/211.1; 514/211.12; 540/548; 540/550

(58) Field of Classification Search .......... 514/211.02, 514/211.1, 211.12; 540/548, 550
See application file for complete search history.

(56) References Cited

U.S. PATENT DOCUMENTS

| | | | | |
|---|---|---|---|---|
| 6,127,361 A | 10/2000 | Tanaka et al. | ........... | 514/211.11 |
| 6,436,922 B1 | 8/2002 | Tanaka et al. | ........... | 514/211.11 |
| 6,528,504 B2 | 3/2003 | Sakata et al. | ........... | 514/211.11 |
| 6,562,808 B1 | 5/2003 | Sakata et al. | ............ | 514/211.1 |

FOREIGN PATENT DOCUMENTS

| | | |
|---|---|---|
| EP | 0 404 359 A1 | 12/1990 |
| EP | 0 889 043 A1 | 1/1999 |
| EP | 1 020 466 A1 | 7/2000 |
| JP | 2000-351778 | 12/2000 |
| WO | WO97/33885 | 9/1997 |
| WO | WO99/12925 | 3/1999 |
| WO | WO00/40570 | 7/2000 |
| WO | WO01/17980 A1 | 3/2001 |
| WO | WO02/48120 A1 | 6/2002 |

OTHER PUBLICATIONS

U.S. Appl. No. 10/724,179, filed Dec. 1, 2003, Sakata et al.
U.S. Appl. No. 10/086,781, filed Mar. 4, 2002, Sekiyama et al.
P. Quinn et al, "UK-84,149: A Potent and Gut-Selective Spasmolytic in the Anaesthetised Dog", *British Journal of Pharmacology*, 1994, vol. 112, Proceedings Supplement, 573P.
R.M. Wallis et al, "UK-84,149: A Novel Gut-Selective Spasmolytic with Calcium Antagonist Activity", *British Journal of Pharmacology*, 1994, vol. 112, Proceedings Supplement, 574P.
F. Narducci et al, "Nifedipine Reduces the Colonic Motor Response to Eating in Patients with the Irritable Colon Syndrome", *The American Journal of Gastroenterology*, May 1985, vol. 80, No. 5, pp. 317-319.
A. Prior et al, "Reduction of colonic motility by intravenous nicardipine in irritable bowel syndrome", *Gut*, 1987, vol. 28, pp. 1609-1612.

(Continued)

*Primary Examiner*—Brenda Coleman
(74) *Attorney, Agent, or Firm*—Oblon, Spivak, McClelland, Maier & Neustadt, P.C.

(57) ABSTRACT

The present invention provides dihydrodiaryloxazepine derivative represented by the following formula [1], analogs thereof and pharmaceutical compositions containing them. Those compounds have an excellent effect of improving functional diseases of gastrointestinal tracts

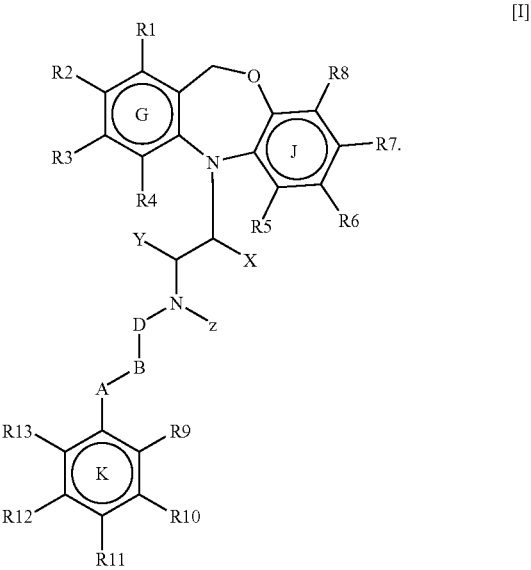

26 Claims, No Drawings

OTHER PUBLICATIONS

*J. Clin. Psychiatry*, Sep. 1987, vol. 48, No. 9, pp. 388-389.

F. De Ponti et al, "Calcium-Channel Blockers and Gastrointestinal Motility: Basic and Clinical Aspects", *Pharmac. Ther.*, 1993, vol. 60, pp. 121-148.

H. L. Yale et al, "Novel Polycyclic Heterocycles. II. Derivatives of 5,11-Dihydrodibenz[*b*,*e*][1,4]oxazepine[1]", *J. Med. Chem.*, Sep. 1964, vol. 7, pp. 609-614.

G. J. Sanger et al, "Increased defecation during stress or after 5-hydroxytryptophan: selective inhibition by the 5-HT$_4$ receptor antagonist, SB-207266", *British Journal of Pharmacology*, 2000, vol. 130, pp. 706-712.

K. Hara et al, "Antinociceptive Effects of Intrathecal L-Type Calcium Channel Blockers on Visceral and Somatic Stimuli in the Rat", *Anesth. Analg.*, 1998, vol. 87, pp. 382-387.

DIHYDRODIARYLOXAZEPINE DERIVATIVE AND PHARMACEUTICAL COMPOSITION CONTAINING THE SAME

CROSS REFERENCES TO RELATED APPLICATIONS

This application is a continuation of International Patent Application No. PCT/JP02/05193, filed on May 29, 2002, and claims priority to Japanese Patent Application No. 2001-161988, filed on May 30, 2001.

BACKGROUND OF THE INVENTION

The present invention relates to 5,11-dihydrodiaryl[b,e][1,4]oxazepine derivatives, antagonistic to calcium channels and useful for treating or preventing functional diseases of gastrointestinal tracts, in particular, irritable bowel syndrome, and stereoisomers thereof, pharmacologically acceptable salts thereof or hydrates thereof and also pharmaceutical compositions containing any of them as the active ingredient.

The present invention also relates to intermediates for producing the new 5,11-dihydrodiaryl[b,e][1,4]oxazepine derivatives.

It is disclosed in, for example, European Patent No. 0404359 that the 5,11-dihydrodibenzo[b,e][1,4]thiazepine derivatives are useful as antagonists to calcium channels, which are selective for the gastrointestinal tracts. Quinn, P. et al. [Brit. H. Pharmacol., 1994, 112 (Suppl.), Abst. P. 573] and Wallis, R. M. et al. [Brit. J. Pharmacol., 1994, 112 (Suppl.), Abst. P. 574]disclosed that (S)-5-[[1-(4-methoxyphenyl)ethyl]pyrrolidin-2-ylmethyl]-5,11-dihydrodibenzo[b,e]-[1,4]thiazepine maleate has the same effect as the one described above. However, the activity and selectivity of those compounds for the gastrointestinal tracts are not yet satisfactory and another defect of them is that they have an anticholinergic effect that causes side effects such as a thirst and mydriasis. Further, International Patent Nos. 9733885A1 and 9912925A1 disclose 5-(2-pyrrodinylmethyl)-5,11-dihydrodibenzo[b,e][1,4]oxazepine derivatives as agents for improving the movement of the digestive tracts. In addition, International Patent No. 0040570A1 discloses 5-alkyl-5,11-dihydrodibenzo[b,e][1,4]oxazepine derivatives as agents for improving the movement of the digestive tracts. However, the activity and selectivity of those compounds for the gastrointestinal tracts is not yet satisfactory and they have not yet been used as drugs.

As the social environment is being complicated recently, many people are under great stress and patients suffering from irritable bowel syndrome and having abnormal bowel movement and abdominal pain as the cardinal symptoms are increasing in number. Drugs used for ameliorating such diseases are, for example, a cholinergic blocking drug, laxatives, antidiarrheal drug, drug for intestinal disorders, mucosal paralyzant, agent for regulating gastrointestinal motor functions, agent for regulating autonomic nerves, herb medicine, antianxiety drug, antidepressant drug, sleeping pill, antipsychotic drug, serotonin receptor antagonist and serotonin receptor agonist. However, the clinical effects of those drugs are yet insufficient and they are not always satisfactory because of the side effects. Under these circumstances, the development of a new type of drugs having an excellent effect of improving functional gastrointestinal diseases and free of side effects is desired.

DISCLOSURE OF THE INVENTION

An object of the present invention is to provide new compounds having excellent effect of improving functional gastrointestinal diseases.

Another object of the present invention is to provide a pharmaceutical composition containing the new compound(s).

Still another object of the present invention is to provide intermediates for producing the new compounds.

Antagonists to calcium channels are considered to be effective on diseases caused by an abnormally accelerated contraction of the intestinal tracts such as irritable intestinal syndrome because they have an effect of controlling the contraction of smooth muscles. In fact, it was reported that antagonists to calcium channels such as Nicardipine and Verapamil are effective on irritable intestinal syndrome [Am. J. Gastroenterol., 80, 317 (1985), Gut, 28, 1609 (1987), J. Clin. Psychiatry, 48, 388 (1987), Pharmacol. Ther., 60, 121 (1993)]. However, these antagonists to calcium channels are scarcely clinically used at present because of the main effect of them on the cardiovascular system. Under those circumstances, the inventors made intensive investigations for the purpose of developing antagonists to calcium channels selectively effective on intestinal tracts and having only a low toxicity or, in other words, inert to the cardiovascular system, as therapeutic agents for functional gastrointestinal diseases, particularly irritable bowel syndrome. As a result, the inventors have found that the calcium antagonistic effect of 5,11-dihydrodiaryl[b,e][1,4]oxazepine on the intestinal tracts is improved and also the selectivity for the calcium antagonistic effect on blood vessels is also improved by introducing a halogen atom into at least one of 1-, 2-, 3-, 4-, 6-, 7-, 8- and 9-positions thereof and/or by introducing a cyclic amino group having a specified structure on a terminal aromatic ring.

Namely, the inventors have found that compounds of general formula [I] given below have the antagonistic activity to calcium channels, which is selective for the intestinal tracts and, therefore, they are effective as agents for improving functional gastrointestinal diseases. The present invention has been attained on the basis of this finding.

The compounds of the present invention are useful as remedies for functional gastrointestinal diseases including gastrointestinal motor function diseases, such as irritable bowel syndrome, rumination syndrome, globus syndrome, functional heart burn, functional chest pain of presumed esophageal origin, functional gastrointestinal disorder, functional dysphagia, functional vomiting, deglutition disorder, aerophagia, functional constipation, functional abdominal bloating, functional abdominal pain syndrome, functional diarrhea, sphincter of Oddi's dysfunction, gallbladder dysfunction, levator ani syndrome, functional fecal incontinence, pelvic floor dyssynergia proctalgia fugax and pediatric gastrointestinal function disorders (such as infant regurgitation syndrome, infant rumination syndrome, cyclic vomiting syndrome, functional gastrointestinal disorders, irritable bowel syndrome, functional abdominal pain, paroxysmal abdominal pain, aerophagia, functional diarrhea, infant dyschezia, functional constipation, functional fecal retention and functional non-retentive fecal soiling). The compounds of the present invention are particularly useful for the treatment of irritable bowel syndrome.

The compounds of the present invention are also useful for the treatment of diseases with pathology similar to that of functional gastrointestinal diseases [neuropathies such as anxiety disorders (panic disorder and generalized anxiety disorder), somatoform disorder, dissociated disorder and neuroses such as emotional disorder, bulimia, nervous anorexia, somnipathy, diabetic gastrointestinal disease, etc.]and gastrointestinal symptoms after surgical operation of the abdomen.

The compounds of the present invention are usable for the treatment of the above-described diseases either alone or in combination with a cholinergic blocking drug, laxatives, antidiarrheal drug, drug for intestinal disorders, mucosal paralyzant, agent for regulating gastrointestinal motor functions, agent for regulating autonomic nerves, herb medicine, antianxiety drug, antidepressant drug, sleeping pill, antipsychotic drug, serotonin receptor antagonist and serotonin receptor agonist. The compounds of the present invention are expected not only to have the excellent pharmacological effect but also to be metabolically stable.

Namely, the present invention relates to 5,11-dihydrodiaryl[b,e][1,4]oxazepine derivatives represented by the following general formula [I], stereoisomers thereof, pharmacologically acceptable salts thereof, hydrates or solvates thereof and pharmaceutical compositions containing them as the active ingredient:

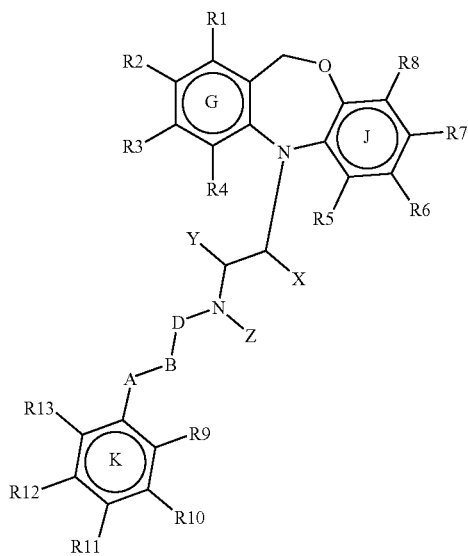

[I]

wherein rings G, J and K each represent benzene ring or a nitrogen-containing aromatic ring; $R^1$ to $R^8$ may be the same or different from one another and they each represent a halogen atom or a hydrogen atom, $R^9$ to $R^{13}$ may be the same or different from one another and they each represent a hydrogen atom, a halogen atom, cyano group, hydroxyl group, a lower alkyl group, a lower alkoxyl group, amino group or a lower alkylamino group or a lower acylated derivative of such a group, a lower dialkylamino group or a cycloalkylamino group, or $R^9$ and $R^{10}$ or $R^{10}$ and $R^{11}$ together form —O(CH$_2$)nO— group wherein n is 1, 2 or 3; A represents CH$_2$, CHOH, CO or O; B represents CH$_2$, CHOH or CO; or A-B represents CH=CH, D represents CH$_2$, CH$_2$—CH$_2$ or CH$_2$—CH$_2$—CH$_2$ or B-D represents CH$_2$; X and Z are bonded together to form CH$_2$—CH$_2$ or CH$_2$—CH$_2$—CH$_2$ and, in this case, Y represents a hydrogen atom; or Y and Z are bonded together to form CH$_2$—CH$_2$—CH$_2$ or CH$_2$—CH$_2$—CH$_2$—CH$_2$ and, in this case, X represents a hydrogen atom; and when X and Z, and Y and Z are not bonded together, X and Y each represent a hydrogen atom and Z represents a lower alkyl group;

provided that when any of $R^9$ to $R^{13}$ represents a cyclic amino group of the following formula [E], $R^1$ to $R^8$ may be a halogen atom or hydrogen atom but when none of $R^9$ to $R^{13}$ is a cyclic amino group of formula [E], one or two of $R^1$ to $R^8$ represent a halogen atom and the others represent a hydrogen atom:

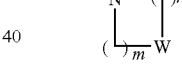

[E]

wherein n and m each represent 1 or 2, and W represents carbon atom, or nitrogen which may be substituted with a lower alkyl group, or oxygen, or sulfur atom.

In the 5,11-dihydrodiaryl[b,e][1,4]oxazepine derivatives, compounds of above general formula [I] wherein X represents a hydrogen atom and Y and Z are bonded together to form CH$_2$—CH$_2$—CH$_2$ or CH$_2$—CH$_2$—CH$_2$—CH$_2$ or X and Y each represent a hydrogen atom and Z represents a lower alkyl group are represented by general formula [XXVI]. The inventors have also found that those compounds [XXVI] can be produced by the intramolecular arylation of a corresponding amide derivative of general formula [XVI] or a salt thereof to obtain a 5,11-dihydrodiaryl[b,e][1,4]oxazepine derivative of general formula [XV] or a salt thereof followed by the reduction of the derivative or the salt. Namely, the present invention also relates to compounds of general formulae [XV] and [XVI], which are important intermediates for producing the compounds of general formula [XXVI], among the compounds of general formula [I], as well as stereoisomers and salts thereof:

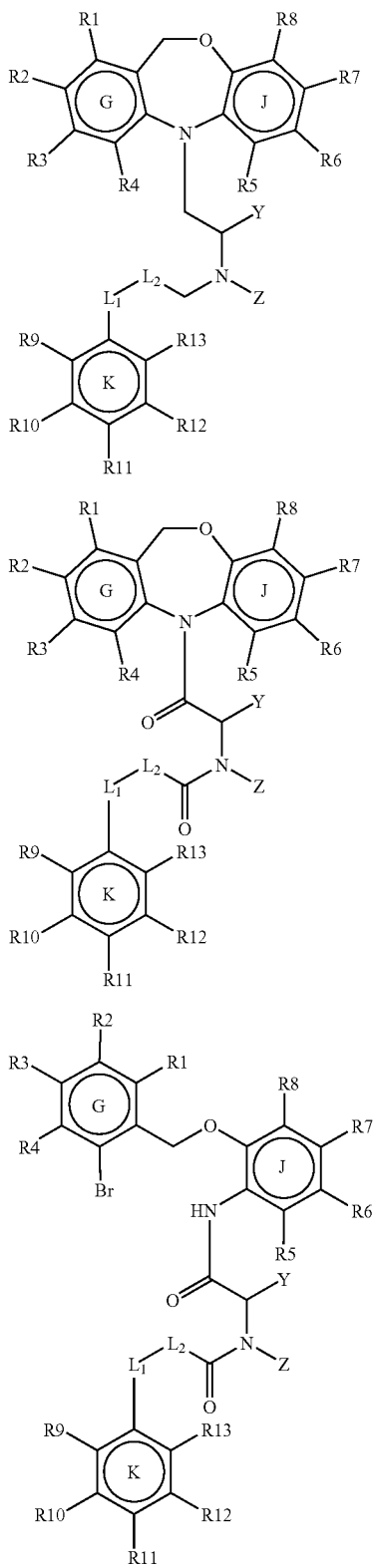

wherein rings G, J and K each represent benzene ring or a nitrogen-containing aromatic ring; $R^1$ to $R^8$ may be the same or different from one another and they each represent a halogen atom or hydrogen atom, $R^9$ to $R^{13}$ may be the same or different from one another and they each represent a hydrogen atom, a halogen atom, cyano group, hydroxyl group, a lower alkyl group, a lower alkoxyl group, amino group or a lower alkylamino group or a lower acylated derivative of such a group, a lower dialkylamino group or a cycloalkylamino group, or $R^9$ and $R^{10}$ or $R^{10}$ and $R^{11}$ together form —O(CH$_2$)nO— group wherein n is 1, 2 or 3; $L_1$ represents CH$_2$, CHOH or O; $L_2$ represents CH$_2$, CHOH, CH$_2$—CH$_2$, CHOH—CH$_2$, CH$_2$—CH$_2$—CH$_2$ or CHOH—CH$_2$—CH$_2$; or $L_1$ and $L_2$ are bonded together to form CH$_2$, CHOH or CH=CH, Y and Z are bonded together to form CH$_2$—CH$_2$—CH$_2$ or CH$_2$—CH$_2$—CH$_2$—CH$_2$ or when Y and Z are not bonded together, Y represents a hydrogen atom and Z represents a lower alkyl group; provided that when any of $R^9$ to $R^{13}$ represents a cyclic amino group of the following formula [E], $R^1$ to $R^8$ may be a halogen atom or hydrogen atom but when none of $R^9$ to $R^{13}$ is a cyclic amino group of formula [E], one or two of $R^1$ to $R^8$ represent a halogen atom and the others represent a hydrogen atom:

[E]

wherein n and m each represent 1 or 2, and W represents carbon atom, or nitrogen which may be substituted with a lower alkyl group, or oxygen, or sulfur atom.

BEST MODE FOR CARRYING OUT THE INVENTION

The nitrogen-containing aromatic rings G, J and K in the above general formula [I] are desirably compounds having a 6-membered ring such as pyridine ring, pyrimidine ring, pyrazine ring or pyridazine ring with the proviso that nitrogen atom constituting an aromatic ring cannot be placed on the oxazepine ring, that when any of $R^1$ to $R^8$ is a halogen atom, this halogen atom is not bonded to the nitrogen atom in the aromatic ring and that, in ring K, the nitrogen atom constituting the aromatic ring is not bonded with A and the nitrogen atom is not bonded with any substituent.

As for rings G, J and K, the following five cases (i) to (v) are preferred: (i) both rings G and J are benzene rings, (ii) one of rings G and J is pyridine ring and the other is benzene ring, (iii) ring K is benzene ring and rings G and J are as described in (i) or (ii), (iv) ring K is pyridine ring, pyrimidine ring, pyrazine ring or pyridazine ring and rings G and J are as described in (i) or (ii), and (v) rings G, J and K are all benzene rings. In general formulae [XV] and [XVI], the above-described five cases (i) to (v) are preferred.

The halogen atoms as $R^1$ to $R^8$ in the above general formula may be fluorine atom, chlorine atom, bromine atom, etc. In them, fluorine atom or chlorine atom is preferred. It is more desirable that one of $R^2$, $R^3$, $R^6$ and $R^7$ in $R^1$ to $R^8$ is fluorine atom or chlorine atom and the others are each a hydrogen atom. In $R^9$ to $R^{13}$, the halogen atoms include fluorine atom, chlorine atom, bromine atom, etc., and the lower alkyl groups include those having 1 to 5 carbon atoms such as methyl group, ethyl group and propyl group, the lower alkoxyl groups include those having 1 to 5 carbon atoms such as methoxyl group, ethoxyl group and propoxyl group, and the lower alkylamino groups are those having 1 to 5 carbon atoms such as monomethylamino group, monoethylamino group and monopropylamino group. The lower acylated derivatives of the amino group and lower alkylamino groups are those acylated with fatty acids having 1 to 3 carbon atoms, such as formylamino group, acetylamino group, propionylamino group, formylmethylamino group, formylethylamino group, formylpropylamino group, acetylmethylamino group, acetylethylamino group, acetylpropylamino group, propionylmethylamino group, propionylethylamino group and propionylpropylamino group. The dialkylamino groups include, for example, lower alkylamino groups having 2 to 7 carbon atoms in total such as dimethylamino group, diethylamino group and methylethylamino group. The cycloalkylamino groups include amino groups having a 4- to 7-membered ring such as azetidino group, pyrrolidino group, piperidino group, homopiperidino group, piperazino group and morpholino group. The —O(CH$_2$)nO— groups include methylenedioxyl group, ethylenedioxyl group and propylenedioxyl group. In those atoms and groups, the halogen atoms are preferably fluorine atom and chloride atom, and the lower alkyl groups are preferably those having 1 to 3 carbon atoms. The lower alkoxyl groups are preferably those having 1 to 3 carbon atoms. The monoalkylamino groups are preferably lower monoalkylamino groups having 1 to 3 carbon atoms. The dialkylamino groups are preferably those wherein the alkyl groups have 2 to 6 carbon atoms in total. The cycloalkylamino groups are preferably those wherein the ring has 4 to 6 members. The acyl groups in the lower acylated derivatives of the amino group and those lower alkylamino groups are preferably formyl group or acetyl group. It is preferred that $R^9$ to $R^{13}$ are not a hydrogen atom at the same time.

In the above general formula [I] and also in general formulae [XV] and [XVI], the following conditions are preferred:

(i) X and Z are bonded together to form CH$_2$—CH$_2$ or CH$_2$—CH$_2$—CH$_2$ and Y represents a hydrogen atom,
(ii) Y and Z are bonded together to form CH$_2$—CH$_2$—CH$_2$ or CH$_2$—CH$_2$—CH$_2$—CH$_2$ and X represents a hydrogen atom,
(iii) X and Y are each a hydrogen atom and Z is a lower alkyl group,
(iv) either or both of $R^{10}$ and $R^{11}$ are methoxyl group or $R^{10}$ and $R^{11}$ together form methylenedioxyl group, and $R^9$, $R^{12}$ and $R^{13}$ are each a hydrogen atom,
(v) $R^{11}$ is methoxyl group, and $R^9$, $R^{10}$, $R^{12}$ and $R^{13}$ are each a hydrogen atom,
(vi) either $R^{10}$ or $R^{11}$ is amino group, a lower alkylamino group, a lower acylated amino group, a lower acylated lower alkylamino group, a lower dialkylamino group or a cycloalkylamino group, and the other is a hydrogen atom,
(vii) all of $R^1$ and $R^8$ are a hydrogen atom,
(viii) one of $R^1$ and $R^8$ is fluorine atom or chlorine atom and the others are each a hydrogen atom,
(ix) one of $R^2$, $R^3$, $R^6$ and $R^7$ is fluorine atom or chlorine atom and others are each a hydrogen atom,
(x) A and B-D are both CH$_2$,
(xi) the carbon atom to which X is bonded has an absolute configuration of R,
(xii) the carbon atom to which X is bonded has an absolute configuration of S,
(xiii) the carbon atom to which Y is bonded has an absolute configuration of R, and
(xiv) the carbon atom to which Y is bonded has an absolute configuration of S, The cyclic amino groups represented by the formula [E] include those having one nitrogen atom such as azetidino group, pyrrolidino group and piperidino group and also those further containing a hetero atom such as nitrogen atom or oxygen atom, such as piperazino group and morpholino group. In those groups, pyrrolidino group and morpholino group are preferred. It is more preferred that in $R^9$ to $R^{13}$, either $R^{10}$ or $R^{11}$ is a cyclic amino group and the other is a hydrogen atom.

A-B-D is preferably CH$_2$—CH$_2$, CO—CH$_2$, CHOH—CH$_2$, CHOH—CH$_2$—CH$_2$, CH$_2$—CHOH—CH$_2$, CH═CH—CH$_2$, CO—CH$_2$—CH$_2$, O—CH$_2$—CH$_2$, CH$_2$—CO—CH$_2$ or CH$_2$—CH$_2$—CH$_2$.

In these compounds, preferred ones are those represented by the following formula [II] wherein G, J, K, $R^1$ to $R^{13}$, A, B and D are the same as those in the above formula [I], and r represents 1 or 2:

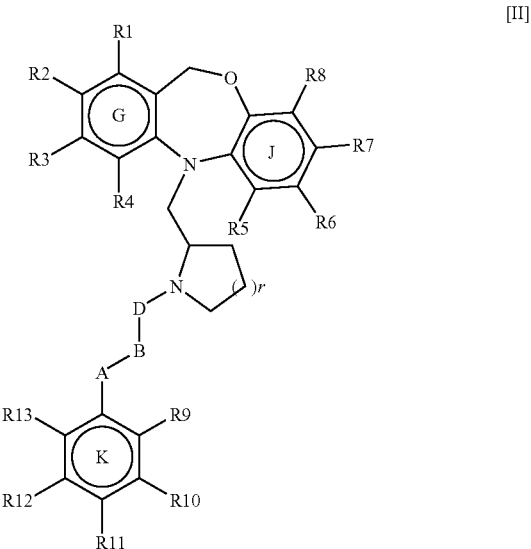

[II]

The compounds of the formula [II] are, for example, 2-fluoro-5,11-dihydro-5-[1-(4-methoxyphenethyl)pyrrolidin-2-ylmethyl]dibenzo[b,e]-[1,4]oxazepine, 2-fluoro-5,11-dihydro-5-[1-(3-methoxyphenethyl)-pyrrolidin-2-ylmethyl] dibenzo[b,e][1,4]oxazepine, 2-fluoro-5,11-dihydro-5-[1-(3,4-methylenedioxyphenethyl)pyrrolidin-2-ylmethyl]dibenzo[b,e]-[1,4]oxazepine, 2-fluoro-5,11-dihydro-5-[1-(4-aminophenethyl)pyrrolidin-2-ylmethyl]dibenzo[b,e][1,4]oxazepine, 2-fluoro-5,11-dihydro-5-[1-(3-aminophenethyl)pyrrolidin-2-ylmethyl]dibenzo[b,e][1,4]oxazepine, 2-fluoro-5,11-dihydro-5-[1-(4-methylaminophenethyl)pyrrolidin-2-ylmethyl]dibenzo[b,e][1,4]oxazepine, 2-fluoro-5,11-dihydro-5-[1-(3-methyl-aminophenethyl)pyrrolidin-2-ylmethyl]dibenzo[b,e][1,4]oxazepine, 2-fluoro-5,11-dihydro-5-[1-(4-dimethylaminophenethyl)pyrrolidin-2-ylmethyl]dibenzo[b,e][1,4]oxazepine, 2-fluoro-5,11-dihydro-5-[1-(3-dimethylaminophenethyl)pyrrolidin-2-ylmethyl]dibenzo[b,e][1,4]oxazepine, 2-fluoro-5,11-dihydro-5-[1-(4-pyrrolidinophenethyl)pyrrolidin-2-ylmethyl]dibenzo[b,e][1,4]oxazepine, 2-fluoro-5,11-dihydro-5-[1-(3-pyrrolidinophenethyl)pyrrolidin-2-ylmethyl]dibenzo[b,e][1,4]oxazepine, 2-fluoro-5,11-dihydro-5-[1-(4-morpholinophenethyl)pyrrolidin-2-ylmethyl]dibenzo[b,e][1,4]oxazepine, 2-fluoro-5,11-dihydro-5-[1-(3-morpholinophenethyl)pyrrolidin-2-ylmethyl]dibenzo[b,e][1,4]oxazepine, 2-fluoro-5,11-dihydro-5-[1-(4-phlorophenethyl)pyrrolidin-2-ylmethyl]

dibenzo[b,e][1,4]oxazepine, 2-fluoro-5,11-dihydro-5-[1-(3-phlorophenethyl)-pyrrolidin-2-ylmethyl]dibenzo[b,e][1,4]oxazepine, 2-fluoro-5,11-dihydro-5-[1-(4-acetylaminophenethyl)pyrrolidin-2-ylmethyl]dibenzo[b,e][1,4]oxazepine, 2-fluoro-5,11-dihydro-5-[1-(3-acetylaminophenethyl)pyrrolidin-2-ylmethyl]dibenzo[b,e][1,4]oxazepine, 3-chloro-5,11-dihydro-5-[1-(4-methoxyphenethyl)pyrrolidin-2-ylmethyl]dibenzo[b,e][1,4]oxazepine, 3-chloro-5,11-dihydro-5-[1-(3-methoxyphenethyl)pyrrolidin-2-ylmethyl]dibenzo[b,e][1,4]oxazepine, 3-chloro-5,11-dihydro-5-[1-(3,4-methylenedioxyphenethyl)pyrrolidin-2-ylmethyl]dibenzo[b,e][1,4]oxazepine, 3-chloro-5,11-dihydro-5-[1-(4-aminophenethyl)pyrrolidin-2-ylmethyl]dibenzo[b,e]-[1,4]oxazepine, 3-chloro-5,11-dihydro-5-[1-(3-aminophenethyl)pyrrolidin-2-ylmethyl]dibenzo[b,e][1,4]oxazepine, 3-chloro-5,11-dihydro-5-[1-(4-methylaminophenethyl)pyrrolidin-2-yl-methyl]dibenzo[b,e][1,4]oxazepine, 3-chloro-5,11-dihydro-5-[1-(3-methylaminophenethyl)pyrrolidin-2-yl-methyl]dibenzo[b,e][1,4]oxazepine, 3-chloro-5,11-dihydro-5-[1-(4-dimethylaminophenethyl)pyrrolidin-2-ylmethyl]dibenzo[b,e][1,4]oxazepine, 3-chloro-5,11-dihydro-5-[1-(3-dimethylamino-phenethyl)pyrrolidin-2-ylmethyl]dibenzo[b,e][1,4]oxazepine, 3-chloro-5,11-dihydro-5-[1-(4-pyrrolidinophenethyl)pyrrolidin-2-ylmethyl]dibenzo-[b,e][1,4]oxazepine, 3-chloro-5,11-dihydro-5-[1-(3-pyrrolidinophenethyl)-pyrrolidin-2-ylmethyl]dibenzo[b,e][1,4]oxazepine, 3-chloro-5,11-dihydro-5-[1-(4-morpholinophenethyl)pyrrolidin-2-ylmethyl]dibenzo[b,e][1,4]oxazepine, 3-chloro-5,11-dihydro-5-[1-(3-morpholinophenethyl)pyrrolidin-2-ylmethyl]dibenzo[b,e][1,4]oxazepine, 3-chloro-5,11-dihydro-5-[1-(4-phlorophenethyl)pyrrolidin-2-ylmethyl]dibenzo[b,e][1,4]oxazepine, 3-chloro-5,11-dihydro-5-[1-(3-phlorophenethyl)pyrrolidin-2-ylmethyl]-dibenzo[b,e][1,4]oxazepine, 3-chloro-5,11-dihydro-5-[1-(4-acetylamino-phenethyl)pyrrolidin-2-yl-methyl]dibenzo[b,e][1,4]oxazepine, 3-chloro-5,11-dihydro-5-[1-(3-acetylamino-phenethyl)pyrrolidin-2-yl-methyl]-dibenzo[b,e][1,4]oxazepine, 5,11-dihydro-5-[1-(4-pyrrolidinophenethyl)pyrrolidin-2-ylmethyl]dibenzo[b,e]-[1,4]oxazepine, 5,11-dihydro-5-[1-(4-pyrrolidinophenethyl)pyrrolidin-2-ylmethyl]dibenzo[b,e][1,4]oxazepine, 5,11-dihydro-5-[1-(4-piperidinophenethyl)pyrrolidin-2-ylmethyl]dibenzo-[b,e][1,4]oxazepine, 5,11-dihydro-5-[1-(3-piperidinophenethyl)pyrrolidin-2-ylmethyl]dibenzo[b,e][1,4]oxazepine, 5,11-dihydro-5-[1-(4-morpholino-phenethyl)pyrrolidin-2-ylmethyl]dibenzo[b,e][1,4]oxazepine, 5,11-dihydro-5-[1-(3-morpholinophenethyl)pyrrolidin-2-ylmethyl]dibenzo-[b,e][1,4]oxazepine, and their isomers having a different position of the halogen substitution, pharmacologically acceptable salts, hydrates and solvates of them.

The compounds [II] of the present invention having one or more asymmetric carbon atoms can be optical isomers. Those optical isomers, mixtures of them and racemic compounds of them are included in the compounds of the present invention. In those compounds, the configuration in the 2-position of pyrrolidine ring or piperidine ring bonded to the dihydrodibenzoxazepine ring through methylene is preferably R.

Other preferred compounds are, for example, those of the following formula [III]:

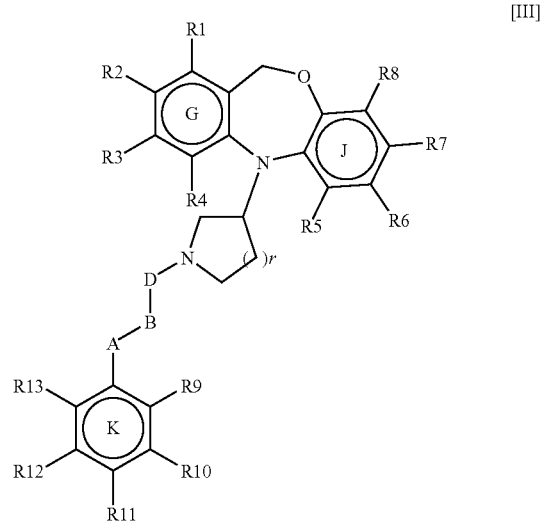

wherein aromatic rings G, J and K, $R^1$ to $R^{13}$, A, B and D are the same as those in the above formula [I], and r represents 1 or 2. The compounds of the formula [III] are, for example, 2-fluoro-5,11-dihydro-5-[1-(4-methoxyphenethyl)-pyrrolidin-3-yl]dibenzo[b,e][1,4]oxazepine, 2-fluoro-5,11-dihydro-5-[1-(3-methoxyphenethyl)pyrrolidin-3-yl]dibenzo[b,e][1,4]oxazepine, 2-fluoro-5,11-dihydro-5-[1-(3,4-methylenedioxyphenethyl)-pyrrolidin-3-yl]dibenzo[b,e][1,4]oxazepine, 2-fluoro-5,11-dihydro-5-[1-(4-aminophenethyl)-pyrrolidin-3-yl]dibenzo[b,e][1,4]oxazepine, 2-fluoro-5,11-dihydro-5-[1-(3-aminophenethyl)pyrrolidin-3-yl]dibenzo[b,e][1,4]oxazepine, 2-fluoro-5,11-dihydro-5-[1-(4-methylaminophenethyl)-pyrrolidin-3-yl]dibenzo[b,e][1,4]oxazepine, 2-fluoro-5,11-dihydro-5-[1-(3-methylaminophenethyl)pyrrolidin-3-yl]dibenzo[b,e][1,4]oxazepine, 2-fluoro-5,11-dihydro-5-[1-(4-dimethylaminophenethyl)-pyrrolidin-3-yl]-dibenzo[b,e][1,4]oxazepine, 2-fluoro-5,11-dihydro-5-[1-(3-dimethylaminophenethyl)-pyrrolidin-3-yl]dibenzo[b,e][1,4]oxazepine, 2-fluoro-5,11-dihydro-5-[1-(4-pyrrolidinophenethyl)pyrrolidin-3-yl]dibenzo[b,e]-[1,4]oxazepine, 2-fluoro-5,11-dihydro-5-[1-(3-pyrrolidinophenethyl)-pyrrolidin-3-yl]di-benzo[b,e][1,4]oxazepine, 2-fluoro-5,11-dihydro-5-[1-(4-morpholinophenethyl)-pyrrolidin-3-yl]dibenzo[b,e][1,4]-oxazepine, 2-fluoro-5,11-dihydro-5-[1-(3-morpholinophenethyl)-pyrrolidin-3-yl]dibenzo-[b,e][1,4]oxazepine, 2-fluoro-5,11-dihydro-5-[1-(4-phlorophenethyl)pyrrolidin-3-yl]dibenzo[b,e][1,4]oxazepine, 2-fluoro-5,11-dihydro-5-[1-(3-phlorophenethyl)-pyrrolidin-3-yl]dibenzo[b,e][1,4]oxazepine, 2-fluoro-5,11-dihydro-5-[1-(4-acetylaminophenethyl)pyrrolidin-3-yl]dibenzo[b,e][1,4]-oxazepine, 2-fluoro-5,11-dihydro-5-[1-(3-acetylaminophenethyl)pyrrolidin-3-yl]dibenzo[b,e][1,4]oxazepine, 3-chloro-5,11-dihydro-5-[1-(4-methoxyphenethyl)pyrrolidin-3-yl]dibenzo[b,e][1,4]oxazepine, 3-chloro-5,11-dihydro-5-[1-(3-methoxyphenethyl)pyrrolidin-3-yl]dibenzo[b,e][1,4]oxazepine, 3-chloro-5,11-dihydro-5-[1-(3,4-methylenedioxyphenethyl)-pyrrolidin-3-yl]dibenzo[b,e][1,4]oxazepine, 3-chloro-5,11-dihydro-5-[1-(4-aminophenethyl)pyrrolidin-3-yl]dibenzo[b,e][1,4]oxazepine, 3-chloro-5,11-dihydro-5-[1-(3-aminophenethyl)pyrrolidin-3-yl]dibenzo[b,e][1,4]oxazepine, 3-chloro-5,11-dihydro-5-[1-(4-methylaminophenethyl)-pyrrolidin-3-yl-]

dibenzo[b,e][1,4]oxazepine, 3-chloro-5,11-dihydro-5-[1-(3-methylaminophenethyl)pyrrolidin-3-yl]dibenzo[b,e][1,4]oxazepine, 3-chloro-5,11-dihydro-5-[1-(4-dimethylaminophenethyl)-pyrrolidin-3-yl]-dibenzo[b,e][1,4]oxazepine, 3-chloro-5,11-dihydro-5-[1-(3-dimethylaminophenethyl)pyrrolidin-3-yl]dibenzo[b,e][1,4]oxazepine, 3-chloro-5,11-dihydro-5-[1-(4-pyrrolidinophenethyl)pyrrolidin-3-yl]dibenzo[b,e][1,4]oxazepine, 3-chloro-5,11-dihydro-5-[1-(3-pyrrolidinophenethyl)pyrrolidin-3-yl]dibenzo[b,e][1,4]oxazepine, 3-chloro-5,11-dihydro-5-[1-(4-morpholinophenethyl)pyrrolidin-3-yl]dibenzo[b,e][1,4]oxazepine, 3-chloro-5,11-dihydro-5-[1-(3-morpholinophenethyl)pyrrolidin-3-yl]dibenzo[b,e][1,4]oxazepine, 3-chloro-5,11-dihydro-5-[1-(4-fluorophenethyl)pyrrolidin-3-yl]dibenzo[b,e][1,4]oxazepine, 3-chloro-5,11-dihydro-5-[1-(3-fluorophenethyl)pyrrolidin-3-yl]dibenzo[b,e][1,4]oxazepine, 3-chloro-5,11-dihydro-5-[1-(4-acetylaminophenethyl)pyrrolidin-3-yl]dibenzo[b,e]-[1,4]oxazepine, 3-chloro-5,11-dihydro-5-[1-(3-acetylaminophenethyl)pyrrolidin-3-yl]dibenzo[b,e][1,4]oxazepine, 5,11-dihydro-5-[1-(4-pyrrolidinophenethyl)pyrrolidin-3-yl]dibenzo[b,e][1,4]oxazepine, 5,11-dihydro-5-[1-(3-pyrrolidinophenethyl)pyrrolidin-3-yl]dibenzo[b,e][1,4]oxazepine, 5,11-dihydro-5-[1-(4-piperidinophenethyl)pyrrolidin-3-yl]-dibenzo[b,e][1,4]oxazepine, 5,11-dihydro-5-[1-(3-piperidinophenethyl)pyrrolidin-3-yl]dibenzo[b,e][1,4]oxazepine, 5,11-dihydro-5-[1-(4-morpholinophenethyl)pyrrolidin-3-yl]dibenzo[b,e][1,4]oxazepine, 5,11-dihydro-5-[1-(3-morpholinophenethyl)pyrrolidin-3-yl]dibenzo[b,e][1,4]oxazepine, and their isomers having a different position of the halogen substitution, pharmacologically acceptable salts, hydrates and solvates of them.

The compounds [III] of the present invention having one or more asymmetric carbon atoms can have optical isomers. Those optical isomers, mixtures of them and racemic compounds of them are included in the compounds of the present invention. In those compounds, the configuration in the 2-position of pyrrolidine ring or piperidine ring bonded to the dihydrodibenzoxazepine ring is preferably R.

Other preferred compounds are, for example, those of the following formula [IV]:

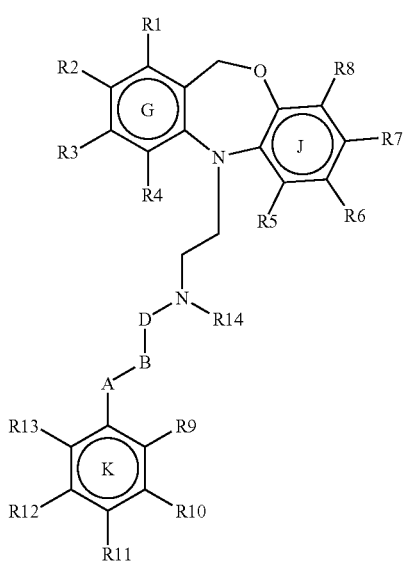

[IV]

wherein aromatic rings G, J and K, $R^1$ to $R^{13}$, A, B and D are the same as those in the above formula [I], and $R^{14}$ represents a lower alkyl group having 1 to 3 carbon atoms.

The compounds of the formula [IV] are, for example, 2-fluoro-5,11-dihydro-5-{2-[N-(4-methoxyphenethyl)-N-methyl]aminoethyl}dibenzo-[b,e][1,4]oxazepine, 2-fluoro-5,11-dihydro-5-{2-[N-(3-methoxyphenethyl)N-methyl] aminoethyl}dibenzo[b,e][1,4]oxazepine, 2-fluoro-5,11-dihydro-5-{2-[N-(3,4-methylenedioxyphenethyl)-N-methyl]aminoethyl}dibenzo[b,e][1,4]oxazepine, 2-fluoro-5,11-dihydro-5-{2-[N-(4-aminophenethyl)-N-methyl] aminoethyl}dibenzo[b,e][1,4]oxazepine, 2-fluoro-5,11-dihydro-5-{2-[N-(3-aminophenethyl)-N-methyl] aminoethyl}dibenzo[b,e][1,4]oxazepine, 2-fluoro-5,11-dihydro-5-{2-[N-(4-methylaminophenethyl)-N-methyl] aminoethyl}dibenzo[b,e][1,4]oxazepine, 2-fluoro-5,11-dihydro-5-{2-[N-(3-methylaminophenethyl)-N-methyl] aminoethyl}dibenzo[b,e][1,4]oxazepine, 2-fluoro-5,11-dihydro-5-{2-[N-(4-dimethylaminophenethyl)-N-methyl] aminoethyl}dibenzo[b,e][1,4]oxazepine, 2-fluoro-5,11-dihydro-5-{2-[N-(3-dimethylaminophenethyl)-N-methyl] aminoethyl}dibenzo[b,e][1,4]oxazepine, 2-fluoro-5,11-dihydro-5-{2-[N-(4-pyrrolidinophenethyl)-N-methyl] aminoethyl}dibenzo[b,e][1,4]oxazepine, 2-fluoro-5,11-dihydro-5-{2-[N-(3-pyrrolidinophenethyl)-N-methyl] aminoethyl}dibenzo[b,e][1,4]oxazepine, 2-fluoro-5,11-dihydro-5-{2-[N-(4-morpholino-phenethyl)-N-methyl] aminoethyl}dibenzo[b,e][1,4]oxazepine, 2-fluoro-5,11-dihydro-5-{2-[N-(3-morpholinophenethyl)-N-methyl] aminoethyl}dibenzo[b,e][1,4]oxazepine, 2-fluoro-5,11-dihydro-5-{2-[N-(4-phlorophenethyl)-N-methyl] aminoethyl}dibenzo[b,e][1,4]oxazepine, 2-fluoro-5,11-dihydro-5-{2-[N-(3-phlorophenethyl)-N-methyl] aminoethyl}dibenzo[b,e][1,4]oxazepine, 2-fluoro-5,11-dihydro-5-{2-[N-(4-acetylaminophenethyl)-N-methyl] aminoethyl}dibenzo[b,e][1,4]oxazepine, 2-fluoro-5,11-dihydro-5-{2-[N-(3-acetylaminophenethyl)-N-methyl] aminoethyl}dibenzo[b,e][1,4]oxazepine, 3-chloro-5,11-dihydro-5-{2-[N-(4-methoxyphenethyl)-N-methyl] aminoethyl}-dibenzo[b,e][1,4]oxazepine, 3-chloro-5,11-dihydro-5-{2-[N-(3-methoxyphenethyl)-N-methyl] aminoethyl}dibenzo[b,e][1,4]oxazepine, 3-chloro-5,11-dihydro-5-{2-[N-(3,4-methylenedioxyphenethyl)-N-methyl]aminoethyl}dibenzo[b,e][1,4]oxazepine, 3-chloro-5,11-dihydro-5-{2-[N-(4-aminophenethyl)-N-methyl] aminoethyl}dibenzo[b,e][1,4]oxazepine, 3-chloro-5,11-dihydro-5-{2-[N-(3-aminophenethyl)-N-methyl] aminoethyl}dibenzo[b,e][1,4]oxazepine, 3-chloro-5,11-dihydro-5-{2-[N-(4-methylaminophenethyl)-N-methyl] aminoethyl}dibenzo[b,e][1,4]oxazepine, 3-chloro-5,11-dihydro-5-{2-[N-(3-methylaminophenethyl)-N-methyl] aminoethyl}dibenzo[b,e][1,4]-oxazepine, 3-chloro-5,11-dihydro-5-{2-[N-(4-dimethylaminophenethyl)-N-methyl] aminoethyl}dibenzo[b,e][1,4]oxazepine, 3-chloro-5,11-dihydro-5-{2-[N-(3-dimethylaminophenethyl)-N-methyl] aminoethyl}dibenzo[b,e][1,4]oxazepine, 3-chloro-5,11-dihydro-5-{2-[N-(4-pyrrolidinophenethyl)-N-methyl] aminoethyl}dibenzo[b,e][1,4]oxazepine, 3-chloro-5,11-dihydro-5-{2-[N-(3-pyrrolidinophenethyl)-N-methyl] aminoethyl}dibenzo[b,e][1,4]oxazepine, 3-chloro-5,11-dihydro-5-{2-[N-(4-morpholinophenethyl)-N-methyl] aminoethyl}dibenzo[b,e][1,4]-oxazepine, 3-chloro-5,11-dihydro-5-{2-[N-(3-morpholinophenethyl)-N-methyl] aminoethyl}dibenzo[b,e][1,4]oxazepine, 3-chloro-5,11-dihydro-5-{2-[N-(4-phlorophenethyl)-N-methyl] aminoethyl}dibenzo[b,e][1,4]-oxazepine, 3-chloro-5,11-dihydro-5-{2-[N-(3-phlorophenethyl)-N-methyl]- aminoethyl}dibenzo[b,e][1,4]oxazepine, 3-chloro-5,11-dihydro-5-{2-[N-(4-acetylaminophenethyl)-N-methyl] aminoethyl}dibenzo[b,e][1,4]oxazepine, 3-chloro-5,11- dihydro-5-{2-[N-(3-acetylaminophenethyl)-N-methyl]aminoethyl}dibenzo[b,e][1,4]oxazepine, 5,11-dihydro-5-{2-[N-methyl-N-(4-pyrrolidinophenethyl)]aminoethyl}dibenzo[b,e][1,4]oxazepine, 5,11-dihydro-5-{2-[N-methyl-N-(3-pyrrolidinophenethyl)]aminoethyl}dibenzo[b,e][1,4]oxazepine, 5,11-dihydro-5-{2-[N-methyl-N-(4-pipelidinophenethyl)]aminoethyl}dibenzo[b,e][1,4]oxazepine, 5,11-dihydro-5-{2-[N-methyl-N-(3-piperidinophenethyl)]aminoethyl}dibenzo[b,e][1,4]oxazepine, 5,11-dihydro-5-{2-[N-methyl-N-(4-morpholinophenethyl)]aminoethyl}dibenzo[b,e][1,4]oxazepine, 5,11-dihydro-5-{2-[N-methyl-N-(3-morpholinophenethyl)]aminoethyl}dibenzo[b,e][1,4]oxazepine, and their isomers having a different position of the halogen substitution, pharmacologically acceptable salts, hydrates and solvates of them.

In the present invention, preferred derivatives are (i) derivatives of the formula [I] wherein one of $R^9$ to $R^{13}$ is a cyclic amino group of formula [E] and the others are each a hydrogen atom and $R^1$ to $R^8$ are each a hydrogen atom, (ii) derivatives of the formula [I] wherein one of $R^9$ to $R^{13}$ is a cyclic amino group of formula [E] and the others are each a hydrogen atom and one or two of $R^1$ to $R^8$ are a hydrogen atom or chlorine atom and (iii) derivatives of the formula [I] wherein all of $R^9$ to $R^{13}$ are a group other than the cyclic amino group of formula [E] and one or two of $R^1$ to $R^8$ are a hydrogen atom or chlorine atom and the others are each a hydrogen atom.

In general formulae [XV] and [XVI], preferably (i) $R^1$ to $R^8$ may be the same or different from each other and they each represent fluorine atom, chlorine atom or a hydrogen atom, $L_1$—$L_2$ represents $CH_2$ or $CH_2$—$CH_2$, Y and Z are bonded together to form $CH_2$—$CH_2$—$CH_2$ or $CH_2$—$CH_2$—$CH_2$—$CH_2$, and/or (ii) $R^9$ to $R^{13}$ may be the same or different from each other and they each represent a hydrogen atom, amino group, a lower alkylamino group, lower acylated amino group, a lower acylated alkylamino group, a lower dialkylamino group or a cycloalkylamino group.

Concretely, preferred compounds are (R)-{[2-(3-chloro-5,11-dihydrodibenzo[b,e][1,4]oxazepine-5-carbonyl)pyrrolidine]-1-yl}-2-(4-dimethylaminophenyl)ethanone, (R)-1-[(4-dimethylaminophenyl)acetyl]pyrrolidine-2-carboxylic acid [2-(2-bromo-4-chlorobenzyloxy)phenyl]amide, (R)-{[2-(2-fluoro-5,11-dihydrodibenzo[b,e][1,4]oxazepine-5-carbonyl)pyrrolidine]-1-yl}-2-(4-pyrrolidinophenyl)ethanone, (R)-1-[(4-pyrrolidinophenyl)acetyl]pyrrolidine-2-carboxylic acid [2-(2-bromo-5-fluorobenzyloxy)phenyl]amide, and stereoisomers and salts thereof.

The pharmacologically acceptable salts of the compounds [I] of the present invention are, for example, mineral acid salts (inorganic salts) such as hydrochlorides, hydrobromides, sulfates and phosphates, and organic acid salts such as acetates, lactates, fumarates, maleates, malates, tartrates, citrates, oxalates, aspartates and methanesulfonates.

In the compounds [I] of the present invention, those represented by the formula [III] can be produced by, for example, the following process (reaction formula 1) disclosed in International Patent No. 9733885A1:

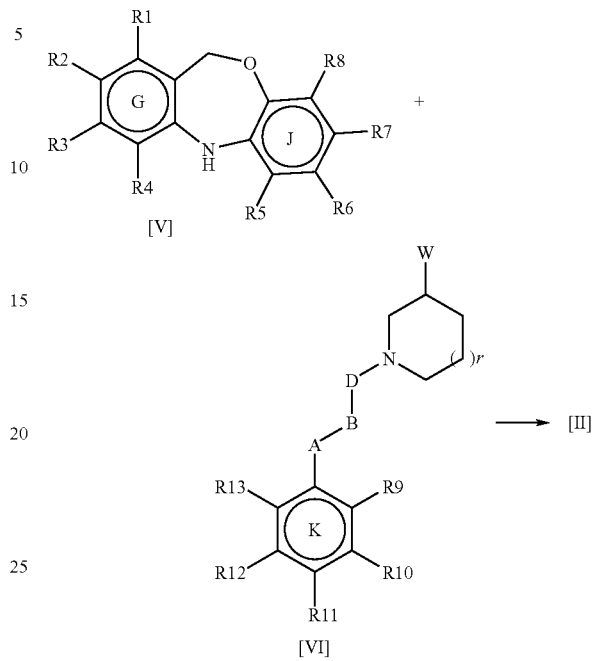

reaction formula 1 wherein aromatic rings G, J and K, $R^1$ to $R^{13}$, A, B and D are the same as those in the above formula [I], r represents 1 or 2, and W represents a halogen atom such as chlorine atom, bromine atom or iodine atom.

The compounds [II] of the present invention can be produced by reacting a compound [V] with a compound of the above general formula [VI] in the presence of a base in a solvent. The preferred solvents for the reaction are, for example, dimethyl sulfoxide, amides such as N,N-dimethylformamide, ethers such as tetrahydrofuran, diethyl ether, dioxane and 1,2-dimethoxyethane, acetonitrile, toluene, xylene and benzene. The bases are, for example, sodium carbonate, potassium carbonate, sodium hydride, potassium hydride, lithium diisopropylamide, n-butyllithium, sodium methoxide and potassium t-butoxide. The reaction temperature is in the range of usually 0 to 150° C., preferably room temperature to 100° C. The reaction time which varies depending on the reaction temperature or variety of the solvent is usually 1 to 50 hours. The amount of the compound [VI] and the base is 0.5 to 5 molar equivalents, preferably 0.8 to 2 molar equivalents, per molar equivalent of the compound [V], respectively.

The compounds [V] used as the starting material in the above-described reaction can be produced by a well-known process [J. Med. Chem., 7, 609 (1964)].

The halides represented by the above general formula [VI] can be produced by a method disclosed in European Patent No. 0404359A1, which comprises the steps of reducing proline or homoproline used as the stating material to obtain an alcohol, N-alkylating the alcohol and then halogenating the hydroxyl group of the compound with ring expansion using methanesulfonyl chloride, tosyl chloride or the like.

The compounds [II] of the present invention can be produced by, for example, the following process (reaction formula 2) disclosed in International Patent No. 9912925A1:

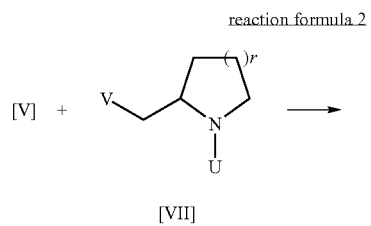

[VII]

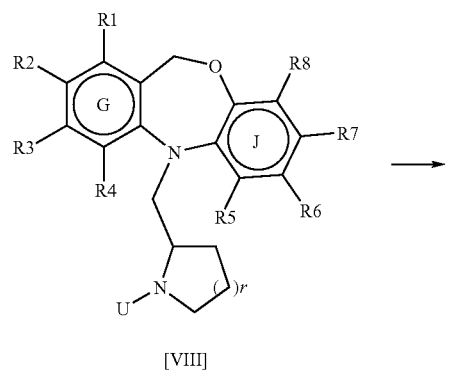

[VIII]

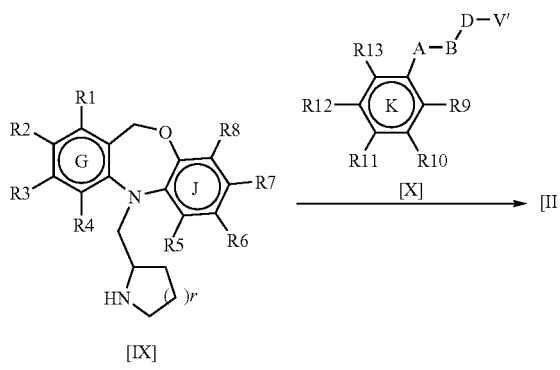

wherein aromatic rings G, J and K, $R^1$ to $R^{13}$, A, B and D are the same as those in the above formula [I], r represents 1 or 2, V and V' each represent chlorine atom, bromine atom, iodine atom or a leaving group such as tosyloxyl group or mesyloxyl group and U represents a protecting group for the amino group such as t-butyloxycarbonyl group, benzyloxycarbonyl group and tosyl group.

The compounds [II] of the present invention can be produced by adding, for example, N-t-butoxycarbonyl-2-piperidylmethyl tosylate of the above general formula [VII] dropwise to a compound [V] in the presence of a base to carry out the invention, removing the protecting group from the obtained compound of the general formula [VIII] to obtain a compound of the general formula [IX], and then reacting this compound with a compound of the general formula [X] in the presence of a base. The solvents and bases used for the reactions for obtaining [VIII] from [V] and also for obtaining [II] from [IX] can be those used for the reaction of the above formula 1.

In the compounds [I] of the present invention, those represented by the formula [III] can be produced by, for example, the following process (reaction formula 3) disclosed in International Patent No. 0040570A1:

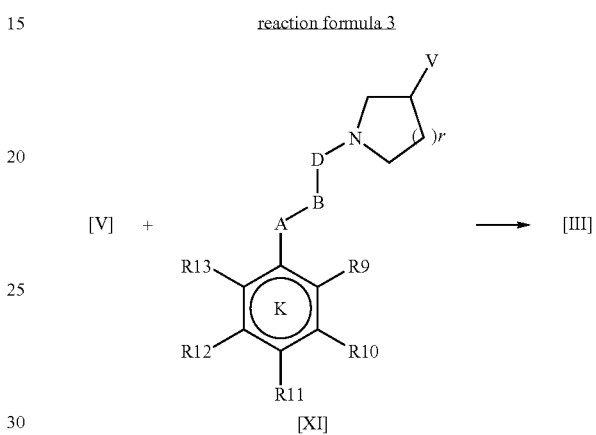

wherein aromatic ring K, $R^9$ to $R^{13}$, A, B, D, V and r are the same as those in the above reaction formula 2.

The compounds [III] of the present invention can be produced by reacting a compound [V] with a compound of the above general formula [XI] in the presence of a base in a solvent. The preferred solvents for the reaction are, for example, dimethyl sulfoxide, amides such as N,N-dimethylformamide, ethers such as tetrahydrofuran, diethyl ether, dioxane and 1,2-dimethoxyethane, acetonitrile, toluene, xylene and benzene. The bases are, for example, sodium hydride, potassium hydride, lithium diisopropylamide, n-butyllithium, sodium methoxide and potassium t-butoxide. The reaction temperature is in the range of usually 0 to 150° C., preferably room temperature to 100° C. The reaction time which varies depending on the reaction temperature or variety of the solvent is usually 1 to 50 hours. The amount of the compound [XI] and the base is 0.5 to 10 molar equivalents, preferably 0.8 to 5 molar equivalents, per molar equivalent of the compound [V], respectively.

The compounds of the general formula [XI] can be obtained by N-alkylating 3-hydroxypyrrolidine or 3-hydroxypiperidine and then reacting the obtained product with phosphorus oxychloride, thionyl chloride, tosyl chloride, methanesulfonyl chloride or the like.

In the compounds [I] of the present invention, those represented by the formula [IV] can be produced by, for example, the following process (reaction formula 4) disclosed in International Patent No. 0040570A1:

reaction formula 4

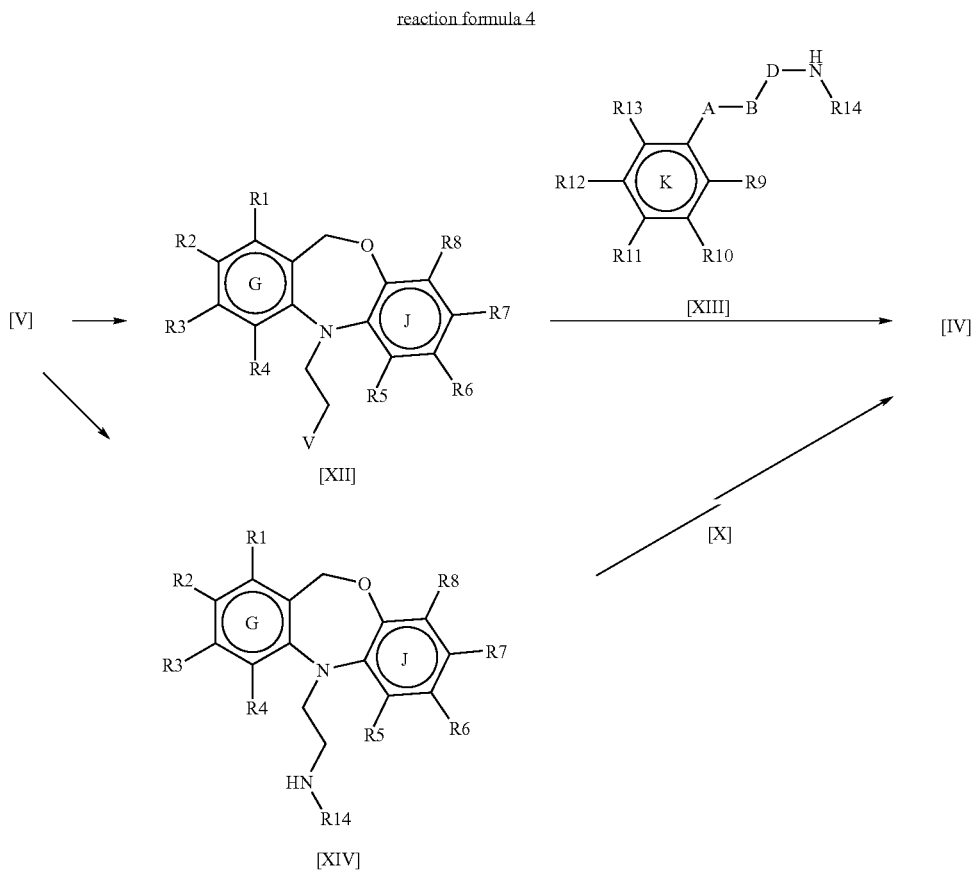

wherein aromatic rings G, J and K, $R^1$ to $R^{13}$, A, B, D and V are the same as those described above and $R^{14}$ represents a lower alkyl group.

Namely, the compounds [IV] of the present invention can be produced by converting a compound [V] into a compound of the above general formula [XII] and then this compound is reacted with a compound of the above general formula [XIII] in the presence of a base. The preferred solvents for the reaction are, for example, dimethyl sulfoxide, amides such as N,N-dimethylformamide, ethers such as tetrahydrofuran, diethyl ether, dioxane and 1,2-dimethoxyethane, acetonitrile, toluene, xylene and benzene. The bases are, for example, sodium carbonate, potassium carbonate, sodium hydride, potassium hydride, lithium diiusopropylamide, n-butyllithium, sodium methoxide and potassium t-butoxide. The reaction temperature is in the range of usually 0 to 150° C., preferably room temperature to 100° C. The reaction time which varies depending on the reaction temperature or variety of the solvent is usually 1 to 50 hours. The amount of the base is at least 1 mole, preferably 1 to 5 moles per mole of the compound [XII]. The amount of the compound [XII] is 0.5 to 2 moles, preferably 0.7 to 1.5 moles, per mole of the compound [XIII].

The compounds [IV] of the present invention can be produced by converting a compound [V] into a compound of the above general formula [XIV] and then condensing the obtained compound with a compound [X] in the presence of a base. In the condensation reaction, the solvent, base, reaction temperature and reaction time may be the same as those described above. The amount of the base used is at least 1 mole, preferably 1 to 5 moles per mole of the compound [XIV]. The amount of the compound [XIV] is 0.5 to 2 moles, preferably 0.7 to 1.5 moles, per mole of the compound [X].

The compounds [XII] can be easily produced by combining known methods. For example, the compounds [XII] can be produced by alkylating the compound [V] with an α-haloacetic acid ester, reducing the obtained compound to form an alcohol and then converting the hydroxyl group thereof into a leaving group, or by alkylating the compound [V] with a 2-haloethanol wherein the hydroxyl group is protected, removing the protecting group and converting the hydroxyl group into a leaving group. The compounds [XIII] can be easily produced by various known processes such as the alkylation reaction of the primary amine with a corresponding halide, the reduction alkylation reaction of a primary amine with a corresponding aldehyde or the acylation of an amine with a corresponding carboxylic acid followed by the reduction as disclosed in International Patent No. 0040570A1.

Compounds [XIV] can be easily produced by various known processes such as the alkylation of the compound [V] with a haloacetic acid ester followed by the amidation and reduction as disclosed in International Patent No. 0040570A1.

In addition to the above-described processes, compounds represented by the formula [II] or [IV] in the compounds [I] of the present invention can be produced via compounds represented by formulae [XVI] and [XV] given below by methods similar to those disclosed in International Patent No. 0117980A1. Namely, when a compound of the formula [II] is represented by the formula [II-1] and a compound of the formula [IV] is represented by the formula [IV-1], each of them can be obtained through a corresponding intermediate by the intramolecular arylation of a compound of the following formula [XVI] to form a compound of the formula [XV], followed by the reduction of the obtained compound according to the following reaction formula 5.

monia complex, borane/tert-butylamine complex, borane/N,N-diethylaniline complex, borane/N,N-diisopropylethylamine complex, borane/dimethylamine complex, borane/4-(dimethylamino)pyridine complex, borane diphenylphosphine complex, borane/4-ethylmorpholine complex, borane/2,6-lutidine complex, borane/4-methylmorpholine complex, borane/dimethyl sulfide complex, borane/morpholine complex, borane/1,4-oxathiane com-

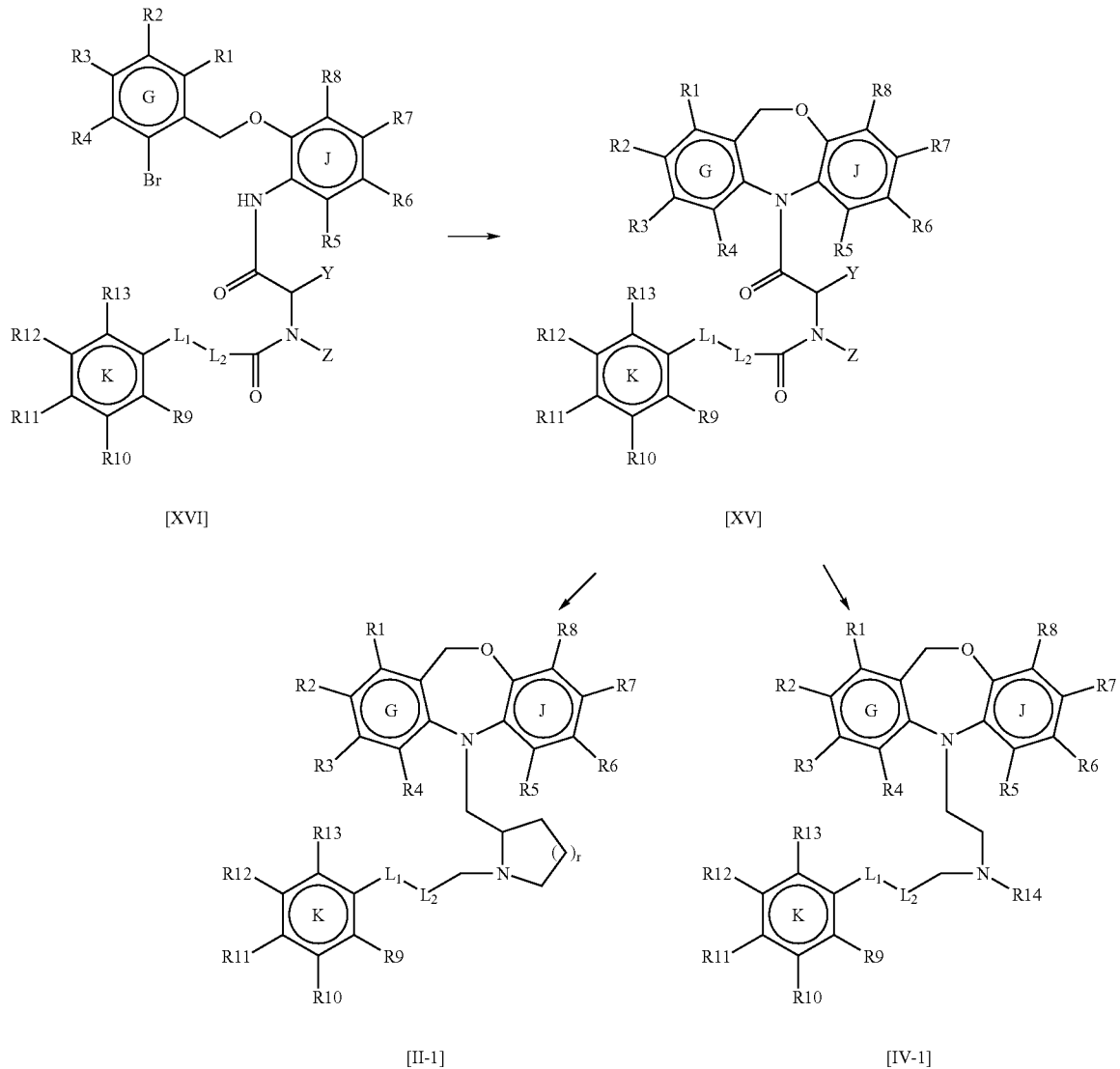

wherein aromatic rings G,J and K, $R^1$ to $R^{14}$, $L_1$ and $L_2$ are as defined in the formula [XV], r represents 1 or 2, Y and Z are bonded together to form $CH_2$—$CH_2$—$CH_2$ or $CH_2$—$CH_2$—$CH_2$—$CH_2$, or when Y and Z are not bonded together, Y represents a hydrogen atom and Z represents a lower alkyl group.

The solvents used in the reduction reaction include ethers such as diethyl ether, dioxane, tetrahydrofuran and 1,2-dimethoxyethane. The solvents may contain 0 to 50% of benzene, toluene, xylene, etc. The reducing agents are, for example, borane compounds such as diborane, borane/amplex, borane/4-phenylmorpholine complex, borane/pyridine complex, borane/tetrahydrofuran complex, borane tributylphosphine complex, borane/triethylamine complex, borane/trimethylamine complex and borane/triphenylphosphine complex; metal hydrides such as aluminum lithium hydride, sodium borohydride and lithium borohydride; as well as those compounds further substituted with an alkyl, alkoxyl or acyl group. A reducing agent may be prepared by adding an acid or the like to the above-described metal halide in the reaction vessel. The acids usable herein include, for example, Brønsted acids such as hydrochloric acid, sulfuric acid, methanesulfonic acid, benzenesulfonic acid, p-toluenesulfonic acid, camphor sulfonic acid, acetic acid and trifluoroacetic acid; Lewis acids such as boron trifluoride, boron trichloride and aluminum trichloride as well as complexes thereof. A process wherein, for example, diborane or borane tetrahydrofuran complex is selectively used in the above-described reducing agents, or a process wherein methanesulfonic acid, boron trifluoride, a complex thereof or the like is added to sodium borohydride to prepare the reducing agent in the reactor is preferred. The reaction temperature that varies depending on the boiling point of the solvent is usually in the range of usually 5 to 100° C., preferably 30 to 60° C. The reaction time that varies depending on the variety of the reducing agent, reaction temperature or variety of the solvent is usually 4 to 70 hours. The amount of the reducing agent, which varies depending on the variety thereof, is such that the amount of the hydride that can be formed will be at least 4 moles, preferably at least 7 moles per mole of the same. The compounds [II-1] to compounds [IV-1] obtained by the reaction can be purified by the silica gel column chromatography, crystallization or the like. Further, the compounds [II-1] to compounds [IV-1] can be crystallized in the form of a salt thereof with a suitable acid. The salts of these compounds with a suitable acid are mineral acid salts (inorganic salts) of them such as hydrochlorides, hydrobromides, sulfates and phosphates, and organic acid salts of them such as acetates, lactates, fumarates, maleates, malates, tartrates, citrates, oxalates, aspartates and methanesulfonates.

The compounds [XV] used as the starting materials in the reduction reaction can be produced by the intramolecular arylation of the compounds [XVI] in the presence of a base and a metallic catalyst. The solvents for the reaction are, for example, unsubstituted and substituted benzene, unsubstituted and substituted pyridine, and amides such as N,N-dimethylformamide, N,N-dimethylacetamide and N-methylpyrrolidone. In those reaction solvents, for example, toluene, pyridine, picoline and N-methylpyrrolidone are preferably usable. The bases are, for example, carbonates such as lithium carbonate, sodium carbonate, potassium carbonate, calcium carbonate and cesium carbonate; metal alkoxides such as sodium methoxide, sodium t-butoxide and potassium t-butoxide; and amines such as trimethylamine, triethylamine, diisopropylethylamine and N-methylmorpholine. In those bases, for example, sodium carbonate, potassium carbonate and cesium carbonate are preferably used. The metallic catalysts include copper catalysts such as copper, copper (I) chloride, copper (I) bromide and copper (I) iodide; palladium catalysts such as palladium, palladium chloride, palladium acetate and tetrakis(triphenylphosphine) palladium, and complexes of them; platinum catalysts such as platinum and platinum chloride and complexes of them. In those metal catalysts, for example, copper and copper (I) bromide are preferably used. The metal catalysts may also be prepared in the reactor. The reaction temperature that varies depending on the boiling point of the solvent is usually in the range of room temperature to 200° C., preferably 100 to 150° C. The reaction time that varies depending on the varieties of the base and metallic catalyst, reaction temperature or variety of the solvent is usually 8 to 200 hours. The amount of the base, that varies depending on the variety thereof, is usually 1 to 10 moles, preferably 1 to 4 moles, per mole of the compound. The amount of the metallic catalyst, that varies depending on the variety thereof, is usually 0.001 to 1 mole, preferably 0.005 to 0.2 mole, per mole of the compound. The compounds [XV] obtained by the reaction can be purified by the extraction from the reaction mixture, the silica gel column chromatography, crystallization or the like before the subsequent reaction or, on the contrary, they can be subjected to the subsequent reaction as they are. Further, the compounds [XV] can be obtained in the form of a salt thereof with a suitable acid. The salts of these compounds with a suitable acid are mineral acid salts (inorganic salts) of them such as hydrochlorides, hydrobromides, sulfates, phosphates and nitrates, and organic acid salts of them such as acetates, lactates, fumarates, maleates, malates, tartrates, citrates, oxalates, aspartates and methanesulfonates.

The compounds [XVI] used as the starting materials for the above-described intramolecular arylation reaction can be produced by the following process (reaction formula 6):

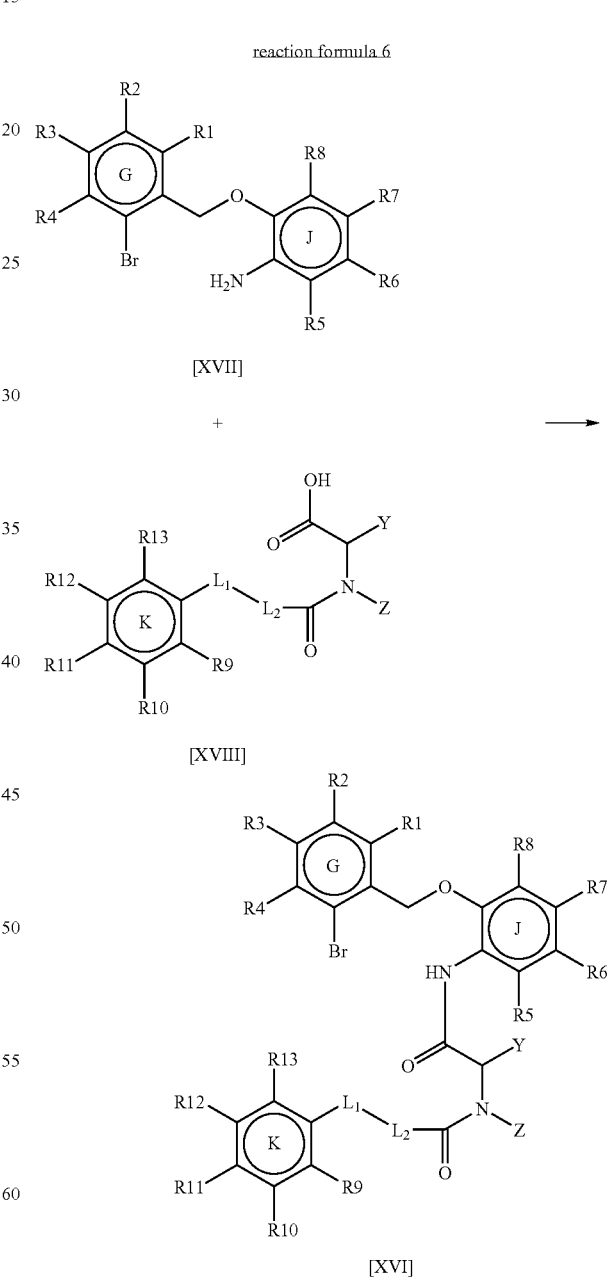

wherein aromatic rings G, J and K, $R^1$ to $R^{13}$, $L_1$ and $L_2$ are as defined in the formula [XVI], Y and Z are bonded together to form $CH_2$—$CH_2$—$CH_2$ or $CH_2$—$CH_2$—$CH_2$—$CH_2$, or when Y and Z are not bonded together, Y represents a hydrogen atom and Z represents a lower alkyl group.

Namely, compounds [XVI] can be produced by condensing a compound [XVII] with a compound [XVIII]. The condensation reaction process can be selected from known processes such as an amidation reaction wherein N,N'-dicyclohexylcarbodiimide or N-dimethylaminopropyl-N'-ethylcarbodiimide or a salt thereof is used, an acid anhydride process wherein a compound [XVIII] is converted into a corresponding acid anhydride prior to the condensation, and a process wherein the product is obtained via a corresponding acid chloride or acid bromide of the compound [XVIII]. The compound [XVI] obtained by the reaction can be extracted from the reaction mixture and purified by the silica gel column chromatography, crystallization or the like before the subsequent reaction or, on the contrary, it can be directly subjected to the subsequent reaction. Further, the compounds [XVI] can be obtained in the form of a salt thereof with a suitable acid. The salts of these compounds with a suitable acid are mineral acid salts (inorganic salts) of them such as hydrochlorides, hydrobromides, sulfates, phosphates and nitrates, and organic acid salts of them such as acetates, lactates, fumarates, maleates, malates, tartrates, citrates, oxalates, aspartates and methanesulfonates.

The compounds [XVII] used as the starting materials for the above-described reaction 6 can be produced by a known method [J. Med. Chem., 7, 609 (1964)].

The compounds [XVIII] can be produced by the following process (reaction formula 7):

wherein aromatic ring K, $R^9$ to $R^{13}$, $L_1$ and $L_2$ are as defined above, Y and Z are bonded together to form $CH_2$—$CH_2$—$CH_2$ or $CH_2$—$CH_2$—$CH_2$—$CH_2$, or when Y and Z are not bonded together, Y represents a hydrogen atom and Z represents a lower alkyl group.

Namely, compounds [XVIII] can be produced by condensing a compound [XIX] with a compound [XX]. The condensation reaction can be selected from known processes such as an amidation reaction wherein N,N'-dicyclohexylcarbodiimide or N-dimethylaminopropyl-N'-ethylcarbodiimide or a salt thereof is used, an acid anhydride process wherein a compound [XIX] is converted into a corresponding acid anhydride prior to the condensation, and a process wherein the product is obtained via a corresponding acid chloride or acid bromide of the compound [XIX]. The compound [XVIII] obtained by the reaction can be extracted from the reaction mixture and purified by the silica gel column chromatography, crystallization or the like before the subsequent reaction or, on the contrary, it can be directly subjected to the subsequent reaction. Further, the compounds [XVIII] can be produced by protecting the carboxylic acid part of the compound [XX] with a suitable protecting group and then removing the protecting group after the above-described condensation reaction with the compound [XIX]. The suitable protecting groups used herein are esters with methyl, ethyl, n-propyl, isopropyl, n-butyl, isobutyl, tert-butyl and substituted groups thereof, and silyl esters with trimethylsilyl, triethylsilyl and tert-butyldimethylsilyl groups.

In the compounds [I] of the present invention, those represented by the formula [III] can be produced by the following process (reaction formula 8):

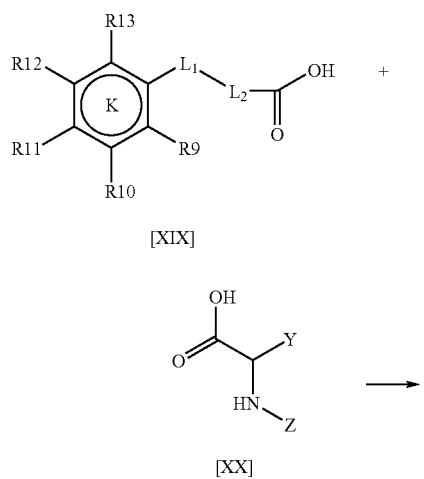

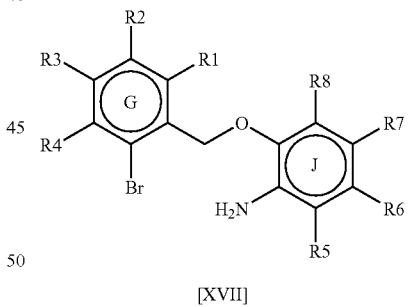

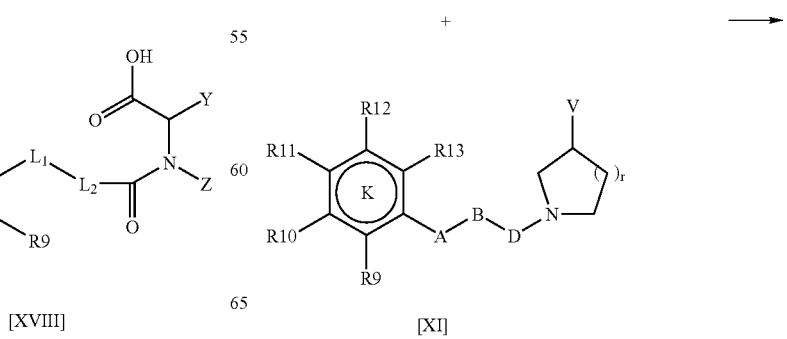

-continued

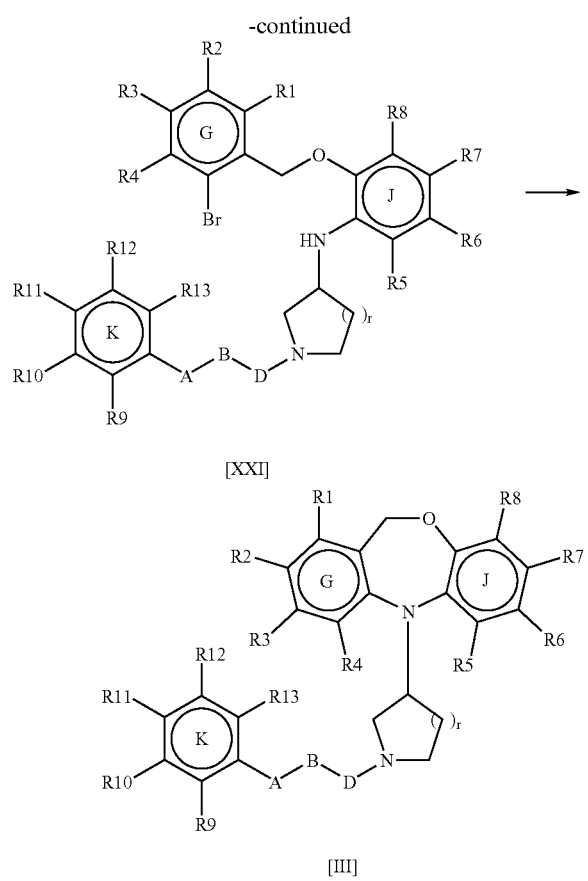

wherein aromatic rings G, J and K, $R^1$ to $R^{13}$, A, B, D, V and r are as defined above.

The compounds [III] can be produced by the intramolecular arylation of the compounds [XXI] in the presence of a base and a metallic catalyst. The solvents for the reaction are, for example, unsubstituted and substituted benzene, unsubstituted and substituted pyridine, and amides such as N,N-dimethylformamide, N,N-dimethylacetamide and N-methylpyrrolidone. The bases are, for example, carbonates such as lithium carbonate, sodium carbonate, potassium carbonate, calcium carbonate and cesium carbonate; metal alkoxides such as sodium methoxide, sodium t-butoxide and potassium t-butoxide; and amines such as trimethylamine, triethylamine, diisopropylethylamine and N-methylmorpholine. The metallic catalysts include copper catalysts such as copper, copper (I) chloride, copper (I) bromide and copper (I) iodide; palladium catalysts such as palladium, palladium chloride, palladium acetate and tetrakis(triphenylphosphine) palladium, and complexes of them; platinum catalysts such as platinum and platinum chloride and complexes of them. The metal catalysts may also be prepared in the reactor. The reaction temperature that varies depending on the boiling point of the solvent is usually in the range of room temperature to 200° C., preferably 80 to 160° C. The reaction time that varies depending on the varieties of the base and metallic catalyst, reaction temperature or variety of the solvent is usually 5 to 150 hours. The amount of the base, that varies depending on the variety thereof, is usually 1 to 20 moles, preferably 1.5 to 8 moles, per mole of the compound. The amount of the metallic catalyst, that varies depending on the variety thereof, is usually 0.001 to 1 mole, preferably 0.005 to 0.3 mole, per mole of the compound. The compounds [III] obtained by the reaction can be purified by the extraction from the reaction mixture, the silica gel column chromatography, high performance liquid chromatography, crystallization or the like. Further, the compounds [III] can be crystallized in the form of a salt thereof with a suitable acid. The salts of these compounds with a suitable acid are mineral acid salts (inorganic salts) of them such as hydrochlorides, hydrobromides, sulfates, phosphates and nitrates, and organic acid salts of them such as acetates, lactates, fumarates, maleates, malates, tartrates, citrates, oxalates, aspartates and methanesulfonates.

The compounds [XXI] used as the starting material for the intramolecular arylation reaction can be produced by alkylating the amino group of compound [XVII] with compound [XI]. The alkylation reaction is carried out, for example, in the presence of a base. Namely, the compounds [XXI] can be produced by reacting compound [XVII] with compound [XI] in the presence of a base in a suitable solvent. The bases are, for example, carbonates such as lithium carbonate, sodium carbonate, potassium carbonate, calcium carbonate and cesium carbonate, metal alkoxides such as sodium methoxide, sodium t-butoxide and potassium t-butoxide, and amines such as trimethylamine, triethylamine, diisopropylethylamine and N-methylmorpholine. The compounds [XXI] obtained by the reaction can be extracted from the reaction mixture and purified by the silica gel column chromatography or the like before the subsequent reaction or, on the contrary, it can be directly subjected to the subsequent reaction.

When the compounds of the present invention are used in the form of a pharmaceutical preparation or a pharmaceutical composition, they can be suitably mixed with pharmaceutical assistants such as pharmacologically acceptable excipient, carrier and diluent and orally or parenterally administered in the dosage form of tablets, capsules, granules, fine granules, powders, pills, syrups, suspensions, emulsions, ointments, suppositories or parenteral solution. In the present invention, a pharmaceutical preparation or a pharmaceutical composition containing one of the compounds of the present invention as the active ingredient, a pharmacologically acceptable carrier and/or diluent is preferred. The carriers and diluents are, for example, glucose, sucrose, lactose, talc, silica, cellulose, methylcellulose, starch, gelatin, ethylene glycol, polyethylene glycol, glycerol, ethanol, water, oils and fats.

The dose and dosing frequency of the compounds of the present invention can be suitably selected depending on the kind of the disease, age and body weight of the patient, etc. For example, when a compound of the present invention is to be orally administered to an adult patient as a therapeutic agent for intestinal diseases such as irritable bowel syndrome, about 0.1 to 1,000 mg/day of the compound is given once or in several portions.

EXAMPLES

The following Examples, Test Examples and Preparation Examples will further illustrate the present invention, which by no means limit the invention.

Example 1

(R)-3-Fluoro-5,11-dihydro-5-[1-(4-methoxyphenethyl)pyrrolidin-2-yl-methyl]dibenzo[b,e][1,4]oxazepine hydrochloride (R)-3-Fluoro-5,11-dihydro-5-[1-(4-methoxyphenethyl) pyrrolidin-2-yl-methyl]dibenzo[b,e][1,4]oxazepine:

60% sodium hydride (44 mg, 1.1 mmol) was washed with hexane in argon stream and then suspended in dimethyl sulfoxide (5 ml), and the obtained suspension was stirred at room temperature for 30 minutes. 3-Fluoro-5,11-dihydrodibenzo[b,e][1,4]oxazepine (0.22 g, 1.0 mmol) was added to the suspension, and they were stirred at room temperature for 30 minutes and then at 50° C. for additional 30 minutes. A solution of (R)-3-chloro-1-(4-methoxyphenethyl)piperidine (0.25 g, 1.0 mmol, prepared by a method disclosed in International Patent No. 9733885A1) in dimethyl sulfoxide (2 ml) was added dropwise to the obtained solution, and they were stirred at 50° C. for 6 hours. The reaction mixture was distributed into saturated aqueous sodium chloride solution and ethyl acetate. The organic layer was dried and the solvent was evaporated under reduced pressure. The residue was subjected to the silica gel column chromatography. After the elution with hexane and ethyl acetate (7:3) as the eluent, suitable fractions were collected and the solvent was evaporated under reduced pressure to obtain (R)-3-fluoro-5,11-dihydro-5-[1-(4-methoxyphenethyl)piperidine-2-ylmethyl]dibenzo[b,e][1,4]oxazepine in the form of a light yellow oily substance (0.30 g, 70%).

ESI/Mass: 433 [M+H$^+$]

NMR (CDCl3) δ: 1.60-1.90(4H, m), 2.27(1H, m), 2.50-2.60(1H, m), 2.70-2.82(3H, m), 2.98-3.10(1H, m), 3.18-3.24 (1H, m), 3.35(1H, dd, J=12.9 Hz), 3.82(3H, s), 4.02(1H, dd, J=3.60, 13.2 Hz), 5.20(1H, d, J=12.0 Hz), 5.27(1H, d, J=12.0 Hz), 6.70-6.95(6H, m), 6.98-7.05(1H, m), 7.15-7.30 (4H, m)

(R)-3-Fluoro-5,11-dihydro-5-[1-(4-methoxyphenethyl)piperidin-2-yl-methyl]dibenzo[b,e][1,4]oxazepine hydrochloride 0.3 ml of 4 M hydrogen chloride/dioxane was added to a solution of (R)-3-fluoro-5,11-dihydro-5-[1-(4-methoxyphenethyl)piperidin-2-yl-methyl]dibenzo[b,e][1,4]oxazepine (300 mg, 0.7 mmol) in dichloromethane (5 ml), and they were stirred together for 30 minutes. The solvent was evaporated under reduced pressure. The obtained residue was solidified with a mixed solvent of hexane and ethyl acetate. The solid thus precipitated was taken by the filtration to obtain the title compound in the form of a brown solid (257 mg, 79%).

ESI/Mass: 433 [M+H$^+$]

NMR (CDCl3) δ: 1.90-2.06(1H, m), 2.06-2.30(3H, m), 2.74-2.86(1H, m), 2.90-3.20(2H, m), 3.25-3.40(1H, m), 3.42-3.68(2H, m), 3.80(3H, s), 3.85-4.00(1H, m), 4.24(1H, dd, J=7.8, 14.1 Hz), 4.62(1H, dd, J=5.7, 14.1 Hz), 5.12(1H, d, J=12.3 Hz), 5.32(1H, d, J=12.3 Hz), 6.72-7.03(8H, m), 7.12(2H, d, J=8.4 Hz), 7.18-7.25(1H, m)

Example 2

(R)-8-Fluoro-5,11-dihydro-5-[1-(4-methoxyphenethyl)pyrrolidin-2-yl-methyl]dibenzo[b,e][1,4]oxazepine hydrochloride (R)-8-Fluoro-5,11-dihydro-5-[1-(4-methoxyphenethyl) pyrrolidin-2-ylmethyl]dibenzo[b,e][1,4]oxazepine was obtained in the same manner as that in Example 1 except that 3-fluoro-5,11-dihydrodibenzo[b,e][1,4]oxazepine was replaced with 8-fluoro-5,11-dihydrodibenzo[b,e][1,4]oxazepine. Light yellow solid. Yield: 19%.

ESI/Mass: 433 [M+H$^+$]

NMR (CDCl3) δ: 1.58-1.88(4H, m), 2.22-2.30(1H, m), 2.48-2.58(1H, m), 2.68-2.82(3H, m), 2.99-3.08(1H, m), 3.21-3.36, 2H, m), 3.81(3H, s), 4.00-4.05(1H, m), 5.20(1H, d, J=13.0 Hz), 5.34(1H, d, J=13.0 Hz), 6.47-6.50(2H, m), 6.79-6.93(3H, m), 7.02-7.18(4H, m), 7.26-7.34(2H, m)

The obtained product was treated with 4 M hydrochloric acid/dioxane in the same manner as that in Example 1 to obtain the title compound in the form of a brown solid. Yield: 81%.

ESI/Mass: 433 [M+H$^+$]

NMR (CDCl3) δ: 1.90-2.32(4H, m), 2.75-2.88(1H, m), 2.94-3.23(2H, m), 3.28-3.60(3H, m), 3.81(3H, s), 3.91-4.00 (1H, m), 4.14-4.30(1H, m), 4.58-4.73(1H, m), 5.17(1H, d, J=13.0 Hz), 5.34(1H, d, J=13.0 Hz), 6.50-6.60(2H, m), 6.81-7.00(3H, m), 7.08-7.39(6H, m)

Example 3

(R)-2-Chloro-5,11-dihydro-5-[1-(4-methoxyphenethyl)pyrrolidin-2-yl-methyl]dibenzo[b,e][1,4]oxazepine hydrochloride (R)-2-Chloro-5,11-dihydro-5-[1-(4-methoxyphenethyl) pyrrolidin-2-ylmethyl]dibenzo[b,e][1,4]oxazepine was obtained in the same manner as that in Example 1 except that 3-fluoro-5,11-dihydrodibenzo[b,e][1,4]oxazepine was replaced with 2-chloro-5,11-dihydrodibenzo[b,e][1,4]oxazepine. Light yellow solid. Yield: 44%.

ESI/Mass: 449 [M+H$^+$]

NMR (CDCl3) δ: 1.60-1.87(4H, m), 2.20-2.28(1H, m), 2048-2.56(1H, m), 2.67-2.82(3H, m), 2.93-3.06(1H, m), 3.16-3.23(1H, m), 3.34(1H, dd, J=10.3, 14.7 Hz), 3.81(3H, s), 4.04(1H, dd, J=4.0, 14.7 Hz), 5.15(1H, d, J=13.0 Hz), 5.25(1H, J=13.0 Hz), 6.75-6.89(5H, m), 6.97-7.04(2H, m), 7.10-7.16(2H, m), 7.22-7.30(2H, m)

The obtained product was treated with 4 M hydrogen chloride/dioxane in the same manner as that in Example 1 to obtain the title compound in the form of a brown solid. Yield: 90%.

ESI/Mass: 449 [M+H$^+$]

NMR (CDCl3) δ: 1.92-2.28(4H, m), 2.72-2.88(1H, m), 2.93-3.13(2H, m), 3.26-3.38(1H, m), 3.43-3.6. (2H, m), 3.81(3H, s), 3.83-3.98(1H, m), 4.20-4.35(1H, m), 4.61-4.74 (1H, m), 5.11(1H, d, J=14.0 Hz), 5.27(1H, d, J=14.0 Hz), 6.87-6.92(5H, m), 7.01-7.16(3H, m), 7.22-7.30(3H, m)

Example 4

(R)-3-Chloro-5,11-dihydro-5-[1-(4-methoxyphenethyl)pyrrolidin-2-ylmethyl]dibenzo[b,e][1,4]oxazepine hydrochloride (R)-3-Chloro-5,11-dihydro-5-[1-(4-methoxyphenethyl) pyrrolidin-2-ylmethyl]dibenzo[b,e][1,4]oxazepine was obtained in the same manner as that in Example 1 except that 3-fluoro-5,11-dihydrodibenzo[b,e][1,4]oxazepine was replaced with 3-chloro-5,11-dihydrodibenzo[b,e][1,4]oxazepine. Light yellow solid. Yield: 55%.

ESI/Mass: 449 [M+H$^+$]

NMR (CDCl3) δ: 160-1.90(4H, m), 2.22-2.30(1H, m), 2.52-2.62(1H, m), 2.68-2.82(3H, m), 2.97-3.07(1H, m), 3.16-3.22(1H, m), 3.35(1H, dd, J=10.3, 14.7 Hz), 3.81(3H, s), 4.03(1H, dd, J=4.0, 14.7 Hz), 5.20(1H, d, J=13.7 Hz), 5.23(1H, d, J=13.7 Hz), 6.75-6.90(5H, m), 6.96-7.02(2H, m), 7.10-7.20(4H, m)

The obtained product was treated with 4 M hydrogen chloride/dioxane in the same manner as that in Example 1 to obtain the title compound in the form of a brown solid. Yield: 86%.

ESI/Mass: 449 [M+H⁺]

NMR (CDCl 3) δ: 1.92-2.03(1H, m), 2.10-2.30(3H, m), 2.75-2.84(1H, m), 2.96-3.12(2H, m), 3.24-3.34(1H, m), 3.44-3.60(2H, m), 3.81(1H, s) 3.87-3.981H, m), 4.24(1H, dd, J=8.7, 15.3 Hz), 4.62(1H, dd, J=6.3, 15.3 Hz), 5.12(1H, d, J=14.0 Hz), 5.35(1H, d, J=14.0 Hz), 6.83-6.96(3H, m), 6.84(2H, d, J=9.3 Hz), 7.01-7.19(4H, m), 7.12(2H, d, J=9.3 Hz)

Example 5

(R)-7-Chloro-5,11-dihydro-5-[1-(3,4-methylenedioxyphenethyl)pyrrolidin-2-ylmethyl]dibenzo[b,e][1,4]oxazepine hydrochloride (R)-3-Chloro-1-[1-(3,4-methylenedioxyphenethyl)piperidine (R)-2-Hydroxymethylpyrrolidine (505 mg, 5.00 mmol), 3,4-methylenedioxyphenethyl mesylate (1.34 g, 5.50 mmol), sodium carbonate (585 mg, 5.50 mmol) and sodium iodide (50 mg, 0.33 mmol) were added to acetonitrile (50 ml), and they were heated at 90° C. under reflux for 13.5 hours. The solvent was evaporated under reduced pressure, and the residue was distributed into ethyl acetate and saturated aqueous sodium hydrogencarbonate solution. The organic layer was washed with water and then dried over magnesium sulfate. The solvent was evaporated under reduced pressure. The obtained residue was dissolved in 25 ml of dichloromethane. 712 mg (5.5 mmol) of diisopropylethylamine and 630 mg (5.5 mmol) of methanesulfonyl chloride were added to the obtained solution under stirring under cooling with water. They were stirred under cooling with ice for 1 hour and then at room temperature for 2 hours. The reaction mixture was distributed into dichloromethane and saturated aqueous sodium hydrogencarbonate solution. The organic layer was dried over magnesium sulfate and the solvent was evaporated under reduced pressure. The residue was subjected to the silica gel column chromatography. After the elution with hexane and ethyl acetate (15:1) as the eluent, suitable fractions were collected and the solvent was evaporated under reduced pressure to obtain (R)-3-chloro-1-(3,4-methylenedioxyphenethyl)piperidine in the form of a light yellow oily substance (1.02 g, 76%).

NMR (CDCl 3) δ: 1.55-1.68(3H, m), 1.75-1.87(1H, m), 2.12-2.20(2H, m), 2.55-2.64(2H, m), 2.69-2.78(3H, m), 3.08-3.18(1H, m), 3.98-4.06(1H, m), 5.93(2H, s), 6.63-6.75(3H, m)

(R)-7-Chloro-5,11-dihydro-5-[1-(3,4-methylenedioxyphenethyl)piperidin-2-ylmethyl]dibenzo[b,e][1,4]oxazepine 60% sodium hydride (48 mg, 1.2 mmol) was washed with hexane in argon gas stream and then suspended in dimethyl sulfoxide (8 ml). The obtained suspension was stirred at room temperature for 30 minutes. 7-Chloro-5,11-dihydrodibenzo[b,e][1,4]oxazepine (232 mg, 1 mmol) was added to the suspension, and they were stirred at room temperature for 30 minutes and then at 50° C. for 30 minutes. A solution of (R)-3-chloro-1-(3,4-methylenedioxyphenethyl)piperidine (308 mg, 1.15 mmol) in dimethyl sulfoxide (3 ml) was added dropwise to the obtained solution, and they were stirred at 50° C. for 4 hours. The reaction mixture was distributed into saturated aqueous sodium hydrogencarbonate solution and ethyl acetate. The organic layer was dried and the solvent was evaporated under reduced pressure. The residue was subjected to the silica gel column chromatography. After the elution with hexane and ethyl acetate (10:1) as the eluent, suitable fractions were collected and the solvent was evaporated under reduced pressure to obtain (R)-7-chloro-5,11-dihydro-5-[1-(3,4-methylenedioxyphenethyl)pyrrolidin-2-ylmethyl]-dibenzo[b,e][1,4]oxazepine in the form of a light yellow solid (362 mg, 78%).

ESI/Mass: 463 [M+H⁺]

NMR (CDCl 3) δ: 160-1.84(4H, m), 2.20-2.30(1H, m), 2.49-2.59(1H, m), 2.65-2.78(3H, m), 2.95-3.05(1H, m), 3.13-3.21(1H, m), 3.34(1H, dd, J=10.3, 13.0 Hz), 4.00(1H, dd, J=3.3, 13.0 Hz), 5.15(1H, d, J=13.0 Hz), 5.23(1H, d, J=13.0 Hz), 5.95(2H, s), 6.63-6.78(5H, m), 6.96(1H, s), 7.02-7.13(2H, m), 7.26-7.37(2H, m)

(R)-7-Chloro-5,11-dihydro-5-[1-(3,4-methylenedioxyphenethyl)pyrrolidin-2-ylmethyl]dibenzo[b,e][1,4]oxazepine hydrochloride 3.0 ml of 2 M hydrogen chloride/diethyl ether was added to a solution of (R)-7-chloro-5,11-dihydro-5-[1-(3,4-methylenedioxyphenethyl)pyrrolidin-2-ylmethyl]dibenzo[b,e][1,4]oxazepine (0.63 g) in dichloromethane (5 ml), and they were stirred together for 2 hours. The solvent was evaporated under reduced pressure. The obtained residue was stirred in hexane to obtain the title compound in the form of a light brown solid (348 mg, 89%).

ESI/Mass: 463 [M+H⁺]

NMR (CDCl 3) δ: 1.92-2.33(4H, m), 2.74-3.16(3H, m), 3.24-3.37(1H, m), 3.44-3.58(2H, m), 3.88-3.98(1H, m), 4.15-4.28(1H, m), 4.60-4.72(1H, 5.19(1H, d, J=14.0 Hz), 5.27(1H, d, J=14.0 Hz), 5.98(2H, s), 6.64-6.77(5H, m), 6.80-6.88(1H, m), 6.98(1H, s), 7.09-7.20(2H, m), 7.28-7.38 (2H, m)

Example 6

(R)-1-Fluoro-5,11-dihydro-5-[1-(4-dimethylaminophenethyl)pyrrolidin-2-yl-methyl]dibenzo[b,e][1,4]oxazepine dihydrochloride (R)-2-Hydroxymethyl-1-(4-dimethylaminophenethyl)pyrrolidine D-Prolinol (2.02 g, 20.0 mmol), 4-dimethylaminophenethyl mesylate (5.35 g, 22.0 mmol), sodium carbonate (2.65 g, 25.0 mmol) and sodium iodide (300 mg, 2.0 mmol) were added to acetonitrile (50 ml), and they were heated at 90° C. under reflux for 13.5 hours. The reaction mixture was cooled to room temperature and then filtered. The filtrate was concentrated to dryness under reduced pressure, and the residue was distributed into ethyl acetate and saturated aqueous sodium hydrogencarbonate solution. 1 M hydrochloric acid was added to the organic layer and pH of the aqueous layer was kept at 1 to extract the intended product in the aqueous layer. 4 M sodium hydroxide was added to the aqueous layer to adjust pH of the aqueous layer to 14, and the precipitates thus formed were extracted with ethyl acetate. The extract was dried over magnesium sulfate, and the solvent was evaporated under reduced pressure to obtain (R)-2-hydroxymethyl-1-(4-dimethyl aminophenethyl)pyrrolidine in the form of a light yellow oily substance (4.91 g, 99%).

NMR (CDCl 3) δ: 1.69-1.90(4H, m), 2.29-2.38(1H, m), 2.45-2.54(1H, m), 2.56-2.64(1H, m), 2.66-2.74(2H, m), 2.88-2.94(1H, m), 2.91(6H, ms), 3.23-3.30(1H, m), 3.31

(1H, dd, J=2.7, 12.0 Hz), 3.58(1H, dd, J=4.0, 12.0 Hz), 6.70(2H, d, J=9.7 Hz), 7.07(2H, d, J=9.7 Hz)

(R)-3-Chloro-1-(4-dimethylaminophenethyl)piperidine (R)-2-Hydroxymethyl-1-(4-dimethylaminophenethyl) pyrrolidine (4.91 g, 19.8 mmol) was dissolved in 60 ml of dichloromethane. 3.11 g (24.4 mmol) of diisopropylethylamine and 2.75 g (24.0 mmol) of methanesulfonyl chloride were added to the obtained solution under stirring under cooling with ice. They were stirred under cooling with ice for 1 hour and then at room temperature for 2 hours. The reaction mixture was distributed into dichloromethane and saturated aqueous sodium hydrogencarbonate solution. The organic layer was dried over magnesium sulfate and the solvent was evaporated under reduced pressure. The residue was subjected to the silica gel column chromatography. After the elution with hexane and ethyl acetate (9:1) as the eluent, suitable fractions were collected and the solvent was evaporated under reduced pressure to obtain (R)-3-chloro-1-(4-dimethylaminophenethyl)piperidine in the form of a light yellow solid (3.03 g, 57%)

NMR (CDCl 3) δ: 1.50-1.68(3H, m), 1.76-1.88(1H, m), 2.09-2.20(2H, m), 2.55-2.62(2H, m), 2.66-2.73(2H, m), 2.75-2.84(1H, m), 2.91(6H, s), 3.08-3.17(1H, m), 3.98-4.08 (1H, m), 6.69(2H, d, J=9.7 Hz), 7.06(2H, d, J=9.7 Hz)

(R)-1-Fluoro-5,11-dihydro-5-[1-(4-dimethylaminophenethyl)pyrrolidin-2-yl-methyl]dibenzo[b,e][1,4]oxazepine 60% sodium hydride (35 mg, 0.88 mmol) was washed with hexane in argon stream and then suspended in dimethyl sulfoxide (5 ml), and the obtained suspension was stirred at room temperature for 30 minutes. 1-Fluoro-5,11-dihydrodibenzo[b,e][1,4]oxazepine (0.17 g, 0.80 mmol) was added to the suspension, and they were stirred at room temperature for 30 minutes and then at 50° C. for additional 30 minutes. A solution of (R)-3-chloro-1-(4-dimethylaminophenethyl) piperidine (0.18 g, 0.80 mmol) in dimethyl sulfoxide (2 ml) was added dropwise to the obtained solution, and they were stirred at 50° C. for 6 hours. The reaction mixture was distributed into saturated aqueous sodium chloride solution and ethyl acetate. The organic layer was dried and the solvent was evaporated under reduced pressure. The residue was subjected to the silica gel column chromatography. After the elution with hexane and ethyl acetate (6:4) as the eluent, suitable fractions were collected and the solvent was evaporated under reduced pressure to obtain (R)-1-fluoro-5,11-dihydro-5-[1-(4-dimethylaminophenethyl)piperidin-2-ylmethyl]dibenzo[b,e][1,4]oxazepine in the form of a light yellow oily substance (0.23 g, 64%).

ESI/Mass: 446 [M+H$^+$]

NMR (CDCl 3) δ: 1.60-1.90(4H, m), 2.20-2.30(1H, m), 2.48-2.55(1H, m), 2.70-2.80(3H, m), 2.94(6H, s), 2.98-3.08 (1H, m), 3.16-3.25(1H, m), 3.38(1H, dd, J=9.3, 13.0 Hz), 4.10(1H, dd, J=3.60, 13.0 Hz), 5.35(1H, d, J=12.0 Hz), 5.42(1H, d, J=12.0 Hz), 6.70-6.78(3H, m), 6.80-6.90(4H, m), 7.00-7.15(3H, m), 7.18-7.28(1H, m)

(R)-1-Fluoro-5,11-dihydro-5-[1-(4-dimethylaminophenethyl)pyrrolidin-2-ylmethyl]dibenzo[b,e][1,4] oxazepine dihydrochloride 0.5 ml of 4 M hydrogen chloride/dioxane was added to a solution of (R)-1-fluoro-5,11-dihydro-5-[1-(4-dimethylaminophenethyl)pyrrolidin-2-ylmethyl]dibenzo[b,e][1,4]oxazepine in dichloromethane (5 ml), and they were stirred together for 30 minutes. The solvent was evaporated under reduced pressure. The obtained residue was solidified with a mixed solvent of hexane and ethyl acetate. The solid thus precipitated was taken by the filtration to obtain the title compound in the form of a brown solid (170 mg, 64%).

ESI/Mass: 446 [M+H$^+$]

NMR (CDCl 3) δ: 1.92-2.30(3H, m), 2.78-2.90(1H, m), 2.91-3.16(3H, m), 3.16(6H, s), 3.38-3.50(2H, m), 3.62-3.75 (1H, m), 3.82-3.95(1H, m), 4.28(1H, dd, J=6.3, 14.7 Hz), 4.77(1H, dd, J=6.0, 14.7 Hz), 5.24(2H, s), 6.76(1H, t, J=8.1 Hz), 6.90-7.12(5H, m), 7.21-7.30(1H, m), 7.37(2H, d, J=8.4 Hz), 7.71(2H, d, J=8.4 Hz)

Example 7

(R)-3-Fluoro-5,11-dihydro-5-[1-(4-dimethylaminophenethyl)pyrrolidin-2-yl-methyl]dibenzo[b,e][1,4]oxazepine dihydrochloride (R)-3-Fluoro-5,11-dihydro-5-[1-(4-dimethylaminophenethyl)pyrrolidin-2-ylmethyl]dibenzo[b,e][1,4]oxazepine was obtained in the form of a light yellow oily substance in the same manner as that in Example 6 except that 1-fluoro-5,11-dihydrodibenzo[b,e][1,4]oxazepine was replaced with 3-fluoro-5,11-dihydrodibenzo[b,e][1,4]oxazepine. (0.24 g, 53%).

ESI/Mass: 446 [M+H$^+$]

NMR (CDCl 3) δ: 160-1.90(4H, m), 2.22-2.32(1H, m), 2.50-2.60(1H, m), 2.70-2.82(3H, m), 2.94(6H, s), 2.98-3.08 (1H, m), 3.15-3.25(1H, m), 3.34(1H, dd, J=9.3, 13.0 Hz), 4.05(1H, dd, J=3.60, 13.0 Hz), 5.20(1H, d, J=12.0 Hz), 5.26(1H, d, J=12.0 Hz), 6.68-6.90(7H, m), 6.97-7.04(1H, m), 7.08-7.15(2H, m), 7.20-7.25(1H, m)

The obtained product was treated with 4 M hydrogen chloride/dioxane in the same manner as that in Example 6 to obtain the title compound in the form of a light brown solid (100%)

ESI/Mass:446 [M+H$^+$]

NMR (CDCl 3) δ: 1.95-2.30(3H, m), 2.80-3.00(1H, m), 3.00-3.25(9H, m), 3.42-3.60(2H, m), 3.60-3.75(1H, m), 3.85-3.98(1H, m), 4.19-4.28(1H, m), 4.58-4.68(1H, m), 5.11 (1H, d, J=12.6 Hz), 5.35(1H, d, J=12.6 Hz), 6.76(1H, t, J=8.1 Hz), 6.80-7.08(5H, m), 7.20(1H, dd, J=6.3, 8.1 Hz), 7.43(2H, d, J=6.9 Hz), 7.75(2H, d, J=6.9 Hz)

Example 8

(R)-3-Chloro-5,11-dihydro-5-[1-(4-dimethylaminophenethyl)pyrrolidin-2-ylmethyl]dibenzo[b,e][1,4] oxazepine dihydrochloride (R)-3-Chloro-5,11-dihydro-5-[1-(4-dimethylaminophenethyl)pyrrolidin-2-ylmethyl]dibenzo[b,e][1,4]oxazepine was obtained in the same manner as that in Example 6 except that 1-fluoro-5,11-dihydrodibenzo[b,e][1,4]oxazepine was replaced with 3-chloro-5,11-dihydrodibenzo[b,e][1,4]oxazepine. Light yellow oily substance. Yield: 67%.

ESI/Mass: 462 [M+H$^+$]

NMR (CDCl 3) δ: 1.50-1.91(4H, m), 2.23-2.32(1H, m), 2.51-2.60(1H, m), 2.65-2.83(3H, m), 2.93(6H, s), 2.97-3.07 (1H, m), 3.15-3.23(1H, m), 3.34(1H, dd, J=10.3, 14.3 Hz), 4.06(1H, dd, J=4.0, 14.3 Hz), 5.22(2H, s), 6.72(2H, d, J=10.0 Hz), 6.75-6.85(3H, m), 6.98-7.01(2H, m), 7.09-7.19 (2H, m), 7.11(2H, d, J=10.0 Hz)

(R)-3-Chloro-5,11-dihydro-5-[1-(4-dimethylaminophenethyl)pyrrolidin-2-ylmethyl]dibenzo[b,e][1,4]oxazepine (306 mg, 0.662 mmol) was dissolved in 6.0 ml of a mixed solvent of ethyl acetate and ethanol (2:1). 2 M hydrogen chloride/ether (0.73 ml, 1.46 mmol) was added to the obtained solution. 2.0 ml of ethyl acetate was added to the mixture and they were stirred at room temperature. After leaving the reaction mixture to stand at room temperature for 2 days followed by the filtration and drying, the title compound was obtained in the form of white crystals (96%).

ESI/Mass: 462 [M+H$^+$]

NMR (CDCl 3) δ: 2.02-2.28(4H, m), 2.80-2.90(1H, m), 2.98-3.24(2H, m), 3.17(6H, s), 3.44-3.56(2H, m), 3.59-3.69 (1H, m), 3.88-3.98(1H, m), 4.23(1H, dd, J=7.7, 15.7 Hz), 4.64(1H, dd, J=6.3, 15.7 Hz), 5.11(1H, d, J=14.0 Hz), 5.33(1H, d, J=14.0 Hz), 6.85-6.97(3H, m), 7.02-7.07(2H, m), 7.12-7.18(2H, m), 7.41(2H, d, J=9.3 Hz), 7.75(2H, d, J=9.3 Hz)

Example 9

(R)-2-Fluoro-5,11-dihydro-5-[1-(4-pyrrolidinophenethyl)pyrrolidin-2-ylmethyl]dibenzo[b,e][1,4]oxazepine dihydrochloride 4-Pyrrolidinophenethyl Alcohol A solution of 2-(4-bromophenethoxy)tetrahydro-2H-pyran (28.01 g, 98.39 mmol) in toluene (100 ml) and pyrrolidine (9.93 ml, 119 mmol) were added to a mixture of dry palladium acetate (270 mg, 1.20 mmol), 2-(di-t-butylphosphino)biphenyl (720 mg, 2.40 mmol) and sodium t-butoxide (14.42 g, 150 mmol), and they were stirred at 70° C. for 12 hours. Water was added to the reaction mixture. After the extraction with ethyl acetate, the product was extracted from the organic layer with 1 M hydrochloric acid. The aqueous layer was neutralized with an aqueous sodium hydroxide solution and extracted with ethyl acetate. The organic layer was dried to obtain 4-pyrrolidinophenethyl alcohol in the form of a light yellow solid (16.41 g, 87%).

NMR (CDCl 3) δ: 1.97-2.01(4H, m), 2.77(2H, t, J=7.3 Hz), 3.24-3.29(4H, m), 3.79(2H, q, J=6.7 Hz), 6.53(2H, d, J=9.3 Hz), 7.03(2H, d, J=9.35 Hz)

4-Pyrrolidinophenethyl Mesylate

4-Pyrrolidinophenethyl alcohol (16.41 g, 85.9 mmol) was dissolved in dichloromethane (150 ml). Dissopropylethylamine (19.0 ml, 108 ml) and methanesulfonyl chloride (8.40 ml, 108 mmol) were added to the obtained solution at 0° C., and they were stirred overnight. The reaction mixture was distributed into 5% aqueous sodium hydrogencarbonate solution and dichloromethane. The organic layer was dried and the solvent was evaporated under reduced pressure. The residue was subjected to the silica gel column chromatography. After the elution with hexane and ethyl acetate (7:3) as the eluent, suitable fractions were collected and the solvent was evaporated under reduced pressure to obtain 4-pyrrolidinophenethyl mesylate in the form of a white solid (21.14 g, 80%).

ESI/Mass: 270 [M+H$^+$]

NMR (CDCl 3) δ: 1.98-2.01(4H, m), 2.84(3H, s), 2.95 (2H, t, J=8.0 Hz), 3.24-3.28(4H, m), 4.46(2H, t, J=8.0 Hz), 6.52(2H, d, J=9.3 Hz), 7.07(2H, d, J=9.3 Hz)

(R)-2-Hydroxymethyl-1-(4-pyrrolidinophenethyl) pyrrolidine

D-Prolinol (2.72 g, 25.0 mmol), 4-pyrrolidinophenethyl mesylate (6.06 g, 22.5 mmol) and sodium carbonate (3.45 g, 25.0 mmol) were added to acetonitrile (150 ml), and they were heated at 90° C. under reflux for 3.5 hours. The reaction mixture was cooled to room temperature and then filtered. The filtrate was concentrated to dryness under reduced pressure, and the residue was distributed into ethyl acetate and saturated aqueous sodium hydrogencarbonate solution. 1 M hydrochloric acid was added to the organic layer and pH of the aqueous layer was kept at 1 to extract the intended product in the aqueous layer. 4 M sodium hydroxide was added to the aqueous layer to adjust pH of the aqueous layer to 14, and the intended product was extracted from the precipitates thus formed with ethyl acetate. The extract was dried over magnesium sulfate, and the solvent was evaporated under reduced pressure to obtain (R)-2-hydroxymethyl-1-(4-pyrrolidinophenethyl)pyrrolidine in the form of a light yellow oily substance (4.96 g, 85%).

NMR (CDCl 3) δ: 1.70-1.91(4H, m), 1.95-2.04(4H, m), 2.26-2.36(1H, m), 2.42-2.56(1H, m), 2.57-2.77(4H, m), 2.87-2.96(1H, m), 3.18-3.27(4H, m), 3.28(1H, dd, J=2.7, 12.0 Hz), 3.57(1H, dd, J=4.0, 12.0 Hz), 6.51(2H, d, J=9.3 Hz), 7.05(2H, d, J=9.7 Hz)

(R)-3-Chloro-1-(4-pyrrolidinophenethyl)piperidine (R)-2-Hydroxymethyl-1-(4-pyrrolidinophenethyl)pyrrolidine (4.96 g, 19.1 mmol) was dissolved in 70 ml of dichloromethane. 3.21 g (24.8 mmol) of diisopropylethylamine and 2.84 g (24.8 mmol) of methanesulfonyl chloride were added to the obtained solution under stirring under cooling with ice. They were stirred under cooling with ice for 1 hour and then at room temperature for 2 hours. The reaction mixture was distributed into dichloromethane and saturated aqueous sodium hydrogencarbonate solution. The organic layer was dried over magnesium sulfate and the solvent was evaporated under reduced pressure. The residue was subjected to the silica gel column chromatography. After the elution with hexane and ethyl acetate (3:1) as the eluent, suitable fractions were collected and the solvent was evaporated under reduced pressure to obtain (R)-3-chloro-1-(4-pyrrolidinophenethyl)piperidine in the form of a light yellow solid (3.23 g, 61%).

ESI/Mass: 293 [M+H$^+$]

NMR (CDCl 3) δ: 1.50-1.70(3H, m), 1.78-1.87(1H, m), 1.96-2.01(4H, m), 2.10-2.20(2H, m), 2.54-2.61(2H, m), 2.65-2.72(2H, m), 2.75-2.85(1H, m), 3.10-3.17(1H, m), 3.23-3.28(4H, m), 3.96-4.06(1H, m), 6.51(2H, d, J=9.7 Hz), 7.05(2H, d, J=9.7 Hz)

(R)-2-Fluoro-5,11-dihydro-5-[1-(4-pyrrolidinophenethyl)pyrrolidin-2-yl-methyl]dibenzo[b,e][1,4]oxazepine 60% sodium hydride (348 mg, 8.7 mmol) was washed with hexane in argon stream and then suspended in dimethyl sulfoxide (50 ml), and the obtained suspension was stirred at room temperature for 30 minutes. 2-Fluoro-5,11-dihydrodibenzo[b,e][1,4]oxazepine (1.70 g, 7.90 mmol) was added to the suspension, and they were.stirred at room temperature for 30 minutes and then at 50° C. for additional 30 minutes. A solution of (R)-3-chloro-1-(4-pyrrolidinophenethyl)piperidine (2.64 g, 9.02 mmol) in dimethyl sulfoxide (25 ml) was added dropwise to the obtained solution, and they were stirred at 50° C. for 3 hours. The reaction mixture was distributed into saturated aqueous sodium hydrogencarbonate solution and ethyl acetate. The organic layer was dried and the solvent was evaporated under reduced pressure. The residue was subjected to the silica gel column chromatography. After the elution with hexane and ethyl acetate (6:1) and then with hexane and ethyl acetate (1:1) as the eluent, suitable fractions were collected and the solvent was evaporated under reduced pressure to obtain (R)-2-fluoro-5,11-dihydro-5-[1-(4-pyrrolidinophenethyl)pyrrolidin-2-ylmethyl]dibenzo[b,e][1,4]oxazepine in the form of a light yellow oily substance (2.29 g, 68%).

ESI/Mass: 472 [M+H$^+$]

NMR (CDCl 3) δ: 1.59-1.86(4H, m), 1.96-2.02(4H, m), 2.21-2.29(1H, m), 2.46-2.55(1H, m), 2.60-2.78(3H, m), 2.97-3.06(1H, m), 3.19-3.31(6H, m) 4.08(1H, dd, 3.7, 14.3 Hz), 5.16(1H, m), 5.30(1H, d, J=13.0 Hz), 6.54(2H, d, J=9.0 Hz), 6.75-6.85(3H, m), 6.95-7.09(4H, m), 6.99(2H, d, J=9.0 Hz)

(R)-2-Fluoro-5,11-dihydro-5-[1-(4-pyrrolidinophenethyl)pyrrolidin-2-yl-methyl]dibenzo[b,e][1,4]oxazepine dihydrochloride 20 ml of 2 M hydrogen chloride/diethyl ether was added to a solution of (R)-2-fluoro-5,11-dihydro-5-[1-(4-pyrrolidinophenethyl)pyrrolidin-2-ylmethyl]dibenzo[b,e][1,4]oxazepine (2.29 g) in dichloromethane (30 ml), and they were stirred together for 2 hours. The solvent was evaporated under reduced pressure. The obtained residue was solidified by stirring it in hexane. The solid thus precipitated was taken by the filtration to obtain the title compound in the form of a brown solid (2.17 g, 81%).

ESI/Mass: 472 [M+H$^+$]

NMR (CDCl 3) δ: 1.95-2.36(8H, m), 2.84-2.96(1H, m), 3.03-3.27(3H, m), 3.40-3.72(6H, m), 3.82-3.93(1H, m), 4.21 (1H, dd, J=8.7, 15.7 Hz), 4.63(1H, dd, J=6.3, 15.7 Hz), 5.13(1H, d, J=14.0 Hz), 5.33(1H, d, J=14.0 Hz), 6.81-7.03 (6H, m), 7.11-7.14(1H, m), 7.37(2H, d, J=9.0 Hz), 7.60(2H, d, J=9.0 Hz)

Example 10

(R)-3-Fluoro-5,11-dihydro-5-[1-(4-pyrrolidinophenethyl)pyrrolidin-2-yl-methyl]dibenzo[b,e][1,4]oxazepine dihydrochloride (R)-3-Fluoro-5,11-dihydro-5-[1-(4-pyrrolidinophenethyl)pyrrolidin-2-ylmethyl]dibenzo[b,e][1,4]oxazepine was obtained in the form of a light yellow oily substance (0.19 g, 50%) in the same manner as that in Example 6 except that 3-fluoro-5,11-dihydrodibenzo[b,e][1,4]oxazepine and (R)-3-chloro-1-(4-pyrrolidinophenethyl)piperidine were used.

ESI/Mass: 472 [M+H$^+$]

NMR (CDCl 3) δ: 1.55-1.90(4H, m), 1.95-2.06(4H, m), 2.20-2.32(1H, m), 2.48-2.60(1H, m), 2.70-2.82(3H, m), 2.95-3.10(1H, m), 3.18-3.40(6H, m), 4.06(1H, m), 5.20(1H, d, J=12.0 Hz), 5.26(1H, d, J=12.0 Hz), 6.54(2H, d, J=8.7 Hz), 6.68-6.85(5H, m), 6.95-7.03(1H, m), 7.08(2H, d, J=8.7 Hz), 7.20-7.30(1H, m)

The obtained product was treated with 4 M hydrogen chloride/dioxane in the same manner as that in Example 6 to obtain the title compound in the form of a brown solid (90%).

ESI/Mass: 472 [M+H$^+$]

NMR (CDCl 3) δ: 1.95-2.30(4H, m), 2.34(4H, m), 2.82-2.95(1H, m), 3.00-3.24(2H, m), 3.39-3.78(7H, m), 3.82-3.95 (1H, m), 4.21(1H, dd, J=7.2, 14.1 Hz), 4.62(1H, dd, J=5.7, 14.1 Hz), 5.11(1H, d, J=12.6 Hz), 5.34(1H, d, J=12.6 Hz), 6.76(1H, t, J=8.1 Hz), 6.80-7.05(5H, m), 7.19(1H, t, J=8.1 Hz), 7.37(2H, d, J=8.4 Hz), 7.64(2H, d, J=8.4 Hz)

Example 11

(R)-7-Fluoro-5,11-dihydro-5-[1-(4-pyrrolidinophenethyl)pyrrolidin-2-yl-methyl]dibenzo[b,e][1,4]oxazepine dihydrochloride (R)-7-Fluoro-5,11-dihydro-5-[1-(4-pyrrolidinophenethyl)pyrrolidin-2-ylmethyl]dibenzo[b,e][1,4]oxazepine was obtained in the form of a light yellow oily substance (0.19 g, 51%) in the same manner as that in Example 6 except that 7-fluoro-5,11-dihydrodibenzo[b,e][1,4]oxazepine and (R)-3-chloro-1-(4-pyrrolidinophenethyl)piperidine were used.

ESI/Mass: 472 [M+H$^+$]

NMR (CDCl 3) δ: 1.58-1.90(4H, m), 1.95-2.06(4H, m), 2.20-2.32(1H, m), 2.48-2.60(1H, m), 2.68-2.82(3H, m), 2.98-3.08(1H, m), 3.18-3.40(6H, m), 4.05(1H, dd, J=5.8, 13.2 Hz), 5.14(1H, d, J=12.0 Hz), 5.31(1H, d, J=12.0 Hz), 6.45-6.58(3H, m), 6.68-6.78(2H, m), 7.02-7.13(4H, m), 7.28-7.35(2H, m)

The obtained product was treated with 4 M hydrogen chloride/dioxane in the same manner as that in Example 6 to obtain the title compound in the form of a brown solid (98%).

ESI/Mass: 472 [M+H$^+$]

NMR (CDCl 3) δ: 1.95-2.30(4H, m), 2.34(4H, m), 2.78-2.92(1H, m), 2.94-3.25(2H, m), 3.40-3.76(7H, m), 3.83-3.94 (1H, m), 4.23(1H, dd, J=7.2, 14.4 Hz), 4.66(1H, dd, J=6.0, 14.4 Hz), 5.13(1H, d, J=12.9 Hz), 5.24(1H, d, J=12.9 Hz), 6.58-6.63(1H, m), 6.72-6.82(2H, m), 7.05-7.25(4H, m), 7.35 (2H, d, J=8.4 Hz), 7.60(2H, d, J=8.4 Hz)

Example 12

(R)-8-Fluoro-5,11-dihydro-5-[1-(4-pyrrolidinophenethyl)pyrrolidin-2-yl-methyl]dibenzo[b,e]1,4]oxazepine dihydrochloride (R)-8-Fluoro-5,11-dihydro-5-[1-(4-pyrrolidinophenethyl)pyrrolidin-2-ylmethyl]dibenzo[b,e][1,4]oxazepine was obtained in the form of a light yellow oily substance (0.13 g, 32%) in the same manner as that in Example 6 except that 8-fluoro-5,11-dihydrodibenzo[b,e][1,4]oxazepine and (R)-3-chloro-1-(4-pyrrolidinophenethyl)piperidine were used.

ESI/Mass: 472 [M+H$^+$]

NMR (CDCl 3) δ: 1.58-1.90(4H, m), 1.95-2.06(4H, m), 2.18-2.34(1H, m), 2.45-2.58(1H, m), 2.65-2.80(3H, m), 2.95-3.10(1H, m), 3.14-3.38(6H, m), 4.05-4.14(1H, m), 5.21 (1H, d, J=11.7 Hz), 5.35(1H, d, J=11.7 Hz), 6.48-6.58(4H, m), 6.88-6.95(1H, m), 7.02-7.12(4H, m), 7.24-7.35(2H, m)

The obtained product was treated with 4 M hydrogen chloride/dioxane in the same manner as that in Example 6 to obtain the title compound in the form of a brown solid (98%).

ESI/Mass: 472 [M+H$^+$]

NMR (CDCl 3) δ: 1.95-2.30(4H, m), 2.35(4H, m), 2.78-2.94(1H, m), 2.95-3.10(1H, m), 3.10-3.25(1H, m), 3.40-3.80 (7H, m), 3.80-3.95(1H, m), 4.19(1H, dd, J=7.8, 14.1 Hz), 4.64(1H, dd, J=4.2, 14.1 Hz), 5.16(1H, d, J=12.3 Hz), 5.44(1H, d, J=12.3 Hz), 6.50-6.61(2H, m), 6.88-7.00(1H, m), 7.05-7.18(2H, m), 7.30-7.41(4H, m), 7.64(2H, d, J=7.8 Hz)

Example 13

(R)-3-Chloro-5,11-dihydro-5-[1-(4-pyrrolidinophenethyl)pyrrolidin-2-yl-methyl]dibenzo[b,e][1,4]oxazepine dihydrochloride (R)-3-Chloro-5,11-dihydro-5-[1-(4-pyrrolidinophenethyl)pyrrolidin-2-ylmethyl]dibenzo[b,e][1,4]oxazepine was obtained in the form of a light yellow oily substance (0.18 g, 68%) in the same manner as that in Example 6 except that 3-chloro-5,11-dihydrodibenzo[b,e][1,4]oxazepine and (R)-3-chloro-1-(4-pyrrolidinophenethyl)piperidine were used.

ESI/Mass: 48 8 [M+H$^+$]

NMR (CDCl$_3$) δ: 1.50-1.90(4H, m), 1.95-2.06(4H, m), 2.20-2.34(1H, m), 2.50-2.62(1H, m), 2.65-2.82(3H, m), 2.90-3.10(1H, m), 3.16-3.40(6H, m), 4.05-4.14(1H, m), 5.22 (2H, s), 6.54(2H, d, J=8.7 Hz), 6.75-6.88(3H, m), 6.96-7.04 (2H, d, J=8.7 Hz), 7.05-7.14(3H, m), 7.18(1H, d, J=8.4 Hz)

The obtained product was treated with 4 M hydrogen chloride/dioxane in the same manner as that in Example 6 to obtain the title compound in the form of a brown solid (91%).

ESI/Mass: 4 8 8 [M+H$^+$]

NMR (CDCl$_3$) δ: 1.95-2.30(4H, m), 2.34(4H, m), 2.78-2.92(1H, m), 2.92-3.25(2H, m), 3.40-3.81(7H, m), 3.83-3.99 (1H, m), 4.21(1H, dd, J=6.9, 14.1 Hz), 4.63(1H, dd, J=6.3, 14.1 Hz), 5.10(1H, d, J=12.9 Hz), 5.36(1H, d, J=12.9 Hz), 6.85-7.06(5H, m), 7.15(2H, t, J=8.1 Hz), 7.35(2H, d, J=8.7 Hz), 7.62(2H, d, J=8.7 Hz)

Example 14

(R)-3-Chloro-5,11-dihydro-5-[1-(3-pyrrolidinophenethyl)pyrrolidin-2-ylmethyl]dibenzo[b,e][1,4]oxazepine dihydrochloride

3-Pyrrolidinophenethyl Alcohol

A solution of 2-(3-bromophenethoxy)tetrahydro-2H-pyran (6.27 g, 21.9 mmol) in toluene (15 ml) and pyrrolidine (2.2 ml, 26.4 mmol) were added to a mixture of dry palladium acetate (58 mg, 0.26 mmol), 2-(di-t-butylphosphino)biphenyl (136 mg, 0.46 mmol) and sodium t-butoxide (3.23 g, 33.6 mmol), and they were stirred at 70° C. for 12 hours. Water was added to the reaction mixture. After the extraction with ethyl acetate, the product was extracted from the organic layer with 1 M hydrochloric acid. The aqueous layer was neutralized with an aqueous sodium hydroxide solution and the product was extracted with ethyl acetate. The organic layer was dried to quantitatively obtain 3-pyrrolidinophenethyl alcohol in the form of a light yellow solid.

NMR (CDCl$_3$) δ: 1.98-2.02(4H, m), 2.82(2H, t, J=7.0 Hz), 3.26-3.30(4H, m), 3.86(2H, q, J=7.0 Hz), 6.42-6.54 (3H, m), 7.17(1H, t, J=8.3 Hz)

3-Pyrrolidinophenethyl Mesylate

3-Pyrrolidinophenethyl alcohol was dissolved in dichloromethane (20 ml). Triethylamine (3.7 ml, 26.7 ml) and methanesulfonyl chloride (1.9 ml, 24.5 mmol) were added to the obtained solution at 0° C., and they were stirred overnight. The reaction mixture was distributed into 5% aqueous sodium hydrogencarbonate solution and dichloromethane. The organic layer was dried and the solvent was evaporated under reduced pressure. The residue was subjected to the silica gel column chromatography. After the elution with hexane and ethyl acetate (7:3), suitable fractions were collected and the solvent was evaporated under reduced pressure to obtain 3-pyrrolidinophenethyl mesylate in the form of a white solid (5.13 g, 87%).

ESI/Mass: 2 70[M+H$^+$]

NMR (CDCl$_3$) δ: 1.98-2.03(4H, m), 2.86(3H, s), 2.98 (2H, t, J=7.3 Hz), 3.25-3.30(4H,m), 4.43(2H, t, J=7.3 Hz), 6.40-6.53(3H,m), 7.16(1H, t, J=8.7 Hz)

(R)-3-Chloro-1-(3-pyrrolidinophenethyl)piperidine (R)-3-Chloro 1-(3-pyrrolidinophenethyl)piperidine was synthesized in the same manner as that in Example 13 except that 4-pyrrolidinophenethyl mesylate was replaced with 3-pyrrolidinophenethyl mesylate. Yield: 50%.

ESI/Mass: 293 [M+H$^+$]

NMR (CDCl$_3$) δ: 1.55-1.70(2H, m), 1.78-1.88(2H, m), 1.95-2.03(4H, m), 2.10-2.22(2H,m), 2.30(1H, t, J=10.5 Hz), 2.60-2.67(2H, m), 2.67-2.82(2H, m), 3.16(1H, m), 3.22-3.30 (4H, m), 4.02(1H, m), 6.40(2H, m), 6.49(1H, d, J=7, 5 Hz), 7.13(1H, t, J=7.5 Hz)

(R)-3-Chloro-5,11-dihydro-5-[1-(3-pyrrolidinophenethyl)pyrrolidin-2-yl-methyl]dibenzo[b,e][1,4]oxazepine (R)-3-Chloro-5,11-dihydro-5-[1-(3-pyrrolidinophenethyl)pyrrolidin-2-yl-methyl]dibenzo[b,e][1,4]oxazepine was obtained in the form of a light yellow oily substance (0.21 g, 45%) from 3-chloro-5,11-dihydrodibenzo[b,e][1,4]oxazepine and (R)-3-chloro-1-(3-pyrrolidinophenethyl)piperidine in the same manner as that in Example 6.

ESI/Mass: 488 [M+H$^+$]

NMR (CDCl$_3$) δ: 1.50-1.90(4H, m), 1.95-2.06(4H, m), 2.24-2.34(1H, m), 2.55-2.70(1H, m), 2.70-2.88(3H, m), 3.02-3.15(1H, m), 3.16-3.40(6H, m), 4.02-4.14(1H, m), 5.23 (2H, s), 6.40-6.58(3H, m), 6.75-6.88(3H, m), 6.96-7.04(2H, m), 7.10-7.20(3H, m)

(R)-3-Chloro-5,11-dihydro-5-[1-(3-pyrrolidinophenethyl)pyrrolidin-2-yl-methyl]dibenzo[b,e][1,4]oxazepine dihydrochloride The obtained product was treated with 4 M hydrogen chloride/dioxane in the same manner as that in Example 6 to obtain the title compound in the form of a brown solid (88%).

ESI/Mass: 488 [M+H$^+$]

NMR (CDCl$_3$) δ: 1.95-2.30(4H, m), 2.32(4H, m), 2.77-2.90(1H, m), 3.00-3.30(2H, m), 3.38-3.78(7H, m), 3.80-3.92 (1H, m), 4.21(1H, dd, J=6.6, 14.1 Hz), 4.64(1H, dd, J=5.7, 14.1 Hz), 5.10(1H, d, J=12.9 Hz), 5.33(1H, d, J=12.9 Hz), 6.82-7.08(5H, m), 7.14(2H, t, J=8.4 Hz), 7.20-7.30(1H, m), 7.38-7.53(2H, m), 7.60-7.70(1H, m)

Example 15

(R)-3-Chloro-5,11-dihydro-5-[1-(4-morpholinophenethyl)pyrrolidin-2-yl-methyl]dibenzo[b,e][1,4]oxazepine dihydrochloride

4-Morpholinophenethyl Alcohol

A solution of 2-(4-bromophenethoxy)tetrahydro-2H-pyran (3.42 g, 12 mmol) in toluene (9.0 ml) and morpholine (1.22 g, 14 mmol) were added to a mixture of dry palladium acetate (32.3 mg, 0.14 mmol), 2-(di-t-butylphosphino)biphenyl (86.0 mg, 0.29 mmol) and sodium t-butoxide (1.73 g, 18 mmol), and they were stirred at 70° C. for 16 hours. Water was added to the reaction mixture. After the extraction with ethyl acetate, the product was extracted from the organic layer with 1 M hydrochloric acid. The aqueous layer was neutralized with an aqueous sodium hydroxide solution and the product was extracted with ethyl acetate. The organic layer was dried to obtain 4-morpholinophenethyl alcohol in the form of a light yellow solid (2.35 g, 95%).

NMR (CDCl 3) δ: 2.80(2H, t, J=8.7 Hz), 3.13(4H, t, J=6.8), 3.78-3.88(6H. m), 6.88(2H, d, J=11.7 Hz), 7.14(2H, d, J=11.7 Hz)

4-Morpholinophenethyl Mesylate

4-Morpholinophenethyl alcohol (2.35 g, 11.3 mmol) was dissolved in dichloromethane (20 ml). Diisopropylethylamine (2.60 ml, 14.8 mmol) and methanesulfonyl chloride (1.11 ml, 14.8 mmol) were added to the obtained solution at 0° C., and they were stirred for 4 hours. The reaction mixture was distributed into 5% aqueous sodium hydrogencarbonate solution and dichloromethane. The organic layer was dried and the solvent was evaporated under reduced pressure. The residue was subjected to the silica gel column chromatography. After the elution with hexane and ethyl acetate (3:1) and then with them (1:1) as the eluents, suitable fractions were collected and the solvent was evaporated under reduced pressure to obtain 4-morpholinophenethyl mesylate in the form of a white solid (2.60 g, 81%).

NMR (CDCl 3) δ: 2.86(3H, s), 2.98(2H, t, J=9.3 Hz), 3.14(4H, m), 3.86(4H, m), 4.38(2H, t, J=9.3 Hz), 6.87(2H, d, J=11.7 Hz), 7.14(2H, d, J=11.7 Hz)

(R)-3-Chloro-1-(4-morpholinophenethyl)piperidine

4-Morpholinophenethyl mesylate (0.43 g, 1.51 mmol), D-prolinol (0.17 g, 1.66 mmol) and sodium carbonate (0.40 g, 2.89 mmol) were added to acetonitrile (20 ml), and they were stirred under heating at 70° C. overnight. The reaction mixture was cooled and then filtered. The filtrate was evaporated to dryness under reduced pressure, and the residue was distributed into water and ethyl acetate. The intended product was extracted from ethyl acetate layer with 1 M hydrochloric acid. The aqueous layer was neutralized and the product was again extracted with ethyl acetate. The organic layer was dried and the solvent was evaporated under reduced pressure to obtain (R)-2-hydroxymethyl-1-(4-morpholinophenethyl)pyrrolidine in the form of a light yellow solid (0.44 g, 1.5 mmol, 100%). This product was dissolved in dichloromethane (10 ml). Triethylamine (0.29 ml, 2.1 mmol) and methanesulfonyl chloride (0.15 ml, 1.9 mmol) were added to the obtained solution at 0° C., and they were stirred at room temperature for 1 hour. The reaction mixture was distributed into 5% aqueous sodium hydrogencarbonate solution and dichloromethane. The organic layer was dried and the solvent was evaporated under reduced pressure. The residue was subjected to the silica gel column chromatography. After the elution with hexane and ethyl acetate (1:1), suitable fractions were collected and the solvent was evaporated under reduced pressure to obtain (R)-3-chloro-1-(morpholinophenethyl)piperidine in the form of a white solid (0.30 g, 64%).

ESI/Mass: 30 9 [M+H⁺]

NMR (CDCl 3) δ: 1.50-1.86(4H, m), 2.10-2.20(2H, m), 2.28(1H, t, J=7.8 Hz), 2.55-2.64(2H, m), 2.65-2.80(3H, m), 3.10-3.18(4H, m), 3.80-3.88(4H, m), 3.96-4.04(1H, m), 6.82-6.88(2H, m), 7.10-7.20(2H, m)

(R)-3-Chloro-5,11-dihydro-5-[1-(4-morpholinophenethyl)pyrrolidin-2-yl-methyl]dibenzo[b,e][1,4]oxazepine dihydrochloride (R)-3-Chloro-5,11-dihydro-5-[1-(4-morpholinophenethyl)pyrrolidin-2-ylmethyl]dibenzo[b,e][1,4]oxazepine was obtained from (R)-3-chloro-1-(4-morpholinophenethyl)piperidine and 3-chloro-5,11-dihydrodibenzo[b,e][1,4]oxazepine in the same manner as that in Example 6. Light yellow oily substance. Yield: 46%.

ESI/Mass: 504 [M+H⁺]

NMR (CDCl 3) δ: 1.60-1.95(4H, m), 2.22-2.31(1H, m), 2.52-2.61(1H, m), 2.69-2.80(3H, m), 2.98-3.07(1H, m), 3.01-3.19(1H, m), 3.15(4H, t, J=5.3 Hz), 3.35(1H, dd, J=10, 3, 14.7 Hz), 3.87(4H, t, J=5.3 Hz), 4.03(1H, dd, J=4.0, 14.7 Hz), 5.21(1H, d, J=13.3 Hz), 5.23(1H, d, J=13.3 Hz), 6.76-6.90(3H, m), 6.88(2H, d, J=9.7 Hz), 6.97-7.01(2H, m), 7.09-7.19(2H, m), 7.14(2H, d, J=9.7 Hz)

The obtained product was treated with 4 M hydrogen chloride/dioxane in the same manner as that in Example 6 to obtain the title compound in the form of a brown solid. Yield: 96%

ESI/Mass: 504 [M+H⁺]

NMR (CDCl 3) δ: 1.98-2.33(4H, m), 2.83-3.30(4H, m), 3.38-3.70(6H, m), 3.87-3.98(1H, m), 4.15-4.42(5H, m), 4.60-4.70(1H, m), 5.12(1H, d, J=14.0 Hz), 5.39(1H, d, J=14.0 Hz), 6.84-6.93(3H, m), 7.04-7.19(4H, m), 7.43(2H, s), 7.78(2H, s)

Example 16

(R)-2-Fluoro-5,11-dihydro-5-[1-(4-dimethylaminophenethyl)pyrrolidin-3-yl]dibenzo[b,e][1,4]oxazepine dihydrochloride (R)-2-Fluoro-5,11-dihydro-5-[1-(4-dimethylaminophenethyl)pyrrolidin-3-yl]dibenzo[b,e][1,4]oxazepine 60% sodium hydride (100 mg, 2.5 mmol) was washed with hexane in argon stream and then suspended in dimethyl sulfoxide (8 ml), and the obtained suspension was stirred at room temperature for 30 minutes. 2-Fluoro-5,11-dihydrodibenzo[b,e][1,4]oxazepine (538 mg, 2.5 mmol) was added to the suspension, and they were stirred at room temperature for 30 minutes and then at 50° C. for additional 40 minutes. A solution of (S)-1-(4-dimethylaminophenethyl)-3-methanesulfonyloxypyrrolidine (312 mg, 1.0 mmol, prepared by a method disclosed in International Patent No. 0040570A1) in dimethyl sulfoxide (3 ml) was added dropwise to the obtained solution, and they were stirred at 50° C. for 13 hours. The reaction mixture was poured into ice/water and then subjected to the extraction with ethyl acetate. The organic layer was dried and then the solvent was evaporated under reduced pressure. The residue was subjected to the silica gel column chromatography. After the elution with hexane and ethyl acetate (3:1) and then with hexane and ethyl acetate (1:1) as the eluent, suitable fractions were collected and the solvent was evaporated under reduced pressure to obtain (R)-2-fluoro-5,11-dihydro-5-[1-(4-dimethylaminophenethyl)pyrrolidin-3-yl]dibenzo-[b,e][1,4]oxazepine in the form of a light yellow oily substance (140 mg, 32%).

ESI/Mass: 432 [M+H⁺]

NMR (CDCl 3) δ: 1.74-1.84(1H, m), 2.22-2.34(1H, m), 2.37-2.47(1H, m), 2.48-2.71(5H, m), 2.75-2.85(1H, m), 2.90

(6H, s), 3.18(1H, dd, J=7.7, 10. 7 Hz), 4.60-4.70(1H, m), 5.25-5.40(2H, bs), 6.37-6.49(3H, m), 6.72-6.87(5H, m), 6.95-7.24(3H, m),

(R)-2-Fluoro-5,11-dihydro-5-[1-(4-dimethylaminophenethyl)pyrrolidin-3-yl]dibenzo[b,e][1,4]oxazepine dihydrochloride 1.0 ml of 4 M hydrogen chloride/ethyl acetate was added to a solution of (R)-2-fluoro-5,11-dihydro-5-[1-(4-dimethylaminophenethyl)pyrrolidin-3-yl]dibenzo[b,e][1,4]oxazepine (140 mg) in dichloromethane (5 ml), and they were stirred together for 1 hour. The solvent was evaporated under reduced pressure. The obtained residue was solidified by stirring it in hexane and then filtered to obtain the title compound in the form of a light yellow solid (145 mg, 90%).

ESI/Mass: 432 [M+H$^+$]

NMR (CD 3 OD) δ: 1.90-2.08(1H, m), 2.10-2.30(1H, m), 2.38-2.53(1H, m), 2.60-2.73(1H, m), 3.14(2H, t, J=8.0 Hz), 3.26(6H, s), 3.49(2H, t, J=8.0 Hz), 3.60-3.82(2H, m), 4.03-4.14(1H, m), 4.95-5.03(1H, m), 5.06-5.15(1H, m), 6.73-6.92 (3H, m), 7.03-7.26(4H, m), 7.47-7.59(4H, m)

Example 17

(R)-3-Fluoro-5,11-dihydro-5-[1-(4-dimethylaminophenethyl)pyrrolidin-3-yl]dibenzo[b,e][1,4]oxazepine dihydrochloride (R)-3-Fluoro-5,11-dihydro-5-[1-(4-dimethylaminophenethyl)pyrrolidin-3-yl]dibenzo[b,e][1,4]oxazepine was obtained in the same manner as that in Example 16 except that 2-fluoro-5,11-dihydrodibenzo[b,e][1,4]oxazepine was replaced with 3-fluoro-5,11-dihydrodibenzo[b,e][1,4]oxazepine. Light yellow solid. Yield: 40%.

ESI/Mass: 432 [M+H$^+$]

NMR (CDCl 3) δ: 1.73-1.84(1H, m), 2.21-2.30(1H, m), 2.41-2.48(1H, m), 2.50-2.71(5H, m), 2.75-2.82(1H, m), 2.90 (6H, s), 3.18(1H, dd, J=7.7, 10.7 Hz), 5.28(1H, d, J=12.0 Hz), 5.40(1H, d, J=12.0 Hz), 6.48-6.54(1H, m), 6.63-6.72 (4H, m), 7.01-7.12(4H, m), 7.25-7.34(2H, m)

The obtained product was treated with 4 M hydrogen chloride/ethyl acetate in the same manner as that in Example 16 to obtain the title compound in the form of a light brown solid. Yield: 92%.

ESI/Mass: 432 [M+H$^+$]

NMR (CD 3 OD) δ: 1.90-2.07(1H, m), 2.14-2.27(1H, m), 2.42-2.52(1H, m), 2.63-2.77(1H, m), 3.15(2H, t, J=9.0 Hz), 3.26(6H, s), 3.49(2H, t, J=9.0 Hz), 3.64-3.82(2H, m), 4.07-4.16(1H, m), 4.97-5.06(1H, m), 5.10-5.18(1H, m), 6.72-6.94 (4H, m), 7.00-7.09(2H, m), 7.43-7.65(5H, m)

Example 18

(R)-3-Chloro-5,11-dihydro-5-[1-(4-dimethylaminophenethyl)pyrrolidin-3-yl]dibenzo[b,e][1,4]oxazepine dihydrochloride (R)-3-Chloro-5,11-dihydro-5-[1-(4-dimethylaminophenethyl)pyrrolidin-3-yl]dibenzo[b,e][1,4]oxazepine was obtained in the same manner as that in Example 16 except that 3-fluoro-5,11-dihydrodibenzo[b,e][1,4]oxazepine was replaced with 3-chloro-5,11-dihydrodibenzo[b,e][1,4]oxazepine. Light yellow oily substance. Yield: 39%.

ESI/Mass: 448 [M+H$^+$]

NMR (CDCl 3) δ: 1.74-1.84(1H, m), 2.22-2.34(1H, m), 2.37-2.47(1H, m), 2.48-2.71(5H, m), 2.75-2.85(1H, m), 2.90 (6H, s), 3.18(1H, dd, J=7.7, 10. 7 Hz), 4.60-4.70(1H, m), 5.25-5.40(2H, bs), 6.68(2H, d, J=9.7 Hz), 6.71-6.88(4H, m), 6.92-7.10(3H, m) 7.04(2H, d, J=9.7 Hz)

The obtained product was treated with 4 M hydrogen chloride/ethyl acetate in the same manner as that in Example 16 to obtain the title compound in the form of a brown solid. Yield: 90%.

ESI/Mass: 448 [M+H $^+$]

NMR (CD 3 OD) δ: 1.86-2.08(1H, m), 2.10-2.27(1H, m), 2.40-2.53(1H, m), 2.60-2.74(1H, m), 3.12(2H, t, J=9.0 Hz), 3.27(6H, s), 3.50(2H, t, J=9.0 Hz), 3.64-3.84(2H, m), 4.06-4.16(1H, m), 5.00-5.08(1H, m), 5.10-5.19(1HH, m), 6.73-7.07(4H, m), 7.17-7.42(3H, m), 7.47-7.67(4H, m)

Example 19

(R)-3-Fluoro-5,11-dihydro-5-[1-(3-pyrrolidinophenethyl)pyrrolidin-3-yl]-dibenzo[b,e][1,4]oxazepine dihydrochloride

(S)-3-Methanesulfonyloxy-1-(3-pyrrolidinophenethyl)pyrrolidine

3-Pyrrolidinophenethyl mesylate (1.80 g, 4.00 mmol), (S)-3-pyrrolidinol hydrochloride (0.50 g, 4.05 mmol) and potassium carbonate (1.70 g, 12.3 mmol) were added to acetonitrile (20 ml), and they were stirred at 100° C. for 12 hours. Acetonitrile was evaporated under reduced pressure, and the residue was distributed into water and ethyl acetate. The intended product was extracted from the ethyl acetate layer with 1 M hydrochloric acid. After neutralizing the aqueous layer, the product was again extracted with ethyl acetate. The organic layer was dried and then the solvent was evaporated under reduced pressure to quantitatively obtain (S)-3-hydroxy-1-(3-pyrrolidinophenethyl)pyrrolidine in the form of a light yellow solid. This product was dissolved in dichloromethane (10 ml). Triethylamine (0.76 ml, 5.49 mmol) and methanesulfonyl chloride (0.39 ml, 5.03 mmol) were added to the obtained solution at 0° C. and they were stirred overnight. The reaction mixture was distributed into 5% aqueous sodium hydrogencarbonate solution and dichloromethane. The organic layer was dried and then the solvent was evaporated under reduced pressure. The residue was subjected to the silica gel column chromatography. After the elution with chloroform and methanol (95:5), suitable fractions were collected and the solvent was evaporated under reduced pressure to obtain (R)-3-methanesulfonyloxy-1-(3-pyrrolidinophenethyl)pyrrolidine in the form of a light yellow oily substance (1.30 g, 96%).

ESI/Mass: 339 [M+H$^+$]

NMR (CDCl 3) δ: 1.99(4H, m), 2.03-2.15(1H, m), 2.25-2.38(1H, m), 2.44-2.54(1H, m), 2.70-2.80(4H, m), 2.80-3.02 (3H, m), 3.02(3H, s), 3.23-3.30(4H, m), 5.23(1H, m), 6.42 (2H, m), 6.50(1H, d, J=7.5 Hz), 7.14(1H, t, J=7.5 Hz)

(R)-3-Fluoro-5,11-dihydro-5-[1-(3-pyrrolidinophenethyl)pyrrolidin-3-yl]-dibenzo[b,e][1,4]oxazepine 60% sodium hydride (88 mg, 2.2 mmol) was washed with hexane in argon gas stream and then suspended in dimethyl sulfoxide (10 ml). The obtained suspension was stirred at room temperature for 30 minutes. 3-Fluoro-5,11-dihydrodibenzo[b,e][1,4]oxazepine (0.43 g, 2.0 mmol) was added to the suspension, and they were stirred at room temperature for 30 minutes. After stirring at 50° C. for 30 minutes, a solution of (S)-methanesulfonyloxy-1-(3-pyrrolidinophenethyl)pyrrolidine (0.34 g, 1.0 mmol) in dimethyl sulfoxide (4 ml) was added dropwise to the obtained solution, and they were stirred at 70° C. for 2 hours. The reaction mixture was distributed into saturated aqueous sodium chloride solution and ethyl acetate. The organic layer was dried and the solvent was evaporated under reduced pressure. The residue was subjected to the silica gel column chromatography. After the elution with hexane and ethyl acetate (1:1) as the eluent, suitable fractions were collected and the solvent was evaporated under reduced pressure to obtain (R)-3-fluoro-5,11-dihydro-5-[1-(3-pyrrolidinophenethyl)pyrrolidin-3-yl]dibenzo[b,e]-[1,4]oxazepine in the form of a light yellow oily substance (0.19 g, 42%).

ESI/Mass:458[M+H$^+$]

NMR (CDCl 3) δ: 1.68-1.84(1H, m), 1.90-1.99(4H, m), 2.22-2.36(1H, m), 2.40-2.48(1H, m), 2.50-2.76(5H, m), 2.76-2.86(1H, m), 3.16-3.28(5H, m), 4.64(1H, m), 5.36(2H, m), 6.37-6.49(3H, m), 6.72-6.87(5H, m), 6.95(1H, d, J=6.6 Hz), 7.12-7.28(1H, t, J=7.5 Hz), 7.28(1H, d, J=6.6 Hz)

The obtained product was treated with 4 M hydrogen chloride/ethyl acetate in the same manner as that in Example 16 to obtain the title compound in the form of a brown solid (69%).

NMR (CD 3 OD) δ: 1.90-2.08(1H, m), 2.10-2.30(5H, m), 2.35-2.55(1H, m), 2.60-2.78(2H, m), 3.12(2H, t, J=8.1 Hz), 3.30-3.48(1H, m), 3.53(1H, t, J=8.1 Hz), 3.60-3.83(6H, m), 4.95-5.15(2H, m), 6.70-7.10(6H, m), 7.25-7.53(5H, m)

Example 20

(R)-3-Chloro-5,11-dihydro-5-[1-(3-pyrrolidin-1-ylphenethyl)pyrrolidin-3-yl]dibenzo[b,e][1,4]oxazepine dihydrochloride (R)-3-Chloro-5,11-dihydro-5-[1-(3-pyrrolidin-1-ylphenethyl)pyrrolidin-3-yl]dibenzo[b,e][1,4]oxazepine was obtained in the form of a light yellow oily substance from 3-chloro-5,11-dihydrodibenzo[b,e][1,4]oxazepine and (R)-3-methylsulfonyl-1-(3-pyrrolidin-1-ylphenethyl)pyrrolidine in the same manner as that in Example 19(0.20 g, 43%).

ESI/Mass:474[M+H$^+$]

NMR (CDCl 3) δ: 1.63-1.80(1H, m), 1.92-2.00(4H, m), 2.22-2.36(1H, m), 2.40-2.48(1H, m), 2.52-2.75(5H, m), 2.75-2.86(1H, m), 3.15-3.30(5H, m), 4.60-4.70(1H, m), 5.38 (2H, brs), 6.37-6.49(3H, m), 6.72-6.80(3H, m), 6.95(1H, dd, J=1.8, 7.8 Hz), 7.04-7.14(3H, m), 7.24(1H, d, J=7.8 Hz)

The obtained product was treated with 4 M hydrogen chloride/ethyl acetate in the same manner as that in Example 16 to obtain the title compound in the form of a brown solid (93%).

ESI/Mass:474 [M+H$^+$]

NMR (CD 3 OD) δ: 1.90-2.10(1H, m), 2.13-2.32(5H, m), 2.37-2.55(1H, m), 2.60-2.78(2H, m), 3.10(2H, t, J=7.8 Hz), 3.30-3.45(1H, m), 3.53(1H, t, J=7.8 Hz), 3.58-3.81(5H, m), 4.00-4.12(1H, m), 4.95-5.18(2H, m), 6.70-7.10(4H, m), 7.16-7.50(7H, m)

Example 21

(R)-5,11-Dihydro-5-[1(3-pyrrolidinophenethyl)pyrrolidin-2-ylmethyl]-dibenzo[b,e][1,4]oxazepine dihydrochloride (R)-5,11-Dihydro-5-[1-(3-pyrrolidinophenethyl)pyrrolidin-2-ylmethyl]-dibenzo[b,e][1,4]oxazepine (R)-5,11-dihydro-5-(2-pyrrolidylmethyl)dibenzo[b,e][1,4]oxazepine (240 mg, 0.85 mmol, prepared by a method disclosed in International Patent No. 9912925A1), 3-pyrrolidinophenethyl mesylate (253 mg, 0.94 mmol), sodium carbonate (106 mg, 1.0 mmol) and sodium iodide (10 mg, 0.07 mmol) were added to acetonitrile (20 ml), and they were heated at 90° C. under reflux for 6.5 hours. The solvent was evaporated under reduced pressure, and the residue was distributed into ethyl acetate and saturated aqueous sodium hydrogencarbonate solution. The organic layer was washed with water and then dried over magnesium sulfate. The solvent was evaporated under reduced pressure. The obtained residue was subjected to the silica gel column chromatography. After the elution with hexane and ethyl acetate (15:1) and then with hexane and ethyl acetate (2:1) as the eluent, suitable fractions were collected and the solvent was evaporated under reduced pressure to obtain (R)-5,11-dihydro-5-[1-(3-pyrrolidinophenethyl)pyrrolidin-2-ylmethyl]dibenzo[b,e][1,4]oxazepine in the form of a light yellow oily substance (208 mg, 54%).

ESI/Mass: 454 [M+H$^+$]

NMR (CDCl 3) δ: 1.65-1.88(4H, m), 1.99-2.05(4H, m), 2.23-2.32(1H, m), 2.55-2.64(1H, m), 2.71-2.84(3H, m), 3.06-3.16(1H, m), 3.19-3.24(1H, m), 3.28-3.32(4H, m), 3.37 (1H, dd, J=11.0, 14.3 Hz), 4.15(1H, dd, J=4.0, 14.3 Hz), 5.22(1H, d, J=13.0 Hz), 5.34(1H, d, J=13.0 Hz), 6.44-6.55 (3H, m), 6.75-6.83(3H, m), 7.00-7.20(4H, m), 7.26-7.32(2H, m)

(R)-5,11-Dihydro-5-[1-(3-pyrrolidinophenethyl)pyrrolidin-2-ylmethyl]-dibenzo[b,e][1,4]oxazepine dihydrochloride 2.0 ml of 2 M hydrogen chloride/diethyl ether was added to a solution of (R)-5,11-dihydro-5-[1-(3-pyrrolidinophenethyl)pyrrolidin-2-ylmethyl]dibenzo[b,e][1,4]oxazepine (208 mg) in dichloromethane (2 ml), and they were stirred together for 2 hours. The solvent was evaporated under reduced pressure. The obtained residue was solidified by stirring it in hexane. The solid thus precipitated was taken by the filtration to obtain the title compound in the form of a light brown solid (220 mg, 91%).

ESI/Mass: 4 5 4 [M+H$^+$]

NMR (CDCl 3) δ: 1.90-2.42(8H, m), 2.98-3.30(3H, m), 3.40-3.90(8H, m), 4.18-4.35(1H, m), 4.62-4.76(1H, m), 5.14 (1H, d, J=13.0 Hz), 5.30(1H, d, J=13.0 Hz), 6.78-6.94(3H, m), 6.97-7.16(3H, m), 7.20-7.40(4H, m), 7.45(1H, s), 7.59 (1H, s)

Example 22

(R)-5,11-dihydro-5-[1-(4-pyrrolidinophenethyl)pyrrolidin-3-yl]dibenzo-[b,e][1,4]oxazepine dihydrochloride (S)-3-Hydroxy-1-(4-pyrrolidinophenethyl)pyrrolidine 4-Pyrrolidinophenethyl mesylate (13.45 g, 50.0 mmol), (S)-3-pyrrolidinol hydrochloride (5.56 g, 45.0 mmol) and potassium carbonate (18.63 g, 135 mmol) were added to acetonitrile (200 ml), and they were heated at 90° C. for 3 hours. The reaction mixture was cooled and then filtered. The filtrate was evaporated to dryness under reduced pressure, and the residue was distributed into water and ethyl acetate. The intended product was extracted from the ethyl acetate layer with 1 M hydrochloric acid. The aqueous layer was neutralized and then the product was again extracted with ethyl acetate. The organic layer was dried and the solvent was evaporated under reduced pressure to obtain (S)-3-hydroxy-1-(4-pyrrolidinophenethyl)pyrrolidine in the form of a light yellow solid (6.30 g, 52%).

NMR (CDCl 3) δ: 1.74-1.84(1H, m), 1.96-2.04(4H, m), 2.15-2.25(1H, m), 2.34-2.43(1H, m), 2.55-2.63(1H, m), 2.65-2.80(5H, m), 2.92-3.03(1H, m), 3.23-3.28(4H, m), 4.33-4.40(1H, m), 6.51(2H, d, J=9.3 Hz), 7.06(2H, d, J=9.3 Hz)

(S)-3-Methanesulfonyloxy-1-(4-pyrrolidinophenethyl)pyrrolidine (S)-3-Hydroxy-1-(4-pyrrolidinophenethyl)pyrrolidine (6.30 g, 23.4 mmol) was dissolved in 100 ml of dichloromethane. Diisopropylethylamine (5.28 ml, 30.0 mmol) and methanesulfonyl chloride (2.34 ml, 30.0 mmol) were added to the obtained solution at 0° C. and they were stirred for 4 hours. The reaction mixture was distributed into 5% aqueous sodium hydrogencarbonate solution and dichloromethane. The organic layer was dried and the solvent was evaporated under reduced pressure. The residue was subjected to the silica gel column chromatography. After the elution with dichloromethane and methanol (10:1), suitable fractions were collected and the solvent was evaporated under reduced pressure to obtain (S)-3-methanesulfonyloxy-1-(4-pyrrolidinophenethyl)pyrrolidine in the form of a light yellow oily substance (7.50 g, 49%).

ESI/Mass: 339 [M+H$^+$]

NMR (CDCl 3) δ: 1.96-2.00(4H, m), 2.04-2.16(1H, m), 2.27-2.38(1H, m), 2.44-2.52(1H, m), 2.65-2.74(4H, m), 2.82-2.98(3H, m), 3.02(3H, s), 3.23-3.28(4H, ), 5.19-5.27(1H, m), 6.50(2H, d, J=9.3 Hz), 7.05(2H, d, J=9.3 Hz)

(R)-5,11-Dihydro-5-[1-(4-pyrrolidinophenethyl)pyrrolidin-3-yl]dibenzo-[b,e][1,4]oxazepine dihydrochloride 60% sodium hydride (132 mg, 3.3 mmol) was washed with hexane in argon stream and then suspended in dimethyl sulfoxide (10 ml), and the obtained suspension was stirred at room temperature for 30 minutes. 5,11-Dihydrodibenzo[b,e][1,4]oxazepine (600 mg, 3.0 mmol) was added to the suspension, and they were stirred at room temperature for 30 minutes and then at 50° C. for additional 30 minutes. A solution of (S)-3-methanesulfonyloxy-1-(4-pyrrolidinophenethyl)pyrrolidine (340 mg, 1.0 mmol) in dimethyl sulfoxide (5 ml) was added dropwise to the obtained solution, and they were stirred at 50° C. for 42 hours. The reaction mixture was distributed into saturated aqueous sodium chloride solution and ethyl acetate. The organic layer was dried and the solvent was evaporated under reduced pressure. The residue was subjected to the silica gel column chromatography. After the elution with hexane and ethyl acetate (3:1), suitable fractions were collected and the solvent was evaporated under reduced pressure to obtain (R)-5,11-dihydro-5-[1-(4-pyrrolidinophenethyl)pyrrolidin-3-yl]dibenzo[b,e][1,4]oxazepine in the form of a light yellow oily substance (142 mg, 32%).

NMR (CDCl 3) δ: 1.72-1.84(1H, m), 1.96-2.04(4H, m), 2.22-2.41(2H, m), 2.49-2.71(5H, m), 2.80-2.89(1H, m), 3.22-3.27(5H, m), 4.67-4.74(1H, m), 5.30-5.50(2H, b), 6.48(2H, d, J=9.7 Hz), 6.72-6.82(3H, m), 6.95-7.13(3H, m), 7.02(2H, d, J=9.7 Hz), 7.26-7.33(2H, m)

The obtained product was treated with 2 M hydrogen chloride/diethyl ether in the same manner as that in Example 21 to obtain the title compound in the form of a brown solid (83%).

ESI/Mass: 440 [M+H$^+$]

NMR (CD 3 OD) δ: 1.90-2.08(1H, m), 2.10-2.30(5H, m), 2.35-2.55(1H, m), 2.60-2.78(2H, m), 3.08(2H, t, J=10.0 Hz), 3.23-3.38(1H, m), 3.47(1H, t, J=10.0 Hz), 3.60-3.83(5H, m), 4.02-4.11(1H, m), 4.99-5.08(1H, m), 5.10-5.18(1H, m), 6.72-7.04(4H, m), 7.15-7.24(2H, m), 7.36-7.44(6H, m)

Example 23

(R)-5,11-Dihydro-5-[1-(3-pyrrolidinophenethyl)pyrrolidin-3-yl]dibenzo-[b,e][1,4]oxazepine dihydrochloride (S)-3-Hydroxy-1-(3-pyrrolidinophenethyl)pyrrolidine 3-Pyrrolidinophenethyl mesylate (1.80 g, 4.00 mmol) synthesized in Example 21, (S)-3-pyrrolidinol hydrochloride (0.50 g, 4.05 mmol) and potassium carbonate (1.70 g, 12.3 mmol) were added to acetonitrile (20 ml), and they were heated at 100° C. for 12 hours. Acetonitrile was evaporated under reduced pressure, and the residue was distributed into water and ethyl acetate. The intended product was extracted from the ethyl acetate layer with 1 M hydrochloric acid. The extract was neutralized and then the product was extracted with ethyl acetate. The organic layer was dried and the solvent was evaporated under reduced pressure to obtain (S)-3-hydroxy-1-(3-pyrrolidinophenethyl)pyrrolidine in the form of a light yellow solid (1.04 g, 100%).

NMR (CDCl 3) δ: 1.68-1.80(1H, m), 1.91-2.02(4H, m), 2.13-2.25(1H, m), 2.30-2.40(1H, m), 2.55-2.63(1H, m), 2.67-2.80(5H, m), 2.89-2.98(1H, m), 3.15-3.25(4H, m), 4.28-4.39(1H, m), 6.39-6.42(2H, m), 6.50(1H, d, J=8.0 Hz), 7.13(1H, t, J=8.0 Hz)

(S)-3-Methanesulfonyloxy-1-(3-pyrrolidinophenethyl)pyrrolidine (S)-3-Hydroxy-1-(3-pyrrolidinophenethyl)pyrrolidine (1.04 g, 4.00 mmol) was dissolved in dichloromethane (10 ml). Triethylamine (0.76 ml, 5.49 mmol) and methanesulfonyl chloride (0.39 ml, 5.03 mmol) were added to the obtained solution at 0° C. and they were stirred overnight. The reaction mixture was distributed into 5% aqueous sodium hydrogencarbonate solution and dichloromethane. The organic layer was dried and the solvent was evaporated under reduced pressure. The residue was subjected to the silica gel column chromatography. After the elution with chloroform and methanol (95:5), suitable fractions were collected and the solvent was evaporated under reduced pressure to obtain (S)-3-methanesulfonyloxy-1-(3-pyrrolidinophenethyl)pyrrolidine in the form of a light yellow oily substance (1.30 g, 96%).

ESI/Mass: 339 [M+H$^+$]

NMR (CDCl 3) δ: 1.96-2.02(4H, m), 2.03-2.15(1H, m), 2.25-2.38(1H, m), 2.44-2.54(1H, m), 2.70-2.80(4H, m), 2.80-3.02(3H, m), 3.02(3H, s), 3.23-3.30(4H, m), 5.20-5.28(1H, m), 6.42(2H, m), 6.50(1H, d, J=7.5 Hz), 7.14(1H, t, J=7.5 Hz)

(R)-5,11-Dihydro-5-[1-(3-pyrrolidinophenethyl)pyrrolidin-3-yl]dibenzo-[b,e][1,4]oxazepine dihydrochloride 60% sodium hydride (132 mg, 3.3 mmol) was washed with hexane in argon stream and then suspended in dimethyl sulfoxide (10 ml), and the obtained suspension was stirred at room temperature for 30 minutes. 5,11-Dihydrodibenzo[b,e][1,4]oxazepine (600 mg, 3.0 mmol) was added to the suspension, and they were stirred at room temperature for 30 minutes and then at 50° C. for additional 30 minutes. A solution of (S)-3-methanesulfonyloxy-1-(4-pyrrolidinophenethyl)pyrrolidine (340 mg, 1.0 mmol) in dimethyl sulfoxide (5 ml) was added dropwise to the obtained solution, and they were stirred at 50° C. for 42 hours. The reaction mixture was distributed into saturated aqueous sodium chloride solution and ethyl acetate. The organic layer was dried and the solvent was evaporated under reduced pressure. The residue was subjected to the silica gel column chromatography. After the elution with hexane and ethyl acetate (3:1), suitable fractions were collected and the solvent was evaporated under reduced pressure to obtain (R)-5,11-dihydro-5-[1-(3-pyrrolidinophenethyl)pyrrolidin-3-yl]dibenzo[b,e][1,4]oxazepine in the form of a light yellow oily substance (225 mg, 51%).

ESI/Mass: 440 [M+H$^+$]

NMR (CDCl$_3$) δ: 1.74-1.84(1H, m), 1.95-2.00(4H, m), 2.23-2.34(1H, m), 2.34-2.43(1H, m), 2.49-2.57(1H, m), 2.61-2.76(5H, m), 2.81-2.88(1H, m), 3.23-3.29(4H, m), 4.67-4.76(1H, m), 5.30-5.50(2H, bs), 6.34-6.48(3H, m), 6.71-6.85(3H, m), 6.94-6.97(1H, m), 7.04-7.16(3H, m), 7.25-7.32(2H, m)

The obtained product was treated with 2 M hydrogen chloride/diethyl ether in the same manner as that in Example 21 to obtain the title compound in the form of a brown solid (78%).

ESI/Mass: 440 [M+H$^+$]

NMR (CD$_3$OD) δ: 1.90-2.08(1H, m), 2.10-2.30(5H, m), 2.35-2.55(1H, m), 2.60-2.78(1H, m), 3.10(2H, t, J=10.0 Hz), 3.25-3.40(1H, m), 3.25(2H, t, J=10.0 Hz), 3.60-3.80(5H, m), 4.03-4.12(1H, m), 4.99-5.09(1H, m), 5.11-5.19(1H, m), 6.70-7.04(5H, m), 7.14-7.47(7H, m)

Example 24

5,11-Dihydro-5-[2-[N-methyl-N-(3-pyrrolidinophenethyl)amino]ethyl]-dibenzo[b,e][1,4]oxazepine dihydrochloride 5,11-Dihydro-5-[2-(N-methylamino)ethyl]dibenzo[b,e][1,4]oxazepine (254 mg, 1.00 mmol, prepared by a method disclosed in International Patent No. 0040570A1), 3-pyrrolidinophenethyl mesylate (296 mg, 1.10 mmol), sodium carbonate (138 mg, 1.30 mmol) and sodium iodide (20 mg, 0.13 mmol) were added to acetonitrile (20 ml), and they were heated at 90° C. under reflux for 6.5 hours. The solvent was evaporated under reduced pressure, and the residue was distributed into ethyl acetate and saturated aqueous sodium hydrogencarbonate solution. The organic layer was washed with water and then dried over magnesium sulfate. The solvent was evaporated under reduced pressure. The obtained residue was subjected to the silica gel column chromatography. After the elution with hexane and ethyl acetate (10:1) and then with hexane and ethyl acetate (3:1) as the eluent, suitable fractions were collected and the solvent was evaporated under reduced pressure to obtain 5,11-dihydro-5-[2-[N-methyl-N-(3-pyrrolidinophenethyl)amino]-ethyl]dibenzo[b,e][1,4]oxazepine in the form of a light yellow oily substance (331 mg, 78%).

ESI/Mass: 428 [M+H$^+$]

NMR (CDCl$_3$) δ: 1.96-2.00(4H, m), 2.32(3H, s), 2.61 (4H, s), 2.66(2H, t, J=8.0 Hz), 3.23-3.27(4H, m), 3.90(2H, t, J=8.0 Hz), 5.29(2H, s), 6.32-6.44(3H, m), 6.77-6.84(3H, m), 7.00-7.14(4H, m), 7.25-7.32(2H, m)

The obtained product was treated with 2 M hydrogen chloride/diethyl ether in the same manner as that in Example 21 to obtain the title compound in the form of a brown solid (81%).

ESI/Mass: 428 [M+H$^+$]

NMR (CDCl$_3$) δ: 2.28-2.40(4H, m), 2.85(3H, d, J=4.3 Hz), 3.10-3.48(6H, m), 3.55-3.74(4H, m), 4.23-4.35(1H, m), 4.40-4.52(1H, m), 5.23(1H, d, J=14.3 Hz), 5.25(1H, d, J=14.3 Hz), 6.82-6.93(3H, m), 7.06-7.11(2H, m), 7.18(1H, d, J=8.7 Hz), 7.24-7.44(4H, m), 7.53(1H, d, J=8.7 Hz), 7.78(1H, m)

Example 25

(R)-3-Chloro-5,11-dihydro-5-[1-(4-dimethylaminophenethyl)pyrrolidin-2-ylmethyl]dibenzo[b,e][1,4]oxazepine dihydrochloride (=compound of Example 8)

Methyl ester of N-[(4-dimethylaminophenyl)acetyl]-D-proline

1-Hydroxybenzotriazole monohydrate (6.1 g, 45.4 mmol) and N-dimethylaminopropyl-N'-ethylcarbodiimide hydrochloride (8.7 g, 45.4 mmol) were added to a solution of (4-dimethylaminohenyl)acetic acid (7.4 g, 41.3 mmol) and methyl ester hydrochloride of D-proline (7.19 g, 43.4 mmol) in methylene chloride (150 ml). The obtained mixture was stirred at room temperature for 6 hours. Triethylamine (6.3 ml, 45.4 mmol) was added to the mixture. They were stirred at room temperature overnight and the reaction mixture was successively washed with water (200 ml), 5% aqueous sodium hydrogencarbonate solution (200 ml) and water (200 ml). The solvent was evaporated under reduced pressure. The obtained residue was subjected to the silica gel column chromatography. After the elution with methylene chloride and methanol (10:1), suitable fractions were collected and the solvent was evaporated under reduced pressure to obtain the title compound in the form of a brown oily substance (11.0 g, 83%).

ESI/Mass: 291 [M+H$^+$]

NMR (CDCl$_3$) δ: 1.82-2.26(4H, m), 2.82-2.98(6H, m), 3.40-3.76(2H, m), 3.60(3H, s), 3.73(2H, s), 4.41-4.52(1H, m), 6.64-6.74(2H, m), 7.07-7.19(2H, m)

N-[(4-dimethylaminophenyl)acetyl]-D-proline

Methyl ester of N-[(4-dimethylaminophenyl)acetyl]-D-proline (1.0 g, 3.4 mmol) was dissolved in tetrahydrofuran (10 ml). Water (10 ml) and 1 M aqueous sodium hydroxide solution (3.7 ml, 3.7 mmol) were added to the obtained solution. They were stirred at room temperature overnight. A saturated aqueous ammonium chloride solution (15 ml) was added to the reaction mixture, and they were adjusted to around pH 4 with 1 M hydrochloric acid. After the solvent was evaporated from the mixture under reduced pressure, acetone was added to the residue and they were stirred. The reaction mixture was filtered to obtain the filtrate. The solvent was evaporated under reduced pressure and the residue was dried to obtain the title compound in the form of a yellow solid (0.91 g, 96%).

ESI/Mass: 277 [M+H$^+$]

NMR (CDCl$_3$) δ: 1.80-2.28(3H, m), 2.45-2.58(1H, m), 2.95(6H, s), 3.42-3.70(2H, m), 3.65(2H, s), 4.60-4.68(1H, m), 6.72-6.83(2H, m), 7.08-7.19(2H, m)

(R)-1-[(4-dimethylaminophenyl)acetyl]pyrrolidine-2-carboxylic acid [2-(2-bromo-4-chlorobenzyloxy)phenyl]amide Toluene (111 ml) and N-methylmorpholine (3.85 ml, 35.0 mmol) were added to N-[(4-dimethylaminophenyl)acetyl]-D-proline (8.56 g, 31.0 mmol). Ethyl chloroformate (3.26 ml, 34.1 mmol) was added to the obtained mixture, and they were stirred for 2 hours. 2-(2-Bromo-4-chlorobenzyloxy)aniline hydrochloride (10.8 g, 31.0 mmol) and N-methylmorpholine (4.09 ml, 37.2 mmol) were added thereto and they were stirred at room temperature overnight. Water (40 ml) was added to the reaction mixture. The organic layer was washed with water (40 ml) and then dried over sodium sulfate. The solvent was evaporated under reduced pressure. The residue was subjected to the silica gel column chromatography. After the elution with methylene chloride and methanol (30:1), suitable fractions were collected and the solvent was evaporated under reduced pressure to obtain the title compound in the form of a yellow solid (16.3 g, 92%).

ESI/Mass: 572 [M+H$^+$]

NMR (CDCl$_3$) δ: 1.80-1.94(1.2H, m), 1.96-2.06(0.8H, m), 2.08-2.36(1.2H, m), 2.51-2.59(0.8H, m), 2.79 and 2.92 (total 6.0H, each s), 3.45-3.75(4H, m), 4.53-4.59(0.2H, m), 4.81-4.87(0.8H, m), 4.94-5.13(0.3H, m), 5.13(1.7H, s), 6.47-6.69(2.0H, m), 6.84-7.14(5.1H, m), 7.19-7.26(0.9H, m), 7.51-7.68(1.9H, m), 8.26(0.1H, br s), 8.35-8.42(1.0H, m), 9.53(1H, br s)

(R)-{[2-(3-chloro-5,11-dihydrodibenzo[b,e][1,4]oxazepine-5-carbonyl)-pyrrolidine]-1-yl}-2-(4-dimethylaminophenyl)ethanone Potassium carbonate (1.27 g, 9.19 mmol), copper bromide (I) (24.1 mg, 0.168 mmol) and 4-picoline (8.65 ml) were added to (R)-1-[(4-dimethylaminophenyl)acetyl]pyrrolidine-2-carboxylic acid [2-(2-bromo-4-chlorobenzyloxy)phenyl]amide (1.73 g, 3.03 mmol). They were heated at 145° C. for 20 hours and then filtered. The solvent was evaporated from the filtrate under reduced pressure. The residue was subjected to the silica gel column chromatography. After the elution with methylene chloride and methanol (20:1), suitable fractions were collected and the solvent was evaporated under reduced pressure to obtain the title compound in the form of a brown solid (0.97 g, 66%).

ESI/Mass: 490 [M+H$^+$]

NMR (CDCl$_3$) δ: 1.52-2.34(4H, m), 2.92 and 2.96(total 6.0H, each s), 3.44-3.77(4.1 H, m), 4.34-4.41(0.2H, m), 4.65-4.72(0.4H, m), 4.77-4.91(1.1H, m), 5.08-5.15(0.2H, m), 5.50-5.67(0.3H, m), 6.34-6.41(0.7H, m), 6.65-7.03 (4.0H, m), 7.06-7.50(6.5H, m), 7.59(0.2H, br s), 7.91-7.96 (0.2H, m), 8.11(0.1H, br s)

(R)-3-Chloro-5,11-dihydro-5-[1-(4-dimethylaminophenethyl)pyrrolidin-2-ylmethyl]dibenzo[b,e][1,4]oxazepine (R)-{[2-(3-chloro-5,11-dihydrodibenzo[b,e][1,4]oxazepine-5-carbonyl)-pyrrolidine]-1-yl}-2-(4-dimethylaminophenyl)ethanone (0.97 g, 1.98 mmol) was dissolved in tetrahydrofuran (19.4 ml). Sodium borohydride (0.39 g, 10.4 mmol) was added to the resultant solution. Then boron trifluoride/tetrahydrofuran complex (1.69 ml, 13.9 mmol) was added to the obtained mixture in an ice bath. The reaction mixture was heated at 37° C. for 42 hours. Sodium borohydride (0.056 g, 1.5 mmol) and boron trifluoride/tetrahydrofuran complex (0.24 ml, 1.99 mmol) were added thereto. The reaction mixture was heated at 37° C. for 24 hours. 1.5 M aqueous sodium hydroxide solution (16 ml, 24 mmol) was added thereto under cooling in the ice bath. The reaction mixture was heated at 60° C. for 12 hours and then distributed into toluene (20 ml) and water (10 ml). The organic layer was taken. Tetrahydrofuran was evaporated under reduced pressure. The residue was washed with water (10 ml) and then the solvent was evaporated under reduced pressure. The residue was subjected to the silica gel column chromatography. After the elution with methylene chloride and methanol (10:1), suitable fractions were collected and the solvent was evaporated under reduced pressure to obtain the title compound in the form of a brown solid (0.67 g, 74%)

ESI/Mass: 462 [M+H$^+$]

NMR (CDCl$_3$) δ: 1.59-1.90(4H, m), 2.22-2.31(1H, m), 2.50-2.59(1H, m), 2.66-2.84(3H, m), 2.93(6H, s), 2.97-3.06 (1H, m), 3.16-3.24(1H, m), 3.34(1H, dd, J=13.0, 9.4 Hz), 4.07(1H, dd, J=13.0, 3.7 Hz), 5.22(2H, s), 6.70-6.75(2H, m), 6.75-6.86(3H, m), 6.97-7.02(2H, m), 7.08-7.14(3H, m), 7.17 (1H, d, J=7.9 Hz)

(R)-3-Chloro-5,11-dihydro-5-[1-(4-dimethylaminophenethyl)pyrrolidin-2-ylmethyl]dibenzo[b,e][1,4]oxazepine dihydrochloride (R)-3-Chloro-5,11-dihydro-5-[1-(4-dimethylaminophenethyl)pyrrolidin-2-ylmethyl]dibenzo[b,e][1,4]oxazepine (10.6 g, 22.9 mmol) was dissolved in 2-propanol (100 ml). 4 M hydrogen chloride/2-propanol (22.9 ml) was added to the obtained solution. The solvent was evaporated under reduced pressure, and 4 M hydrogen chloride/2-propanol (11.5 ml) was added to the residue. The solvent was evaporated under reduced pressure to obtain the title compound in the form of a light yellow solid (12.9 g, 100%).

ESI/Mass: 462 [M+H$^+$]

NMR (CDCl$_3$) δ: 2.00-2.21(2H, m), 2.21-2.34(2H, m), 2.86-2.98(1H, m), 3.03-3.15(1H, m), 3.19(6H, s), 3.15-3.30 (1H, m), 3.47-3.70(3H, m), 3.90-4.00(1H, m), 4.24(1H, dd, J=14.0, 7.2 Hz), 4.65(1H, dd, J=14.0, 6.0 Hz), 5.12(1H, d, J=12.7 Hz), 5.40(1H, d, 12.7 Hz), 6.87(1H, dd, J=7.8, 1.9 Hz), 6.89-7.00(2H, m), 7.03-7.09(2H, m), 7.14(1H, d, J=1.9 Hz), 7.18(1H, d, J=8.0 Hz), 7.45(2H, d, J=8.4 Hz), 7.79(2H, d, J=8.6 Hz)

Example 26

(R)-2-Fluoro-5,11-dihydro-5-[1-(4-pyrrolidinophenethyl)pyrrolidin-2-yl-methyl]dibenzo[b,e][1,4]oxazepine dihydrochloride (=compound of Example 9)

(4-Pyrrolidinophenyl)acetic acid

Toluene (10 ml) was added to a mixture of palladium acetate (22.3 mg, 0.10 mmol), 2-(biphenyl)-di-tert-butylphosphine (59.8 mg, 0.20 mmol) and sodium tert-butoxide (2.40 g, 25.0 mmol), and then (4-bromophenyl)acetic acid (2.15 g, 10.0 mmol) and pyrrolidine (1.10 ml, 13.2 mmol) were added thereto. The obtained mixture was heated at 70° C. for 46 hours. Water (20 ml) was added to the reaction mixture. pH of the aqueous layer was controlled at 2 or below. The aqueous layer was washed with toluene and adjusted to pH 4 to 5. After stirring the reaction mixture in ice-bath for a while, it was filtered to obtain the title compound in the form of a light yellow solid (1.1 g, 54%).

ESI/Mass: 206 [M+H⁺]

NMR (DMSO-d6) δ: 1.90-1.95(4H, m), 3.15-3.20(4H, m), 3.38(2H, s), 6.47(2H, d, J=8.4 Hz), 7.03(2H, d, J=8.4 Hz)

Methyl ester of N-[(4-pyrrolidinophenyl)acetyl]-D-proline

Methylene chloride (20 ml) was added to a mixture of (4-pyrrolidinophenyl) acetic acid (2.05 g, 10.0 mmol) and methyl ester hydrochloride of D-proline (1.66 g, 10.0 mmol). Triethylamine (1.55 ml, 11.1 mmol) and N-dimethylaminopropyl-N'-ethylcarbodiimide hydrochloride (2.11 g, 11.0 mmol) were added thereto. The obtained mixture was stirred at room temperature for 4 hours. Then the reaction mixture was successively washed with water (10 ml), water (5 ml), 5% aqueous citric acid solution (5 ml) and 5% aqueous sodium hydrogencarbonate solution (5 ml). After drying over magnesium sulfate, the solvent was evaporated under reduced pressure to obtain the title compound in the form of a light red solid (3.06 g, 96%).

NMR (CDCl₃) δ: 1.85-2.15(8H, m), 3.23-3.28(4H, m), 3.31-3.68(4H, m), 3.68-3.75(3H, m), 4.40-4.53(1H, m), 6.45-6.54(2H, m), 7.05-7.14(2H, m)

N-[(4-Pyrrolidinophenyl)acetyl]-D-proline

Methyl ester of N-[(4-pyrrolidinophenyl)acetyl]-D-proline (30.1 g, 94.2 mmol) was dissolved in tetrahydrofuran (150 ml). Water (134 ml) and 6 M aqueous sodium hydroxide solution (16.5 ml, 99.2 mmol) were added to the obtained solution. They were stirred at room temperature for 4 hours. 6 M Hydrochloric acid (16.6 ml, 99.7 mmol) was added to the reaction mixture. Tetrahydrofuran was evaporated from the mixture under reduced pressure and then the residue was left to stand in a refrigerator overnight and then filtered. After drying the filter cake under reduced pressure, the title compound was obtained in the form of a light purple solid (23.4 g, 82%).

ESI/Mass: 303 [M+H⁺]

NMR (CDCl₃) δ: 1.85-2.05(7H, m), 2.45-2.55(1H, m), 3.23-3.29(4H, m), 3.45-3.70(4H, m), 4.60-4.64(1H, m), 6.48-6.55(2H, m), 7.07-7.11(4H, m),

(R)-1-[(4-Pyrrolidinophenyl)acetyl]pyrrolidine-2-carboxylic acid [2-(2-bromo-5-fluorobenzyloxy) phenyl]amide Toluene (37.8 ml) and N-methylmorpholine (1.10 g, 10.8 mmol) were added to N-[(4-pyrrolidinophenyl)acetyl]-D-proline (2.90 g, 9.59 mmol). Ethyl chloroformate (1.14 g, 10.5 mmol) was added to the obtained mixture in an ice bath, and they were stirred for 2 hours. 2-(2-Bromo-5-fluorobenzyloxy)aniline hydrochloride (3.19 g, 9.59 mmol) and N-methylmorpholine (1.16 g, 11.5 mmol) were added thereto and the temperature of the obtained mixture was slowly elevated to room temperature for a period of 16 hours. Water (30 ml), citric acid (1.61 g) and toluene (10 ml) were added to the reaction mixture for the distribution. The organic layer was washed with water (10 ml), water (10 ml), 6.7% aqueous sodium hydrogencarbonate solution (10 ml), 6.7% aqueous sodium hydrogencarbonate solution (10 ml), water (10 ml) and water (10 ml). After drying over sodium sulfate, the solvent was evaporated under reduced pressure to obtain the title compound in the form of a light yellow solid (5.13 g, 93%).

ESI/Mass: 580 [M+H⁺]

NMR (CDCl₃) δ: 1.77-2.20(7H, m), 2.48-2.57(1H, m), 3.14-3.25(4H, m), 3.42-3.67(4H, m), 4.80-4.88(1H, m), 5.11 (2H, s), 6.29-6.46(2H, m), 6.80-7.10(6H, m), 7.43-7.61(2H, m), 8.26-8.39(1H, m), 9.57(1H, s)

(R)-{[2-(2-fluoro-5,11-dihydrodibenzo[b,e][1,4] oxazepine-5-carbonyl)-pyrrolidine]-1-yl}-2-(4-pyrrolidinophenyl)ethanone Potassium carbonate (3.58 g, 25.9 mmol), copper bromide (I) (63.5 mg, 0.443 mmol) and 4-picoline (25 ml) were added to (R)-1-[(4-pyrrolidinophenyl)acetyl]pyrrolidine-2-carboxylic acid [2-(2-bromo-5-fluorobenzyloxy)phenyl] amide (5.0 g, 8.61 mmol). They were heated at 145° C. for 21 hours and then filtered to obtain the filtrate. The solvent was evaporated from the filtrate under reduced pressure. The obtained mixture was distributed into toluene and 9.5% aqueous citric acid solution. The organic layer was washed with 9.5% aqueous citric acid solution twice and then dried over sodium sulfate. The solvent was evaporated under reduced pressure. The residue was subjected to the silica gel column chromatography. After the elution with methylene chloride and methanol (97:3), suitable fractions were collected and the solvent was evaporated under reduced pressure to obtain the title compound in the form of a purple solid (4.16 g, 97%).

ESI/Mass: 500 [M+H⁺]

NMR (CDCl₃) δ: 1.60-2.40(8H, m), 3.14-3.35(4H, m), 3.39-3.75(4H, m), 4.29-5.68(3H, m), 6.32-6.60(3H, m), 6.77-8.11(8H, m)

(R)-2-Fluoro-5,11-dihydro-5-[1-(4-pyrrolidinophenethyl)pyrrolidin-2-yl-methyl]dibenzo[b,e][1,4]oxazepine (R)-{[2-(2-fluoro-5,11-dihydrodibenzo[b,e][1,4]oxazepine-5-carbonyl)pyrrolidine]-1-yl}-2-(4-pyrrolidinophenyl)ethanone (3.79 g, 7.59 mmol) was dissolved in tetrahydrofuran (48 ml). Sodium borohydride (1.52 g, 40.2 mmol) was added to the resultant solution. Then boron trifluoride/tetrahydrofuran complex (7.38 g, 49.5 mmol) was added to the obtained mixture in an ice bath. The reaction mixture was heated at 37° C. for 66 hours. 1.5 M aqueous sodium hydroxide solution (48 ml, 75 mmol) was added thereto under cooling in the ice bath. The reaction mixture was heated at 60° C. for 13 hours and then toluene (12 ml) was added thereto. The organic layer was taken. The solvent was evaporated under reduced pressure to obtain 21.0 g of the residue. Toluene (12 ml) was added thereto. The obtained mixture was washed with water (10 ml) twice, and the solvent was evaporated under reduced pressure. The residue was subjected to the silica gel column chromatography. After the elution with methylene chloride and methanol (97:3), suitable fractions were collected and the solvent was evaporated under reduced pressure to obtain the title compound in the form of a purple solid (2.95 g, 82%).

ESI/Mass: 472 [M+H⁺]

NMR (CDCl₃) δ: 1.59-1.90(4H, m), 1.90-2.10(4H, m), 2.18-2.30(1H, m), 2.42-2.58(1H, m), 2.62-2.83(3H, m), 2.92-3.08(1H, m), 3.12-3.38(6H, m), 4.08(1H, dd, J=12.8, 3.0 Hz), 5.16(1H, d, J=11.8 Hz), 5.30(1H, d, J=11.8 Hz), 6.54(2H, d, J=8.5 Hz), 6.72-6.86(3H, m), 6.93-7.12(6H, m)

(R)-2-Fluoro-5,11-dihydro-5-[1-(4-pyrrolidinophenethyl)pyrrolidin-2-yl-methyl]dibenzo[b,e][1,4]oxazepine dihydrochloride (R)-2-Fluoro-5,11-dihydro-5-[1-(4-pyrrolidinophenethyl)pyrrolidin-2-ylmethyl]dibenzo[b,e][1,4]oxazepine (12.04 g, 25.5 mmol) was dissolved in 2-propanol (250 ml). 4 M hydrogen chloride/2-propanol (17.0 ml) was added to the obtained solution and they were stirred at room temperature for 0.5 hour. The solvent was evaporated under reduced pressure, and 2-propanol (about 50 ml) was added to the residue. The solvent was evaporated under reduced pressure repeatedly 4 times to obtain the title compound in the form of a light red solid (14.89 g, 100%).

ESI/Mass: 472 [M+H$^+$]

NMR (DMSO-d6) δ: 1.76-2.19(8H, m), 2.89-3.25(4H, m), 3.33-3.54(5H, m), 3.54-3.67(2H, m), 4.10(1H, dd, J=13.6, 7.5 Hz), 4.39(1H, dd, J=13.6, 6.5 Hz), 5.18(1H, d, J=12.0 Hz), 5.44(1H, d, J=12. 1 Hz), 6.72-6.78(1H, ), 6.83-6.90(2H, m), 6.96-7.27(6H, m), 7.31-7.38(2H, m)

Example 27

(R)-5,11-Dihydro-5-[1-(4-pyrrolidinophenethyl)pyrrolidin-3-yl]dibenzo[b,e][1,4]oxazepine (=compound of Example 22)

(R)-N-[1-(4-Pyrrolidinophenethyl)pyrrolidin-3-yl]-2-(2-bromobenzyloxy)aniline (S)-3-Methanesulfonyloxy-1-(4-pyrrolidinophenethyl)pyrrolidine (0.30 g, 0.89 mmol) was added to 2-(2-bromobenzyloxy)aniline (1.15 g, 4.13 mmol) in argon stream. The obtained mixture was dissolved in acetonitrile (50 ml). Potassium carbonate (1.62 g, 11.7 mmol) was added to the obtained solution, and they were refluxed for 85 hours. Acetonitrile (15 ml) was added to the reaction mixture, and they were refluxed for additional 48 hours. The reaction mixture was filtered through Celite to obtain the filtrate. The solvent was evaporated under reduced pressure to obtain the title compound in the form of a brown oily mixture (1.40 g).

ESI/Mass: 520 [M+H$^+$]

(R)-5,11-Dihydro-5-[1-(4-pyrrolidinophenethyi)pyrrolidin-3-yl]dibenzo-[b,e][1,4]oxazepine Potassium carbonate (1.71 g, 12.4 mmol), copper bromide (I) (53 mg, 0.37 mmol) and toluene (30 ml) were added to (R)-N-[1-(4-pyrrolidinophenethyl)pyrrolidin-3-yl]-2-(2-bromobenzyloxy)aniline (1.4 g as mixture). The reaction mixture was heated under reflux for 53 hours and then copper bromide (I) (60 mg, 0.42 mmol) was added thereto. The reaction mixture was heated under reflux for additional 50 hours. Toluene (10 ml), potassium carbonate (1.04 g, 7.52 mmol) and copper bromide (I) (42 mg, 0.29 mmol) were added thereto. The reaction mixture was heated under reflux for 48 hours and then filtered through Celite. Water was added to the filtrate. The organic layer was taken and dried over sodium sulfate. The solvent was evaporated under reduced pressure. A part (187 mg) of the obtained residue (1.12 g) was subjected to the high performance liquid chromatography. After the elution with acetonitrile and water (gradient from 20:80 to 70:30), suitable fractions were collected and distributed into methylene chloride and saturated aqueous sodium hydrogencarbonate solution. The organic layer was dried over sodium sulfate, and the solvent was evaporated under reduced pressure. The residue was subjected to the thin layer silica gel chromatography. After the development with hexane and ethyl acetate (1:5), silica gel was collected from proper parts and then eluted with a solvent mixture of methylene chloride and methanol (3:1). The effluents were collected, and he solvent was evaporated under reduced pressure to obtain the title compound in the form of a white solid (25.5mg, yield in 2 steps: 39%).

ESI/Mass: 440 [M+H$^+$]

NMR (CDCl$_3$) δ: 1.72-1.84(1H, m), 1.92-2.05(4H, m), 2.24-2.49(2H, m), 2.49-2.77(5H, m), 2.82-2.94(1H, m), 3.18-3.36(5H, m), 4.68-4.79(1H, m), 5.19-5.62(2H, m), 6.48 (2H, d, J=8.4 Hz), 6.70-6.85(3H, m), 6.95(1H, dd, J=7.8, 1.6 Hz), 7.02(2H, d, J=8.6 Hz), 7.03-7.14(2H, m), 7.25-7.35 (2H, m)

Example 28

Compounds [II] shown in Table 1 can be produced in the same manner as that in Example 1 except that 3-fluoro-5,11-dihydrodibenzo[b,e][1,4]oxazepine was replaced with a compound [V] shown in Table 1 and that (R)-3-chloro-1-(4-metoxyphenethyl)piperidine was replaced with a compound [VI] shown in Table 1.

TABLE 1

| raw material [V] | raw material [VI] | product [II] |
|---|---|---|

TABLE 1-continued
| raw material [V] | raw material [VI] | product [II] |
|---|---|---|
|  | 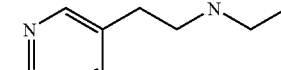 |  |
| 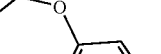 |  |  |
|  |  |  |
|  | 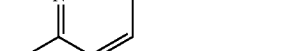 |  |
| 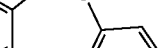 |  |  |

Example 29

Compounds [III] shown in Table 2 can be produced in the same manner as that in Example 16 except that 2-fluoro-5,11-dihydrodibenzo[b,e][1,4]oxazepine was replaced with a compound [V] shown in Table 2 and that (S)-1-(4-dimethylaminophenethyl)-3-methanesulfonyloxypyrrolidine was replaced with a compound [XI] shown in Table 2.

TABLE 2

TABLE 2-continued

| raw material [V] | raw material [XI] | product [III] |
|---|---|---|

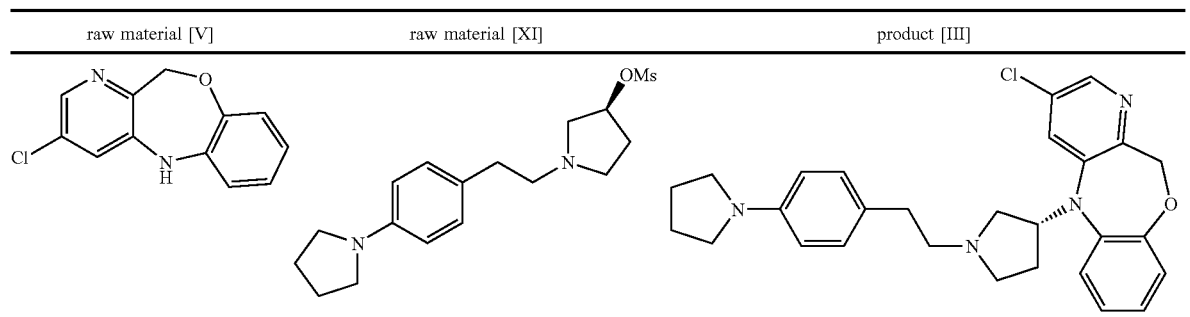

Example 30

Compounds [IV] shown in Table 3 can be produced in the same manner as that in Example 24 except that 2-fluoro-5, 11-dihydrodibenzo[b,e][1,4]oxazepine was replaced with a compound [V] shown in Table 3 and that 3-pyrrolidinophenethyl mesylate was replaced with a compound [X] shown in Table 3.

TABLE 3

| raw material [V] | raw material [X] | product [IV] |
|---|---|---|

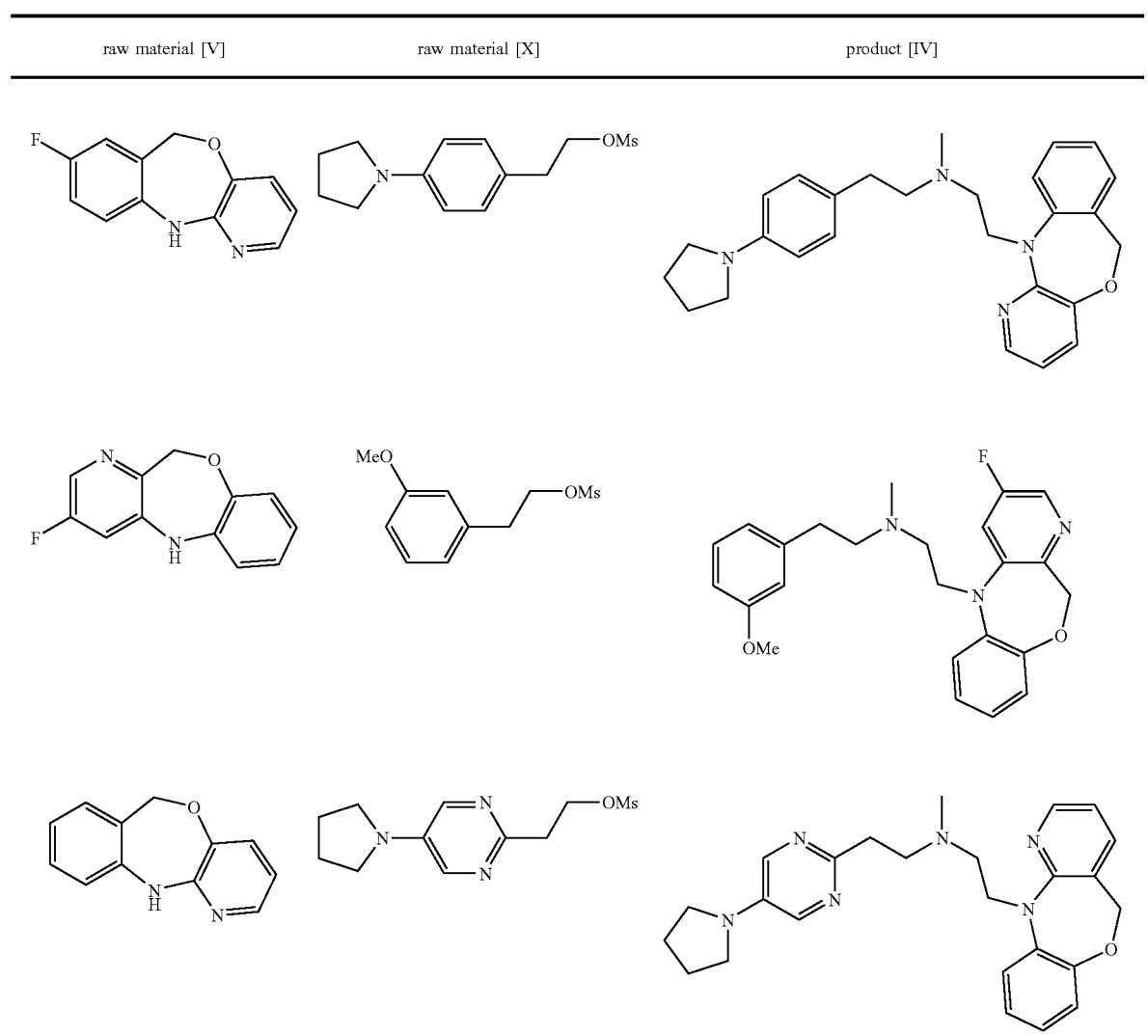

TABLE 3-continued

| raw material [V] | raw material [X] | product [IV] |
|---|---|---|

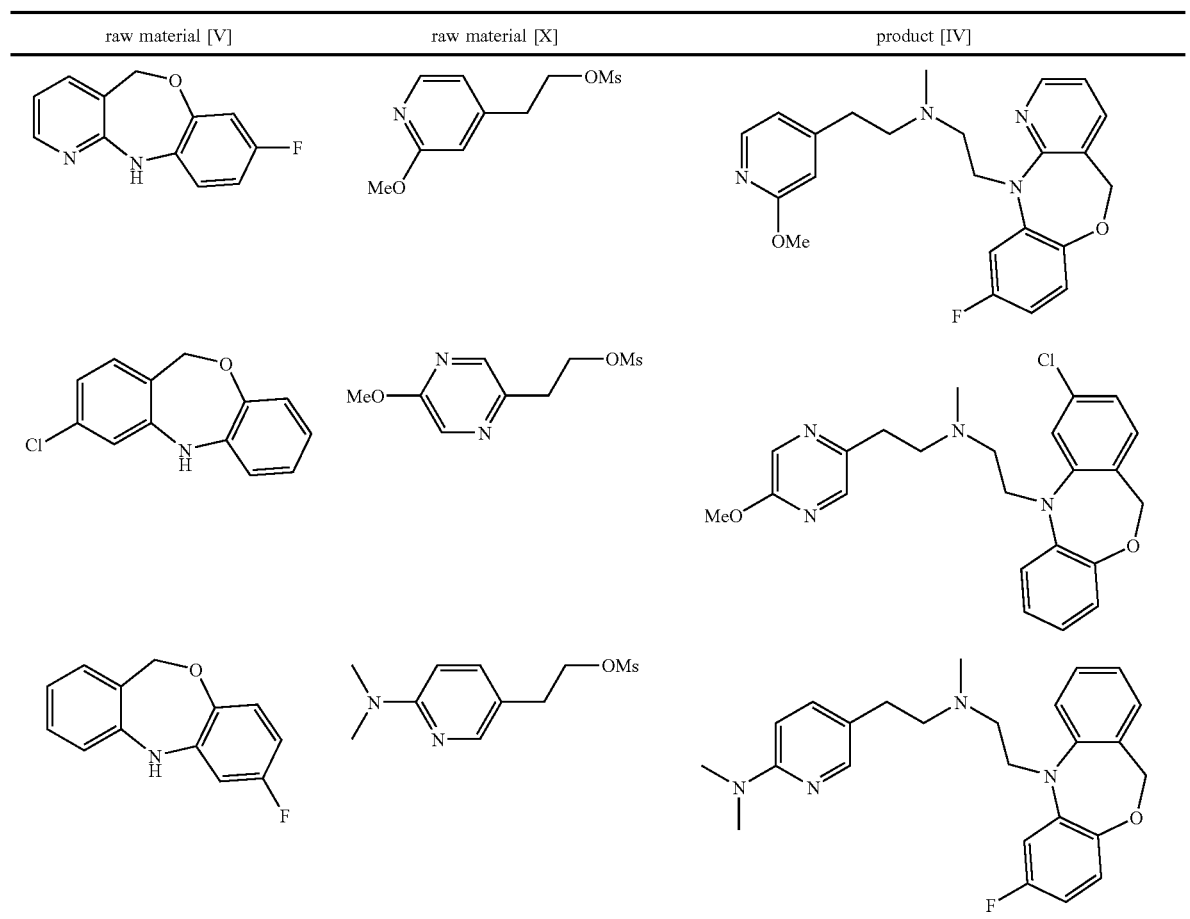

Preparation Examples

Preparation Examples will be given below.

Preparation Example 1

The following ingredients were mixed together by an ordinary method and then tableted to obtain a tablet containing 50 mg of the active ingredient.

| | |
|---|---|
| Compound of Example 8 | 50 mg |
| Lactose | 200 mg |
| Crystalline cellulose | 40 mg |
| Magnesium stearate | 5 mg |

Preparation Example 2

A mixture of the following ingredients was granulated by an ordinary method to obtain granules.

| | |
|---|---|
| Compound of Example 8 | 50 mg |
| Lactose | 90 mg |
| Corn starch | 60 mg |

-continued

| | |
|---|---|
| Talc | 30 mg |
| Magnesium stearate | 10 mg |

Text Examples

The description will be made below on the pharmacological tests of the compounds of the present invention.

Test Example 1

In Vitro Calcium Channel Antagonism (Blood Vessel)

The thoracic aorta of each male Crj:CD rat (8 to 12 weeks old) was extracted to form a spiral preparation. The blood vessel preparation was suspended in a Tyrode's solution of 37° C. which was oxygenated with a mixed gas (containing 95% oxygen and 5% carbon dioxide). The change in the tension of the blood vessel was isometrically recorded on a pen-writing recorder through a transducer. The. high potassium-induced contraction was caused by replacing a normal Tyrode's solution with a high potassium Tyrode's solution (containing 94.6 mM of NaCl, 45.0 mM of KCl, 1.8 mM of $CaCl_2$, 1.04 mM of $MgCl_2$, 0.4 mM of $NaH_2PO_4$, 11.9 mM of HaHCO₃ and 5.55mM of glucose). The effect of the test compound to inhibit the contraction by high potassium was determined by 30 minutes pretreatment. The calcium channel antagonistic activity is evaluated in terms of the concentration ($IC_{50}$) of the test compound showing the 50% inhibition of the contraction (Table 4).

Test Example 2

In Vitro Calcium Channel Antagonism (Ileum)

The ileum was extracted from a portion which was 3 cm apart from the ileocecal region of each male Crj:CD rat (8 to 12 weeks old). The ileum preparation thus obtained was suspended in a Tyrode's solution of 37° C. in which was oxygenated with a mixed gas (containing 95% oxygen and 5% carbon dioxide). The change in the tension of the ileum was isotonically recorded on a pen-writing recorder through a transducer. The high potassium-induced contraction was caused by replacing a normal Tyrode's solution with a high potassium Tyrode's solution (containing 94.6 mM of NaCl, 45.0 mM of KCl, 1.8 mM of CaCl₂, 1.04 mM of MgCl₂, 0.4 mM of NaH₂PO₄, 11.9 mM of HaHCO₃ and 5.55 mM of glucose). The effect of the test compound to inhibit the contraction by high potassium was determined by 30 minutes pretreatment. The calcium channel antagonistic activity is evaluated in terms of the concentration ($IC_{50}$) of the test compound showing the 50% inhibition of the contraction (Table 4). The ratio of the $IC_{50}$ for the blood vessel to the $IC_{50}$ for the ileum is also shown as the selectivity in Table 4.

TABLE 4

| Example No. | structural formula | $IC_{50}$(nM) blood vessel[a] | $IC_{50}$(nM) ileum[b] | selectivity a/b |
|---|---|---|---|---|
| 1 | | 163.0 | 22.0 | 7.4 |
| 2 | | 186.3 | 19.0 | 9.8 |
| 3 | | 556.7 | 39.0 | 14.3 |

TABLE 4-continued
| Example No. | structural formula | IC₅₀(nM) blood vessel[a] | IC₅₀(nM) ileum[b] | selectivity a/b |
|---|---|---|---|---|
| 4 | 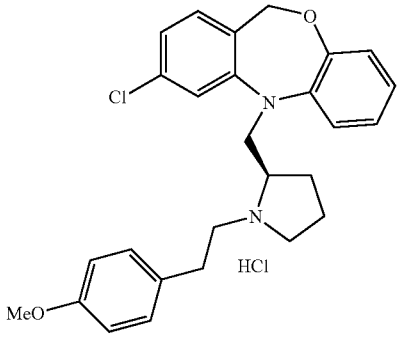 | 107.0 | 17.5 | 6.1 |
| 5 | 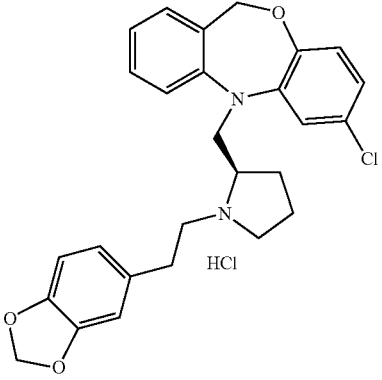 | 590.3 | 71.0 | 8.3 |
| 6 | 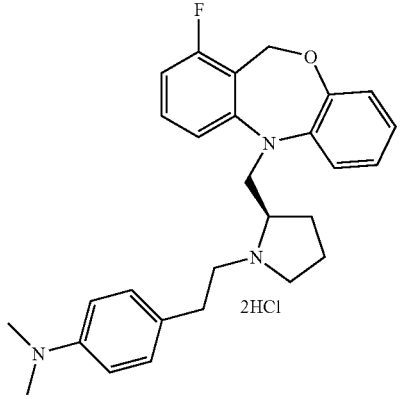 | 631.0 | 79.7 | 7.9 |
| 7 | 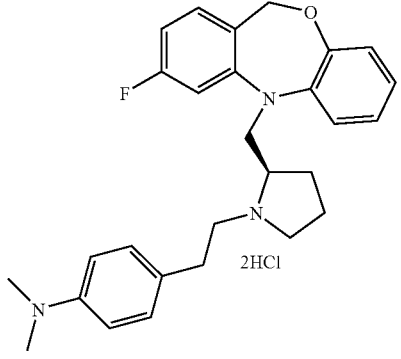 | 121.0 | 19.8 | 6.1 |

TABLE 4-continued

| Example No. | structural formula | IC$_{50}$(nM) blood vessel[a] | IC$_{50}$(nM) ileum[b] | selectivity a/b |
|---|---|---|---|---|
| 8 | | 236.0 | 6.1 | 38.7 |
| 9 | | 134.7 | 15.0 | 9.0 |
| 10 | | 142.7 | 12.6 | 11.3 |
| 11 | | 145.0 | 11.0 | 13.2 |

TABLE 4-continued
| Example No. | structural formula | IC$_{50}$(nM) blood vessel[a)] | IC$_{50}$(nM) ileum[b)] | selectivity a/b |
|---|---|---|---|---|
| 12 | 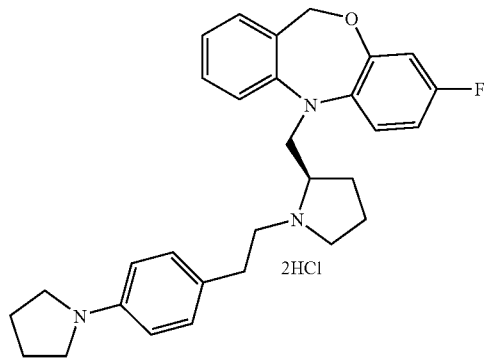 | 193.3 | 14.2 | 13.6 |
| 13 | 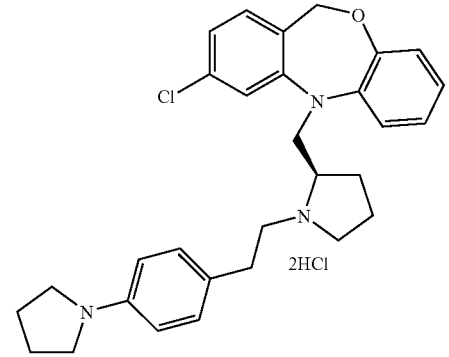 | 156.7 | 15.3 | 10.2 |
| 14 | 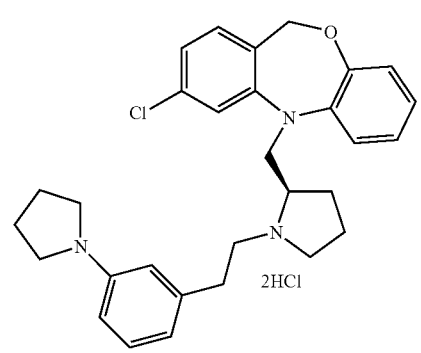 | 611.3 | 82.5 | 7.4 |
| 15 | 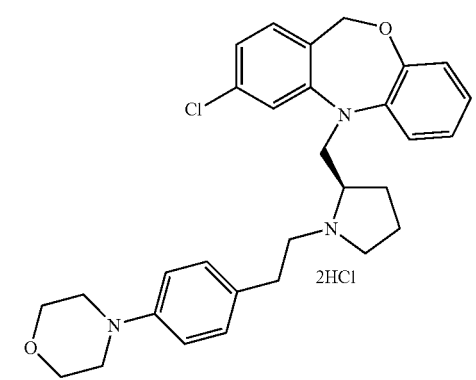 | 22.7 | 9.0 | 2.5 |

TABLE 4-continued
| Example No. | structural formula | IC$_{50}$(nM) blood vessel[a)] | IC$_{50}$(nM) ileum[b)] | selectivity a/b |
|---|---|---|---|---|
| 16 | 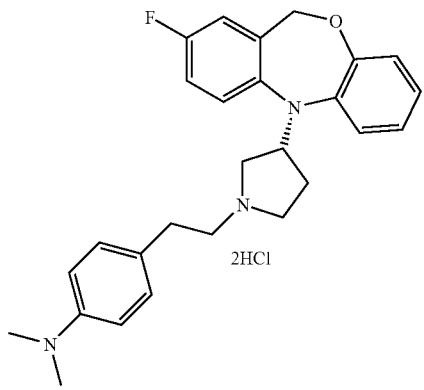 2HCl | 92.7 | 12.0 | 7.7 |
| 17 | 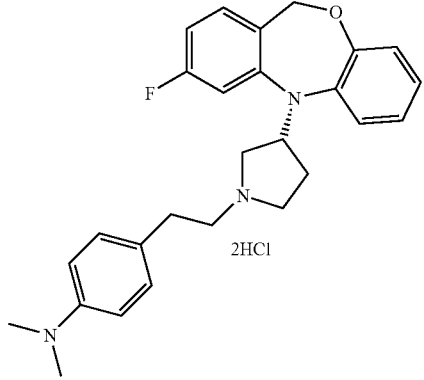 2HCl | 64.0 | 8.4 | 7.6 |
| 18 | 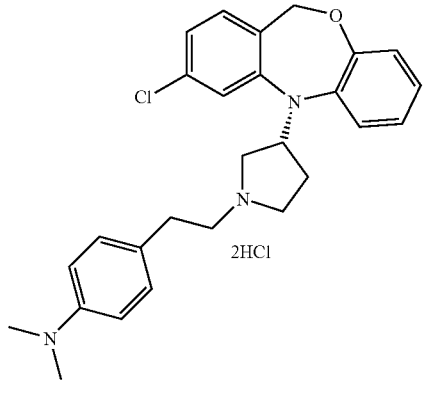 2HCl | 42.3 | 5.6 | 7.6 |
| 19 | 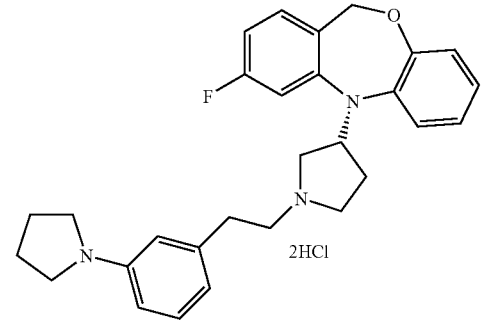 2HCl | 95.3 | 15.3 | 6.2 |

TABLE 4-continued

| Example No. | structural formula | IC$_{50}$(nM) blood vessel[a] | IC$_{50}$(nM) ileum[b] | selectivity a/b |
|---|---|---|---|---|
| 20 | | 67.3 | 11.1 | 6.1 |
| 21 | | 813.3 | 59.5 | 13.7 |
| 22 | | 114.3 | 13.3 | 8.6 |
| 23 | | 158.3 | 17.3 | 9.2 |

TABLE 4-continued

| Example No. | structural formula | $IC_{50}$(nM) blood vessel[a] | $IC_{50}$(nM) ileum[b] | selectivity a/b |
|---|---|---|---|---|
| 24 | | 274.0 | 33.8 | 8.1 |

It was confirmed from the results shown in Table 4 that the compounds of the present invention have an extremely strong calcium channel antagonistic effect and that they are calcium channel antagonists having a high selectivity toward the intestinal tracts. Although International Patent Nos. 9912925A1 and 0040570A1 disclose the calcium antagonistic effect of various 5,11-dihydroibenzo[b,e][1,4]oxazepine derivatives tested by the same method, it was confirmed that the compounds of the present invention are superior to those compounds in the antagonistic effect on the intestinal tracts and the selectivity toward the intestinal tracts.

Test Example 3

Effects on in vivo 5-hydroxytryptophan (5-HTP)-induced defecation models of mice The tests were conducted by a method of G. J. Sanger et al. (British Journal of Pharmacology, 130: 706-712, 2000).

Male SLC:ICR mice (6 weeks old) were moved to 5stainless steel cages connected together for mice. After the naturalization for at least one hour, a test compound was orally administered (n=10). 30 minutes after, 10 mg/5 mL/kg of 5-HTP or vehicle (5mL/kg of physiological saline for a group for which 5-HTP was not used) was injected subcutaneously. The state of the fecal pellets of each mouse excreted in 30 minutes immediately after the injection was observed [scored as 0 (normal fecal pellets or no fecal pellets) or 1(diarrhea or loose stool)]. The score obtained by subtracting the score of the group to which 5-HTP had not been given from the score of the group to which 5-HTP had been given was taken as 100%. The amount of a test compound for 50% control (ID50) was calculated.

ID50 in Example 8 was 8.3 mg/kg.

Test Example 4

Effect of Elevating the Threshold Value of Abdominal Pain in in vivo Rat Colorectal Distension Models The tests were conducted by a method of Saito et al. (Anesth. Analg. 1998; 87: 382-387).

Male Crj:CD rats (250-350 g) were used. A test compound was orally administered to them (n=8). A balloon (length: 7 cm) for dilating the colon was connected to a transducer. After fasting each rat for one day, the balloon was noninvasively inserted internally into the colorectal portion and the base of the balloon was positioned 1 cm from anus under light anesthesia with ether. Water was injected into the balloon at a rate of 0.9 ml/min until the inner pressure in the balloon reached 100 mmHg (cut off value). When the contraction of the abdominal muscle was macroscopically observed during the colon distension, the pressure in the balloon was taken as the threshold value of abdominal pain. The colon distension was conducted at intervals of at least 5 minutes.

The analgesic effect was determined according to the following formula:

Analgesic effect (%)=[(threshold value of abdominal pain after treatment with test compound)−(threshold value of abdominal pain before treatment with test compound)]/[100−(threshold value of abdominal pain before treatment with test compound)]×100.

The analgesic effect was calculated as the dose of the test compound required for 50% control (ID50).

ID50 in Example 8 was 2.6 mg/kg and that in Example 12 was 1.9 mg/kg.

It was confirmed that when the test compounds of the present invention were orally administered to the normotensive rats, both the blood pressure and the heart rate were not significantly influenced by them.

It will be apparent from the Test Examples given above that the compounds of the present invention can exhibit effects as agents for treating or preventing functional diseases of digestive tracts, particularly intestinal diseases such as irritable bowel syndrome.

What is claimed is:

1. A 5,11-Dihydrodiaryl[b,e][1,4]oxazepine represented by the following formula [I], a stereoisomer thereof, a pharmacologically acceptable salt thereof, or a hydrate thereof:

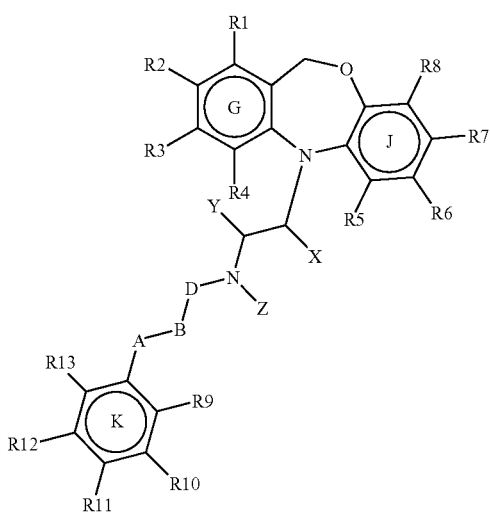

wherein rings G, J and K each represent benzene ring or a nitrogen-containing aromatic ring; each of R1, R2, R3, R4, R5, R6, R7, and R8 may be the same or different from one another and they each represent a halogen atom or hydrogen atom, each of R9, R10, R11, R12, and R13 may be the same or different from one another and they each represent a hydrogen atom, a halogen atom, cyano group, hydroxyl group, a lower alkyl group, a lower alkoxyl group, amino group, a lower alkylamino group, a lower acylated amino group, a lower acylated lower alkylamino group, a lower dialkylamino group or a cycloalkylamino group, or R9 and R10 or R10 and R11 together form —O(CH$_2$)$_n$,O— group wherein n' is 1, 2 or 3; A represents CH$_2$, CHOH, CO or O; B represents CH$_2$, CHOH or CO; or A-B represents CH=CH, D represents CH$_2$, CH$_2$—CH$_2$ or CH$_2$—CH$_2$—CH$_2$ or B-D represents CH$_2$; X and z are bonded together to form CH$_2$—CH$_2$ or CH$_2$—CH$_2$—CH$_2$ and, in this case, Y represents a hydrogen atom; or Y and z are bonded together to form CH$_2$—CH$_2$—CH$_2$ or CH$_2$—CH$_2$—CH$_2$—CH$_2$ and, in this case, X represents a hydrogen atom; and when X and z, and Y and z are not bonded together, X and Y each represent a hydrogen atom and z represents a lower alkyl group;

provided that when any of R9, R10, R11, R12, and R13 represents a cyclic amino group of the following formula [E], each of R1, R2, R3, R4, R5, R6, R7, and R8 may be a halogen atom or hydrogen atom but when none of R9, R10, R11, R12, and R13 is a cyclic amino group of formula [E], one or two of R1, R2, R3, R4, R5, R6, R7, and R8 represent a halogen atom and the others represent a hydrogen atom:

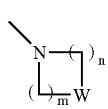

[E]

wherein n and m each represent 1 or 2, and W represents carbon atom, or nitrogen which may be substituted with a lower alkyl group, or oxygen, or sulfur atom.

2. The 5,11-dihydrodiaryl[b,e][1,4]oxazepine, stereoisomer thereof, pharmacologically acceptable salt thereof, or hydrate thereof according to claim 1 wherein rings G and J are both benzene rings.

3. The 5,11-dihydrodiaryl[b,e][1,4]oxazepine, stereoisomer thereof, pharmacologically acceptable salt thereof, or hydrate thereof according to claim 1 wherein either ring G or J is pyridine ring and the other is benzene ring.

4. The 5,11-dihydrodiaryl[b,e][1,4]oxazepine, stereoisomer thereof, pharmacologically acceptable salt thereof, or hydrate thereof according to any one of claims 1 to 3 wherein ring K is benzene ring.

5. The 5,11-dihydrodiaryl [b,e][1,4]oxazepine, stereoisomer thereof, pharmacologically acceptable salt thereof, or hydrate thereof according to any one of claims 1 to 3 wherein ring K is pyridine ring, pyrimidine ring, pyrazine ring or pyridazine ring.

6. The 5,11-dihydrodiaryl[b,e][1,4]oxazepine, stereoisomer thereof, pharmacologically acceptable salt thereof, or hydrate thereof according to claim 1 wherein rings G, J and K are benzene rings.

7. The 5,11-dihydrodiaryl[b,e][1,4]oxazepine, stereoisomer thereof, pharmacologically acceptable salt thereof, or hydrate thereof according to claim 1, wherein X and z are bonded together to form CH$_2$—CH$_2$ or CH$_2$—CH$_2$—CH$_2$ and Y represents a hydrogen atom.

8. The 5,11-dihydrodiaryl[b,e][1,4]oxazepine, stereoisomer thereof, pharmacologically acceptable salt thereof, or hydrate thereof according to claim 1, wherein Y and z are bonded together to form CH$_2$—CH$_2$—CH$_2$ or CH$_2$—CH$_2$—CH$_2$—CH$_2$ and X represents a hydrogen atom.

9. The 5,11-dihydrodiaryl[b,e][1,4]oxazepine, stereoisomer thereof, pharmacologically acceptable salt thereof, or hydrate thereof according to claim 1, wherein X and Y are each a hydrogen atom and z represents a lower alkyl group.

10. The 5,11-dihydrodiaryl[b,e][1,4]oxazepine, stereoisomer thereof, pharmacologically acceptable salt thereof, or hydrate thereof according to claim 1, wherein either or both of R10 and R11 are methoxyl group or R10 and R11 together form methylenedioxyl group, and R9, R12 and R13 are each a hydrogen atom.

11. The 5,11-dihydrodiaryl [b,e][1,4]oxazepine, stereoisomer thereof, pharmacologically acceptable salt thereof, or hydrate thereof according to claim 1, wherein R11 is methoxyl group, and R9, R10, R12 and R13 are each a hydrogen atom.

12. The 5,11-dihydrodiaryl[b,e][1,4]oxazepine, stereoisomer thereof, pharmacologically acceptable salt thereof, or hydrate thereof according to claim 1, wherein either R10 or R11 is amino group, a lower alkylamino group, a lower acylated amino group, a lower acylated lower alkylamino group, a lower dialkylamino group or a cycloalkylamino group, and the other is a hydrogen atom.

13. The 5,11-dihydrodiaryl[b,e][1,4]oxazepine, stereoisomer thereof, pharmacologically acceptable salt thereof, or hydrate thereof according to claim 1, wherein either R10 or R11 is a cyclic amino group represented by formula [E] and the other is a hydrogen atom.

14. The 5,11-dihydrodiaryl[b,e][1,4]oxazepine, stereolsomer thereof, pharmacologically acceptable salt thereof, or hydrate thereof according to claim 13 wherein all of R1 to R8 are a hydrogen atom.

15. The 5,11-dihydrodiaryl[b,e][1,4]oxazepine, stereoisomer thereof, pharmacologically acceptable salt thereof, or hydrate thereof according to claim 1, wherein one of R1, R2, R3, R4, R5, R6, R7, and R8 is fluorine atom or chlorine atom and the other is a hydrogen atom.

16. The 5,11-dihydrodiaryl[b,e][1,4]oxazepine, stereoisomer thereof, pharmacologically acceptable salt thereof, or hydrate thereof according to claim 1, wherein one of R2, R3, R6 and R7 is fluorine atom or chlorine atom and others are each a hydrogen atom.

17. The 5,11-dihydrodiaryl[b,e][1,4]oxazepine, stereoisomer thereof, pharmacologically acceptable salt thereof, or hydrate thereof according to claim 1, wherein A and B-D are both $CH_2$.

18. The 5,11-dihydrodiaryl[b,e][1,4]oxazepine, pharmacologically acceptable salt thereof, or hydrate thereof according to claim 7 wherein the carbon atom to which X is bonded has an absolute configuration of R.

19. The 5,11-dihydrodiaryl[b,e][1,4]oxazepine, pharmacologically acceptable salt thereof, or hydrate thereof according to claim 7 wherein the carbon atom to which X is bonded has an absolute configuration of S.

20. The 5,11-dihydrodiaryl[b,e][1,4]oxazepine, pharmacologically acceptable salt thereof, or hydrate thereof according to claim 8 wherein the carbon atom to which Y is bonded has an absolute configuration of R.

21. The 5,11-dihydrodiaryl[b,e][1,4]oxazepine, pharmacologically acceptable salt thereof, or hydrate thereof according to claim 8 wherein the carbon atom to which Y is bonded has an absolute configuration of S.

22. A pharmaceutical composition, which comprises at least one 5,11-dihydrodiaryl[b,e][1,4]oxazepine, stereoisomer thereof, pharmacologically acceptable salt thereof, or hydrate thereof according to claim 1 and at least one pharmaceutically acceptable carrier.

23. A pharmaceutical composition, which comprises at least one 5,11-dihydrodiaryl[b,e][1,4]oxazepine, stereoisomer thereof, pharmacologically acceptable salt thereof, or hydrate thereof according to claim 6 and at least one pharmaceutically acceptable carrier.

24. A method for treating a functional disease of the digestive tract, said method comprising administering an effective amount of a 5,11-dihydrodiaryl[b,e][1,4]oxazepine, a stereoisomer thereof, a pharmacologically acceptable salt thereof or a hydrate thereof according to claim 1 to a subject in need thereof, wherein said functional disease of the digestive tract is selected from the group consisting of irritable bowel syndrome, rumination syndrome, globus syndrome, functional heart burn, functional chest pain of presumed esophageal origin, functional gastrointestinal disorder, functional dysphagia, functional vomiting, deglutition disorder, aerophagia, functional constipation, functional abdominal bloating, functional abdominal pain syndrome, functional diarrhea, sphincter of Oddi's dysfunction, gallbladder dysfunction, levator ani syndrome, functional fecal incontinence, pelvic floor dyssynergia proctalgia fugax, and a pediatric gastrointestinal function disorder.

25. The method according to claim 24, wherein said functional disease of the digestive tract is irritable bowel syndrome.

26. The method according to claim 24, wherein said pediatric gastrointestinal function disorder is selected from the group consisting of infant regurgitation syndrome, infant rumination syndrome, cyclic vomiting syndrome, functional gastrointestinal disorders, irritable bowel syndrome, functional abdominal pain, paroxysmal abdominal pain, aerophagia, functional diarrhea, infant dyschezia, functional constipation, functional fecal retention, and functional nonretentive fecal soiling.

* * * * *